Figure 3A:
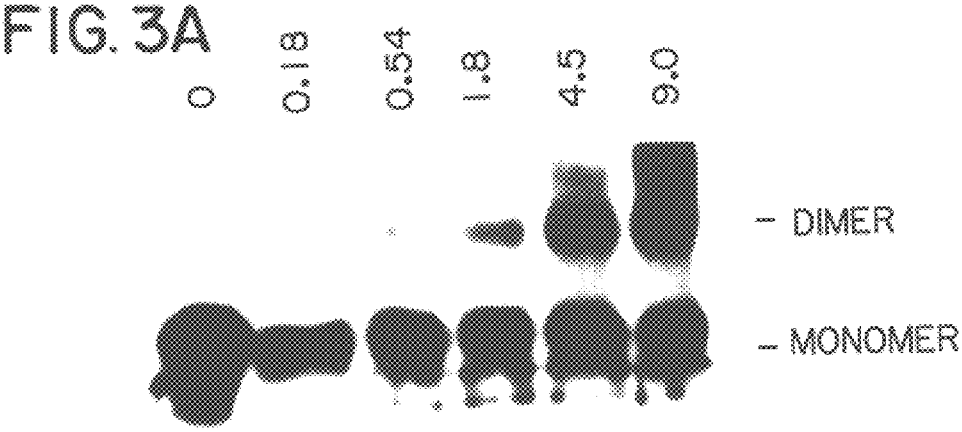

United States Patent [19]
Greve et al.

[11] Patent Number: 6,130,202
[45] Date of Patent: *Oct. 10, 2000

[54] ANTIVIRAL METHODS

[75] Inventors: Jeffrey M. Greve, Woodbridge, Conn.; Alan McClelland, Gaithersburg, Md.

[73] Assignee: Bayer Corporation, Pittsburgh, Pa.

[*] Notice: This patent is subject to a terminal disclaimer.

[21] Appl. No.: 08/227,496

[22] Filed: Apr. 14, 1994

Related U.S. Application Data

[63] Continuation of application No. 07/903,069, Jun. 22, 1992, abandoned, which is a continuation-in-part of application No. 07/704,984, May 24, 1991, abandoned, which is a continuation-in-part of application No. 07/556,238, Jul. 20, 1990, abandoned.

[51] Int. Cl.⁷ .......................... A61K 38/04; A61K 38/08; A61K 38/10; A61K 38/16

[52] U.S. Cl. .................. 514/12; 514/13; 514/14; 514/15; 514/16; 514/17; 424/185.1; 530/324; 530/325; 530/326; 530/327; 530/328; 530/329; 530/350; 530/395; 530/402; 530/345

[58] Field of Search ..................... 530/300, 350, 530/395, 402, 403, 324, 325, 326, 327, 328, 329, 345; 514/12, 8; 424/184.1, 185.1

[56] References Cited

U.S. PATENT DOCUMENTS

| | | |
|---|---|---|
| 5,081,228 | 1/1992 | Dower et al. . |
| 5,179,017 | 1/1993 | Axel et al. . |
| 5,235,049 | 8/1993 | McClelland et al. . |
| 5,240,694 | 8/1993 | Gwaltney, Jr. . |
| 5,284,931 | 2/1994 | Springer et al. . |
| 5,304,636 | 4/1994 | Blaas et al. . |
| 5,324,510 | 6/1994 | Wegner et al. . |
| 5,340,800 | 8/1994 | Liu et al. . |
| 5,349,053 | 9/1994 | Landolfi . |
| 5,359,046 | 10/1994 | Capon et al. . |
| 5,372,933 | 12/1994 | Zamarron et al. . |
| 5,395,929 | 3/1995 | Corbi et al. . |
| 5,422,097 | 6/1995 | Gwaltney . |
| 5,472,849 | 12/1995 | Rothlein et al. . |
| 5,475,091 | 12/1995 | Springer et al. . |
| 5,525,487 | 6/1996 | Gallatin et al. . |
| 5,532,127 | 7/1996 | Gallatin et al. . |
| 5,580,969 | 12/1996 | Hoke et al. . |
| 5,589,453 | 12/1996 | Greve ......................................... 514/8 |
| 5,597,567 | 1/1997 | Whitcup et al. . |
| 5,603,932 | 2/1997 | Blaas et al. . |
| 5,612,216 | 3/1997 | Springer et al. . |
| 5,663,293 | 9/1997 | Gallatin et al. . |
| 5,674,982 | 10/1997 | Greve et al. . |
| 5,686,581 | 11/1997 | Greve et al. . |
| 5,686,582 | 11/1997 | Greve et al. . |
| 5,712,245 | 1/1998 | Blaas et al. . |
| 5,730,983 | 3/1998 | Wegner et al. . |
| 5,821,341 | 10/1998 | McClelland et al. . |
| 5,831,036 | 11/1998 | Springer et al. . |
| 5,849,699 | 12/1998 | McClelland et al. . |
| 5,871,733 | 2/1999 | Greve et al. . |

FOREIGN PATENT DOCUMENTS

| | | |
|---|---|---|
| 1551888 | 11/1988 | Australia . |
| 2633288 | 5/1989 | Australia . |
| 623105 | 6/1989 | Australia . |
| 637324 | 3/1990 | Australia . |
| 5129990 | 9/1990 | Australia . |
| 623105 | 5/1992 | Australia . |
| 637324 | 5/1993 | Australia . |
| 641134 | 9/1993 | Australia . |
| 652567 | 9/1994 | Australia . |
| 675441 | 2/1997 | Australia . |
| 1339193 | 8/1997 | Canada . |
| 0287076 | 10/1988 | European Pat. Off. . |
| 0468257 | 1/1992 | European Pat. Off. . |

(List continued on next page.)

OTHER PUBLICATIONS

Pepinsky, R.B. et al. J.B.C., 266(27):18244–49 (1991) "The Increased Potency of Cross–linked Lymphocyte Function–associated Antigen–3 (LFA–3) Mutimers is a Direct Consequence of Changes in Valency."

Dustin, M.L., et al. J. Immunology 137(1):245–254 (1986). Induction by IL–1 and Interferon–gamma Tissue Distribution, Biochemistry, and Function of a Natural Adherence Molecule (ICAM1).

Dustin, M.L., et al., J. Exp. Med. 169:503–517 (1989), "Correlation of CUZ Binding and Functional Properties of Multimeric and Monomeric Lymphocyte Function–associated Antigen 3."

Rothlein, R. et al., J. Immunol. 137(4):1270–1274 (1986). "A Human Intercellular Adhesion Molecule (ICAM–1) Distinct from LFA–1."

Tomassini, J.E., et al. J. Virology, 58(2):290–295 (1986). "Isolation of a Receptor Protein Involved in Attachment of Human Rhinovirus."

Al–Nakib, W., P.G. Higgins, G.I. Barrow, D.A.J. Tyrrell, K. Andries, G. Vanden Bussche, N. Taylor, and P.A.J. Janssen, "Suppression of Colds in Human Volunteers Challenged with Rhinoviurs by a New Synthetic Drug (R61837)", Antimicrobial Agents and Chemotherapy 33(4): 522–525 (Apr. 1989).

(List continued on next page.)

Primary Examiner—Christina Y. Chan
Assistant Examiner—Marianne DiBrino

[57] ABSTRACT

Methods for inhibiting infectivity and reducing infection by human rhinovirus (HRV) of host cells susceptible to infection by HRV and methods of inhibiting initiation and spread of the common cold, said methods comprising contacting HRV under conditions favorable for binding with a multimeric antiviral agent comprising two or more units wherein said units may be the same or different and are each independently selected from the group consisting of transmembrane intercellular adhesion molecule-1 (tmICAM-1) and truncated forms of intercellular adhesion molecule-1 (tICAMs), each of said units containing at least one unpaired cysteine residue at a position selected from the group consisting of 307 and 309, wherein each of said units is linked to at least one other of said units via a disulfide bridge, and wherein said multimeric antiviral agent binds to HRV and reduces infectivity thereof.

7 Claims, 7 Drawing Sheets

FOREIGN PATENT DOCUMENTS

| | | |
|---|---|---|
| 0510483 | 10/1992 | European Pat. Off. . |
| 0566554 | 10/1993 | European Pat. Off. . |
| 0319815 | 8/1994 | European Pat. Off. . |
| 0379904 | 5/1996 | European Pat. Off. . |
| 0488061 | 11/1998 | European Pat. Off. . |
| 100601 | 1/1998 | Finland . |
| 74144 | 7/1997 | Ireland . |
| 91454 | 8/1995 | Israel . |
| 230474 | 8/1989 | New Zealand . |
| 232203 | 1/1990 | New Zealand . |
| 92920 | 7/1990 | Portugal . |
| 91570 | 11/1994 | Portugal . |
| 202435 | 6/1999 | Rep. of Korea . |
| 900469 | 10/1990 | South Africa . |
| 52785 | 11/1991 | Taiwan . |
| 52785 | 3/1992 | Taiwan . |
| 9201049 | 1/1992 | WIPO . |
| 9206119 | 4/1992 | WIPO . |
| 9212994 | 8/1992 | WIPO . |
| 9306842 | 4/1993 | WIPO . |
| 9306850 | 4/1993 | WIPO . |
| 9313210 | 7/1993 | WIPO . |
| 9401553 | 1/1994 | WIPO . |
| 9411400 | 5/1994 | WIPO . |
| 9527736 | 10/1995 | WIPO . |
| 9528170 | 10/1995 | WIPO . |
| 9606622 | 3/1996 | WIPO . |
| 9627292 | 9/1996 | WIPO . |
| 9634015 | 10/1996 | WIPO . |

OTHER PUBLICATIONS

Amzel, L. M., and R.J. Poljak, "Three Dimensional Structure of Immunoglobulins", Ann. Rev. Biochem. 48: 961–997 (1979).

Becker, J. W., and G.N.Reeke, Jr., "Three–dimensional structure of $\beta_2$–microglobulin", Proc. Natl. Acad. Sci. USA 82: 4225–4229 (Jun. 1985).

Becker, J. W., H.P. Erickson, S. Hoffman, B.A. Cunningham, and G.M. Edelman, "Topology of cell adhesion molecules", Proc. Natl. Acad. Sci. USA, 86: 1088–1092 (Feb. 1989).

Bjorkman, P. J., M.A. Saper, B. Samraoui, W.S. Bennett, J.L. Strominger, and D.C. Wiley, "Structure of the human class I histocompatibility antigen, HLA–A2", Nature 329: 506–512 (Oct. 1987).

Colman, P.M., "Structure of Antibody–Antigen Complexes: Implications for Immune Recognition", Advances in Immunology 43: 99–132 (1988).

Colonno, R. J., J.H. Condra, S. Mizutani, P.L. Callahan, M.–E.Davies, and M.A. Murcko, "Evidence for the direct involvement of the rhinovirus canyon in receptor binding", Proc. Natl. Acad. Sci. USA 85: 5449–5453 (Aug. 1988).

Craig, A. G. and A.R. Berendt, "The Role of ICAM–1 as a Receptor for Rhinovirus and Malaria", in *Integrins and ICAM–1 in Immune Responses,* N. Hodd, ed. (Chem Immunol. Basel, Karger, 1991), vol. 50, pp. 116–134 (1991).

Crump, C. E., E. Arruda, and F.G. Hayden, "Comparative Antirhinoviral Activities of Soluble Intercellular Adhesion Molecule–1 (sICAM–1) and Chimeric ICAM–1/Immunoglobulin A Molecule", Antimicrobial Agents and Chemotherapy 38(6): 1425–1427 (Jun. 1994).

Dayhoff, M. O., W.C. Barker, and L.T. Hunt, "Establishing Homologies in Protein Sequences", Methods in Enzymology 91: 524–545 (1983).

Dearden, C., W. Al–Nakib, K. Andries, R. Woestenborghs, and D.A.J. Tyrrell, "Drug resistant rhinoviruses from the nose of experimentally treated volunteers", Arch. Virol. 109: 71–81 (1989).

Dustin, M. L. and T.A. Springer, "Lymphocyte Function-–associated Antigen–1 (LFA–1) Interaction with Intercellular Adhesion Molecule–1 (ICAM–1) is One of At Least Three Mechanisms for Lymphocyte Adhesion to Cultured Endothelial Cells", J. Cell Biol. 107: 321–331 (Jul. 1988).

Ezekovitz, R.A.B., R.B. Sim, G.G. MacPherson, and S. Gordon, "Interaction of Human Monocytes, Macrophages, and Polymorphonuclear Leukocytes with Zymosan in Vitro: Role of Type 3 Compliment Receptors and Macrophage Derived Complement", J. Clin. Invest. 76: 2368–2376 (Dec. 1985).

Greve, J. M., C.P. Forte, C.W. Marlor, A.M. Meyer, H. Hoover–Litty, D. Wunderlich, and A. McClelland, "Mechanisms of Receptor–Mediated Rhinovirus Neutralization Defined by Two Soluble Forms of ICAM–1", J. Virol. 65(11): 6015–6023 (Nov. 1991).

Guttman, N., and D. Baltimore, "Plasma Membrane Component Able to Bind and Alter Virions of Poliovirus Type 1: Sutides on Cell–Free Alteration Using a Simplified Assay", Virol. 82: 25–36 (1977).

Gwaltney, J. M., Jr. and J.O. Hendley, "Rhinovirus Transmission: One if by Air, Two if by Hand", Trans. Am. Clin. Climatol. Assoc. 89: 194–200 (1977).

Gwaltney, J. M.,Jr., and J.O. Hendley, "Rhinovirus Transmission One if by Air, Two if by Hand", Am. J. Epid. 107(5): 357–361 (May 1978).

Gwaltney, J. M., Jr., "Rhinovirus colds: epdimiology, clinical characteristics and transmission", Eur. J. Respir. Dis. 64 (suppl. 128): 336–339 (1983).

Gwaltney, J. M., Jr., "Rhinoviruses", Yale J. Biol. Med. 48: 17–45 (1975).

Hayden, F. G., and J.M. Gwaltney, Jr., "Intranasal Interferon–$\alpha_2$ Treatment of Experimental Rhinoviral Colds", J. Infect. Dis. 150(2): 174–180 (Aug. 1984).

Hendley, J. O., and J.M. Gwaltney, Jr., "Mechanisms of Transmission of Rhinovirus Infections", Epidemiologic Reviews 10: 242–258 (1988).

Horley, K. J., C. Carpenito, B. Baker, and F. Takei, "Molecular cloning of murine intercellular adhesion molecule (ICAM–1)", EMBO J. 8(10): 2889–2896 (1989).

Jacobs, K., C. Shoemaker, R. Rudersdorf, S.D. Neill, R.J. Kaufman, A. Mufson, J. Seehra, S.S. Jones, R. Hewick, E.F. Fritsch, M. Kawakita, T. Shimizu, and T. Miyake, "Isolation and characterization of genomic and cDNA clones of human erythropoietin", Nature 313: 806–810 (Feb. 1985).

Kim S., T.J. Smith, M.S. Chapman, M.G. Rossmann, D.C. Pevear, F.J. Dutko, P.J. Felock, G.D. Diana, and M.A. McKinlay, "Crystal Structure of Human Rhinovirus Serotype 1A (HRV1A)", J. Med. Biol. 210: 91–111 (1989).

Layne, S. P., M.J. Merges, M. Dembo, J.L. Spouge, and P.L. Nara, "HIV requires multiple gp120 molecules for CD4–mediated infection", Nature 346: 277–279 (Jul. 1990).

Leonard, W. J., J.M. Depper, G.R. Crabtree, S. Rudikoff, J. Pumphrey, R.J. Robb, M. Krönke, P.B. Svetlik, N.J. Peffer, T.A. Waldmann, and W.C. Greene, "Molecular cloning and expression of cDNAs for the human interleukin–2 receptor", Nature 311: 626–631 (Oct. 1984).

Leszczynski, J. F., and G.D. Rose, "Loops in Globular Proteins: A Novel Category of Secondary Structure", Science 234: 849–855 (Nov. 1986).

Lineberger, D. W., D.J. Graham, J.E. Tomassini, and R.J. Colonno, "Antibodies that Block Rhinovirus Attachment Map to Domain 1 of the Major Group Receptor", J. Virol. 64(6): 2582–2587 (Jun. 1990).

Martin, S., J.M. Casanovas, D.E. Staunton, and T.A. Springer, "Erfolgreiche Blockade von Rhinovirusinfektionen durch ICAM–1–Immunoglobulinchimare in vitro", Med. Klin. 88(4): 193–197 (1993).

McPherson, J. M., and D.J. Livingston, "Protein Engineering: New Approaches to Improved Therapeutic Proteins, Part I", in *Biotech. Trends,* S. Petska, ed. (Pharmaceutical Technology, May 1989).

Livingston, D. J., and J.M. McPherson, "Protein Engineering: New Approaches to Improved Therapeutic Proteins, Part II", in *Biotech. Trends,* S. Petska, ed. (Pharmaceutical Technology, Jun. 1989).

McPherson, J. M., and D.J. Livingston, "Protein Engineering: New Approaches to Improved Therapeutic Proteins, Part III", in *Biotech. Trends,* S. Petska, ed. (Pharmaceutical Technology, Sep. 1989).

McClelland, A., M.E.Kamarck, and F.H. Ruddle, "Molecular Cloning of Receptor Genes by Transfection", Methods in Enzymology 147: 280–291 (1987).

Minor, P. D., "Chapter 2: Growth, Assay and Purification of Picornaviruses", in *Virology: a practical approach* (IRL Press, Washington, D.C., 1985), pp. 25–41.

Minor, P. D., P.A. Pipkin, D. Hockley, G.C. Schild, and J.W. Almond, "Monoclonal antibodies which block cellular receptors of poliovirus", Virus Res. 1: 203–212 (1984).

Morein B., "Potentiation of the Immune Response by Immunization with Antigens in Defined Multimeric Physical Forms", Vet. Immunol. Immunopathol. 17: 153–159 (1987).

Ockenhouse, C.F., R. Betageri, T.A. Springer, and D.E. Staunton, "*Plasmodium falciparum*–Infected Erythrocytes Bind ICAM–1 at a Site Distinct from LFA–1, Mac–1, and Human Rhinovirus", Cell 68: 63–69 (Jan. 1992).

Peppel, K., D. Crawford, and B. Beutler, "A Tumor Necrosis Factor (TNF) Receptor–IgG Heavy Chain Chimeric Protein as a Bivalent Antagonist of TNF Activity", J. Exp. Med. 174: 1483–1489 (Dec. 1991).

Pevear, D. C., M.J. Fancher, P.J. Felock, M.g. Rossmann, M.S. Miller, G. Diana, A.M. Treasurywala, M.A. McKinlay, and F.J. Dutko, "Conformational Change in the floor of the Human Rhinovirus Canyon Blocks Adsorption to HeLa Cell Receptors", J. Virol. 63(5): 2002–2007 (May 1989).

Plow, E. F., M.D. Pierschbacher, E. Ruoslahti, G.A. Marguerie, and M.H. Ginsberg, "The effect of Arg–Gly–Asp––containing peptides on fibrinogen and von Willebrand factor binding to platelets", Proc. Natl. Acad. Sci. USA 82: 8057–8061 (1985).

Ray, C. G., "Chapter 32: Respiratory Viruses", in *Medical Microbiology, an Introduction to Infectious Diseases,* 2nd Ed, J. C. Sherris, ed. (Elsevier, New York, 1990), pp. 499–516.

Roesing, T. G., P.A. Toselli, and R.L. Crowell, "Elution and Uncoating of Coxsackievirus B3 by Isolated HeLa Cell Plasma Membranes", J. Virol. 15(3): 654–667 (Mar. 1975).

Rossmann, M. G., "The Canyon Hypothesis. Hiding the Host Cell Receptor Attachment Site on a Viral Surface from Immune Surveillance", J. Biol. Chem. 264(25): 14587–14590 (Sep. 1989).

Saiki, R.K., D.H. Gelfand, S. Stoffel, S.J. Scharf, R. Higuchi, G.T. Horn, K.B. Mullis, and H.A. Erlich, "Primer–Directed Enzymatic Amplification of DNA with a Thermostable DNA Polymerase", Science 239:487–491 (Jan. 1988).

Sayre, P.H., R.E. Hussey, H.–C. Chang, T.L. Ciardelli, and E.L. Reinherz, "Structural and Binding Analysis of a Two Domain Extracellular CD2 Molecule", J. Exp. Med. 169: 995–1009 (Mar. 1989).

Siu, G., S.M. Hedrick, and A.A. Brian, "Isolation of the Murine Intercellular Adhesion Molecule 1 (ICAM–1) Gene", J. Immun. 143(11): 3813–3820 (Dec. 1989).

Skern, T., W. Sommergruber, D. Blass, P. Gruendler, F. Fraundorfer, C. Pieler, I. Fogy, and E. Kuechler, "Human rhinovirus 2: complete nucleotide sequence and proteolytic processing signals in the capsid protein region", Nucleic Acids Research 13(6): 2111–2126 (1985).

Smilek, D. E., D.C. Wraith, S. Hodgkinson, S. Swivedy, L. Steinman, and H.O. McDevitt, "A single amino acid change in a myelelin basic protein peptide confers the capacity to prevent rather than induce experimental autoimmune encephalomyelitis", Proc. Natl. Acad. Sci. USA 88: 9633–9637 (Nov. 1991).

Staunton, D.E., M.L. Dustin, and T.A. Springer, "Functional cloning of ICAM–2, a cell adhesion ligand for LFA–1 homologous to ICAM–1", Nature 339: 61–64 (May 1989).

Staunton, D.E., C.F. Ockenhouse, and T.A. Springer, "Soluble Intercellular Adhesion Molecule 1–Immunoglubulin G1 Immunoadhesin Mediates Phagocytosis of Malaria–infected Erythrocytes", J. Exp. Med. 176: 1471–1476 (Nov. 1992).

Uncapher, C. R., C.M. De Witt, and R.J. Colonno, "The Major and Minor Group Receptor Families Contain All but One Human Rhinovirus Serotype", Virology 180: 814–817 (1991).

Wickner W. T., and H.F. Lodish, "Multiple Mechanisms of Protein Insertion Into and Across Membranes", Science 230: 400–407 (Oct. 1985).

Weis, W., J.H. Brown, S. Cusack, J.C. Paulson, J.J. Skehel, and D.C. Wiley, "Structure of the influenza virus haemagglutinin complexed with its receptor, sialic acid", Nature 333: 426–431 (Jun. 1988).

R&D Systems (Minneapolis, MN), 1994 Catalog, Item #BBE 1B, "Human Soluble ICAM–1".

"Chapter 9, Introduction of DNA into Mammalian Cells", Current Protocols in Molecular Biology 1997: 9.0.1–9.9.16 (1997).

British Biotechnology, Ltd. (Oxford, England), 1993 Product Catalog, Item #BBE 1, "Soluble ICAM–1 ELISA".

Abraham, G. and R.J. Colonno, "Characterization of human rhinoviruses displaced by an anti–receptor monoclonal antibody", J. Virol.62(7):2300–2306 (Jul. 1988).

Ashkenazi, A., L.G. Presta, S.A. Marsters, T.R. Camerato, K.A. Rosen, B.M. Fendly, and D.J. Capon, "Mapping the CD4 binding site for human immunodeficiency virus by alanine scanning mutagenesis", Proc. Natl. Acad. Sci. USA 87:7150–7154 (Sep. 1990).

Brodsky, M.H., M. Warton, R.M. Myers, and D.R. Littman, "Analysis of the site in CD4 that binds to the HIV envelope glycoprotein", J. Immunol. 144(8):3078–3086 (Apr. 1990).

Callahan, P.L., S. Mizutani, and R.J. Colonno, "Molecular cloning and complete sequence determination of RNA genome of human rhinovirus type 14", Proc. Natl. Acad. Sci. USA 82(3):732–6 (Feb. 1985).

Colonno, R.J., "Virus receptors: the Achilles' heel of human rhinoviruses", in Innovations in Antiviral Development and the Detection of Virus Infection, T. Block et al., eds., (Plenum Press, NY, 1992), pp. 61–70.

Colonno, R.J., P.L. Callahan, D.M. Leippe, R.R. Rueckert, and J.E. Tomassini, "Inhibition of rhinovirus attachment by neutralizing monoclonal antibodies and their Fab fragments," J. Virol. 63(1):36–42 (Jan. 1989).

Colonno, R.J., "Cell surface receptors for picornaviruses", Bioassays 5(6):270–4 (1986).

Colonno, R.J., "Molecular interactions between human rhinoviruses and their cellular receptors", Seminars in Virol. 3(2):101–107 (1992).

Colonno, R.J., R.L. LaFemina, C.M. De Witt, and J.E. Tomassini, "The major–group rhinoviruses utilize the intercellular adhesion molecule 1 ligand as a cellular receptor during infection", in *New Aspects of Positive–Strand RNA Viruses,* Second International Symposium, Vienna, Austria, Meeting Date 1989, Brinton et al., eds. (Am. Soc. Microbiol., Washington, DC, 1990), pp. 257–261.

Colonno, R.J., G. Abraham, and J.E. Tomassini, "Molecular and biochemical aspects of human rhinovirus attachment to cellular receptors", in *Molecular Aspects of Picornavirus Infection and Detection,* [Presentations ICN–UCI Int. Conf. Virol.], Meeting Date 1988, Semler et al., eds. (Am. Soc. Microbiol., Washington, DC, 1989), pp. 169–178.

Colonno, R.J., J.E. Tomassini, P.L. Callahan, and W.J. Long, "Characterization of the cellular receptor specific for attachment of most human rhinovirus serotypes", in *Virus Attachment Entry Cells,* Proc. ASM Conf., Meeting Date 1985, Crowell et al., eds. (Am. Soc. Microbiol. Washington, DC, 1986), pp. 109–115.

Colonno, R.J., "Molecular interactions between human rhinoviruses and the adhesion receptor ICAM–1", in *Microb. Adhes. Invasion,* [Proc. Symp.], meeting date 1990, Hook et al., eds. (Springer, NY, 1992), pp. 33–41.

Colonno, R.J., J.H. Condra, and S. Mizutani, "Interaction of cellular receptors with the canyon structure of human rhinoviruses", in UCLA Symposia on Molecular and Cellular Biology New Series, vol. 90, *Cell Biology of Virus Entry, Replication, and Pathogenesis,* Taos, NM, Feb. 28–Mar. 5, 1988, Compans et al., eds. (Alan R. Liss, Inc., NY, 1988) pp. 75–84.

Colonno, R.J., R. B. Register, D.W. Lineberger, and C.R. Uncapher, "Identification of ICAM–1 residues critical for attachment of human rhinoviruses", Meeting on Molecular Biology of Human Pathogenic Viruses held at the 20$^{th}$ Annual Meeting of the Keystone Symposia on Molecular and Cellular Biology, Lake Tahoe, CA, Mar. 8–15, 1991, J. Cell Biochem. Suppl. 15(Part E):82, #M310 (1991).

Colonno, R.J., J.H. Condra, S. Mizutani, G. Abraham, P.L. Callahan, J.E. Tomassini, and M.A. Murcko, "Evidence for direct involvement of the rhinovirus canyon with cellular receptors", in *Symposium on Cell Biology of Virus Entry, Replication and Pathogenesis, Positive Strand RNA Viruses,* 17$^{th}$ Annual UCLA meeting on Molecular and Cellular Biology, Taos, NM, Feb. 28–Mar. 5, 1988, J. Cell. Biochem. Suppl., 0(12 Part C):4, #J005 (1988).

Colonno, R.J., J.E. Tomassini, and P.L. Callahan, "Isolation and characterization of a monoclonal antibody which blocks attachment of human rhinoviruses", in *UCLA Symposia on Molecular and Cellular Biology,* New Series, vol. 54, Positive Strand RNA Viruses, Keystone, CO Apr. 20–26, 1986, Brinton et al., eds. (Alan R. Liss, Inc., NY, 1987), pp. 93–102.

Colonno, R.J., J.E. Tomassini, and P.L. Callahn, "Human rhinovirus attachment requires a specific cellular receptor protein", in *Symposium on Positive Strand RNA Viruses,* 15$^{th}$ Annual Meeting of the UCLA Symposia on Molecular and Cellular Biology, Apr. 20–26, 1986, J. Cell Biochem Suppl., 0 (10 Part D):266, #Q4 (1986).

Condra, J.H., V.V. Sardan, J.E. Tomassini, A.J. Schlabach, M.–E. Davies, D.W. Lineberger, D.J. Graham, and R.J. Colonno,, "Bacterial expression of antibody fragments that block human rhinovirus infection of cultured cells", J. Biol. Chem. 265(4):2292–2295 (Feb. 1990).

Cordingley, M.G., P.L. Callahan, V.V. Sardana, V.M. Garsky, and R.J. Colonno, "Substrate requirements of human rhinovirus 3C protease for peptide cleavage in vitro", J. Biol. Chem. 265(16):9062–5 (1990).

Cordingley, M.G., R.B. Register, P.1. Callahan, V.M. Garsky, and R.J. Colonno, "Cleavage of small peptides in vitro by human rhinovirus 14 3C protease expressed in *Escherichia coli*", J. Virol. 63(12):5037–45 (Dec. 1989).

Dewalt, P.G., M.A. Lawson, R.J. Colonno, and B.L. Semler, "Chimeric picornavirus polyproteins demonstrate a common 3C proteinase substrate specificity", J. Virol. 63(8):3444–3452 (1989).

Dick, E.C., and C.R. Dick, "Natural and Experimental Infections of Nonhuman Primates with Respiratory Viruses", Laboratory Animal Science 24(1):177–181 (1974).

Emini, E.A., W.A. Schleif, R.J. Colonno, and E. Wimmer, "Antigenic conservation and divergence between the viral–specific proteins of poliovirus type 1 and various picornaviruses", Virol. 140(1):13–20 (1985).

Hazuda, D., V. Sardana, P. Callahan, M. Cordingley, and R. Colonno, "Chemical approaches to mapping the active site thiol of human rhinovirus 3C protease", Joint Meeting of the American Society for Biochemistry and Molecular Biology and the American Association of Immunologists, New Orleans, LA, Jun. 4–7, 1990, Fed. Am. Soc. Exp. Biol. J. 4(7):#1605 (1990).

Johnston, S.C., M.L. Dustin, M.L. Hibbs, and T.A. Springer, "On the species specificity of the interaction of LFA–1 with intercellular adhesion molecules", J. Immunol. 145(4):1181–1187 (Aug. 1990).

Lamarre, D., D.J. Capon, D.R. Karp, T.Gregory, E.O. Long, and R.–P. Sekaly, "Class II MHC molecules and the HIV envelope glycoprotein interact with functionally distinct regions of the molecule", EMBO J. 8(11):3271–3277 (1989).

Lineberger, D.W., C.R. Uncapher, D.J. Graham, and R.J. Colonno, "Domains 1 and 2 of ICAM–1 are sufficient to bind human rhinoviruses", Virus Research 24(2): 173–86 (1992).

Maddon, P.J., A.G. Dalgleish, J.S. McDougal, P.R. Clapham, R.A. Weiss, and R. Axel, "The T4 Gene Encodes the AIDS Virus Receptor and is Expressed in the Immune System and the Brain", Cell 47: 333–348 (Nov. 1986).

Mendelsohn, C.L., E. Wimmer, and V.R. Racaniello, "Cellular receptor for poliovirus: molecular cloning, nucleotide sequence, and expression of a new member of the immunoglobulin superfamily", Cell 56:855–865 (Mar. 1989).

Mizutani, S., and R.J. Colonno, In vitro synthesis of an infectious RNA from cDNA clones of human rhinovirus type 14:, J. Virol. 56(2):628–32 (Nov. 1985).

Register, R.B., C.R. Uncapher, A.M. Naylor, D.W. Lineberger, and R.J. Colonno, "Human–murine chimeras of ICAM–1 identify amino acid residues critical for rhinovirus and antibody binding", J. Virol. 65(12):6589–6596 (Dec. 1991).

Rueckert, R. B. Sherry, A. Mosser, R. Colonno, and M. Rossman, "Location of four neutralization antigens on the three–dimensional surface of a common–cold picornavirus, human rhinovirus 14", in *Virus Attachment Entry Cells*, Proc. ASM Conf., Meeting date 1985, Crowell et al., eds. (Am. Soc. Microbiol., Washington, DC, 1986, pp. 21–27.

Sherry, B., A.G. Mosser, R.J. Colonno, and R.R. Rueckert, "Use of monoclonal antibodies to identify four neutralizing immunogens on a common cold picornavirus, human rhinovirus 14", J. Virol. 57(1):246–57 (Jan. 1986).

Tomassini, J.E., T.R. Maxson, and R.J. Colonno, "Biochemical characterization of a glycoprotein required for rhinovirus attachment", J. Biol. Chem. 264(3):1656–1662 (Jan. 1989).

Tomassini, J.E., and R.J. Colonno, "Isolation and characterization of a cellular receptor involved in attachment of human rhinoviruses to cells", in *Symposium on Positive Strand RNA Viruses*, $15^{th}$ Annual Meeting of the UCLA Symposia on Molecular and Cellular Biology, Apr. 20–26, 1986, J. Cell. Biochem. Suppl., 0 (10 Part D):300, #Q92 (1986).

Braude, A. (ed.s), Infectious Diseases and Medical Microbiology, 2nd edition, W.B. Saunders Co., Philadelphia, PA, (1986) chapter 65 "Picornaviruses", pp. 521–529.

Gennaro, A.R. (ed.), Remington's Pharmaceutical Sciences, 18th edition, Mack Publishing Co., Easton, PA (1990), "Drug Absorption, Action and Disposition", pp. 707–721.

Martin et al., "Efficient Neutralization and Disruption of Rhinovirus by Chimeric ICAM–1/Immunoglobulin Molecules", J. Virology, 67(6):3561–3568 (Jun. 1993).

Hendley et al., "Transmission of Rhinovirus Colds By Self–Inoculation", The New England Journal of Medicine, 288(26):1361–1364 (Jun. 28, 1973).

Hendley, J. O., and Gwaltney, J. M., Jr., "Mechanisms of Transmission of Rhinovirus Infections", Epidemiologic Reviews, 10:242–257 (1988).

Suter, David, Associated Press, "Tests for a Nasal Spray to Deflect Cold Viruses", New York Times, Sep. 20, 1995.

Manning, Anita, "War on Bacteria Mix of Victories Amid Warnings", USA Today, Sep. 20, 1995.

Haney, Daniel Q., "Beyond Chicken Soup. Nasal Spray Keeps Chimps From Catching Cold Virus", St. Louis Post Dispatch, Sep. 20, 1995.

Associated Press, "Common Colds: Nasal Spray May Help Keep The Sniffles Away", Atlanta Constitution, Sep. 20, 1995.

Associated Press, "Drug Sprays Away Colds", New York Post, Sep. 20, 1995.

Haney, Daniel Q., Associated Press, "The Cold War: Scientists Develop Spray That May End Sniffles", Arizona Republic, Sep. 20, 1995.

Haney, Daniel Q., Associated Press, "For Colds, Nasal Spray Holds Hope. A Protein Swamps The Virus With Potential Targets In The Nose. Its a Decoy Trick", Philadelphia Inquirer, Sep. 20, 1995.

Associated Press, "Simple Nasal Spray May Be Able To Keep Common Cold Away. Medicine Successful On Chimps So Far", Washington Times, Sep. 20, 1995.

Associated Press, "Doctors Sniffing Out Spray to Fight Colds", Denver Post, Sep. 20, 1995.

Associated Press, "Someday Soon, A Simple Sniff Should Snuff The Sniffles", Houston Chronicle, Sep. 20, 1995.

Haney, Daniel Q., Associated Press, "Spray May Ward Off Sniffles. Nasal Treatment Studied To Keep Sniffles. Nasal Treatment Studied To Keep Cold Viruses From Invading Victim", Denver–Rocky Mountain News, Sep. 20, 1995.

Haney, Daniel Q., Associated Press, "Scientists Make Headway In Cold War With Nose Spray", Chicago Sun–Times, Sep. 20, 1995.

Haney, Daniel Q., Associated Press, "Labs Busy Working On Nose Spray To Keep Colds Away", Charlotte Observer, Sep. 20, 1995.

Associated Press, "Nasal Spray May Prevent Sniffles", Miami Herald, Sep. 20, 1995.

Associated Press, "Cure For The Cold? No, But Prevention May Be Spray Away", San Diego Union–Tribune, Sep. 20, 1995.

Haney, Daniel Q., "Nasal Spray Touted As Next–Best Thing To Cure For Colds", The Montreal Gazette, Sep. 20, 1995.

Associated Press, "Scientists Feel They Can Develop Spray To Keep The Sniffles Away", The Spectator, Sep. 20, 1995.

Haney, Daniel Q., Associated Press, "New Nasal Spray May Take Sniffles Out Of Common Cold", Cleveland Plain Dealer, Sep. 20, 1995.

Associated Press, No Cure, But Nothing To Sniff(le) At. Nasal Spray To Block Common Cold Is In The Works, Minneapolis Star Tribune, Sep. 20, 1995.

Haney, Daniel Q., Associated Press, "Out Front: Progress On Cold Front. Spray May Ward Off Sniffles. Medicine Is First To Block Infection", Sep. 19, 1995.

Monitoring Report, "Cure For Colds Sep. 18 to Sep. 20", Video Monitoring Services of America, a Burrelle's Affiliate, New York, New York, pp. 1–3, Sep. 20, 1995.

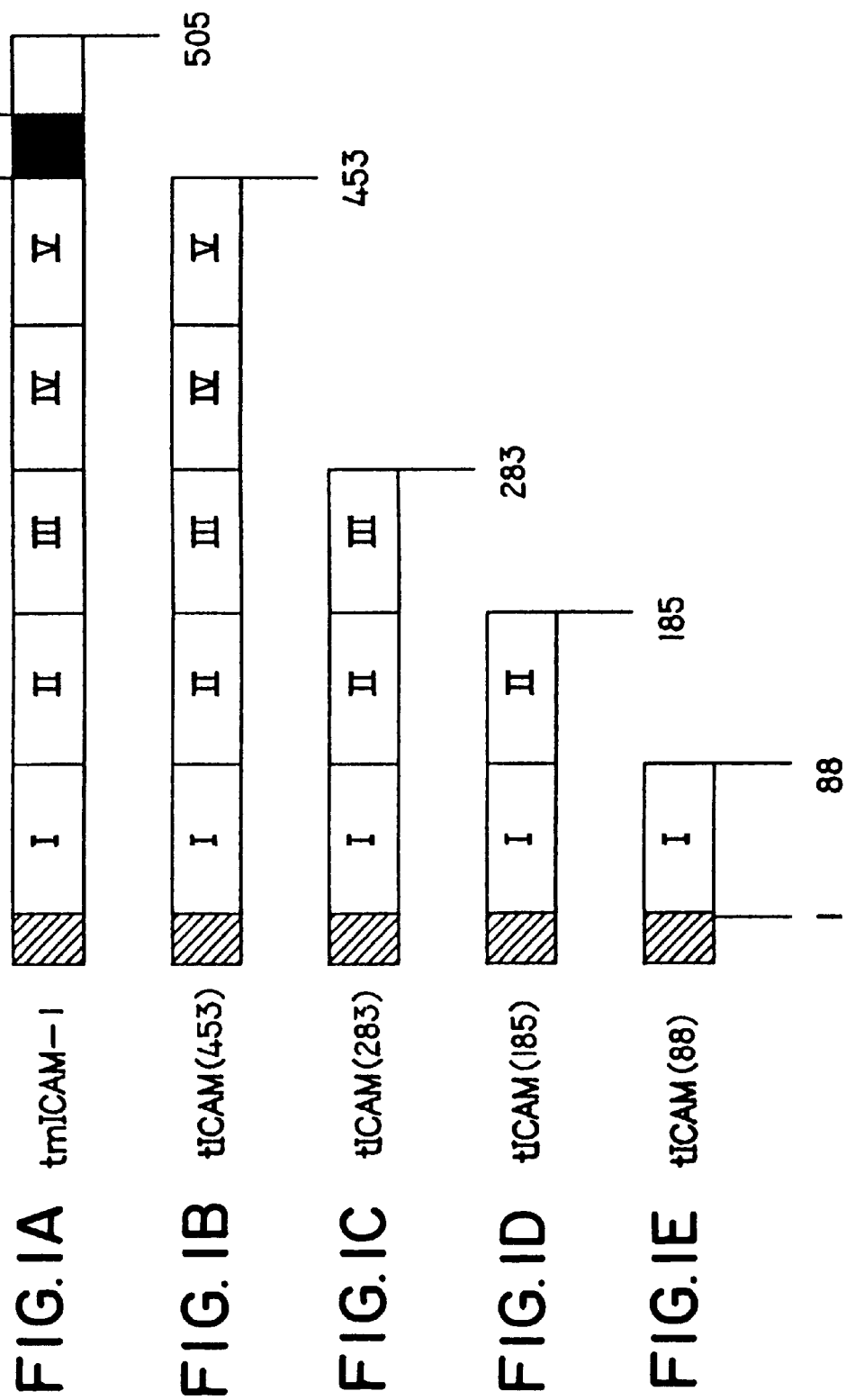

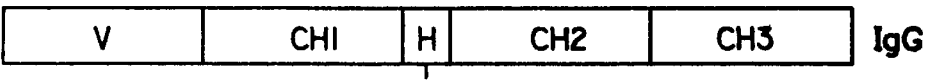
FIG.2A
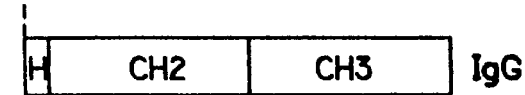
216  FIG.2B
FIG.2C  185
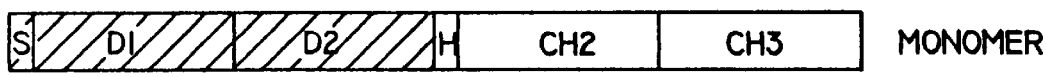
FIG.2D
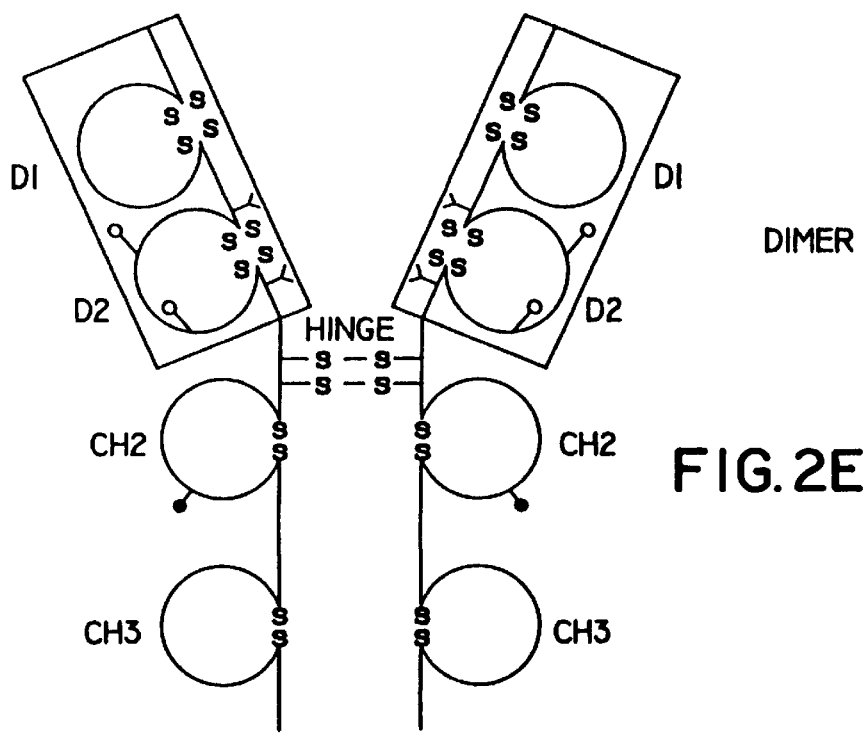
FIG.2E

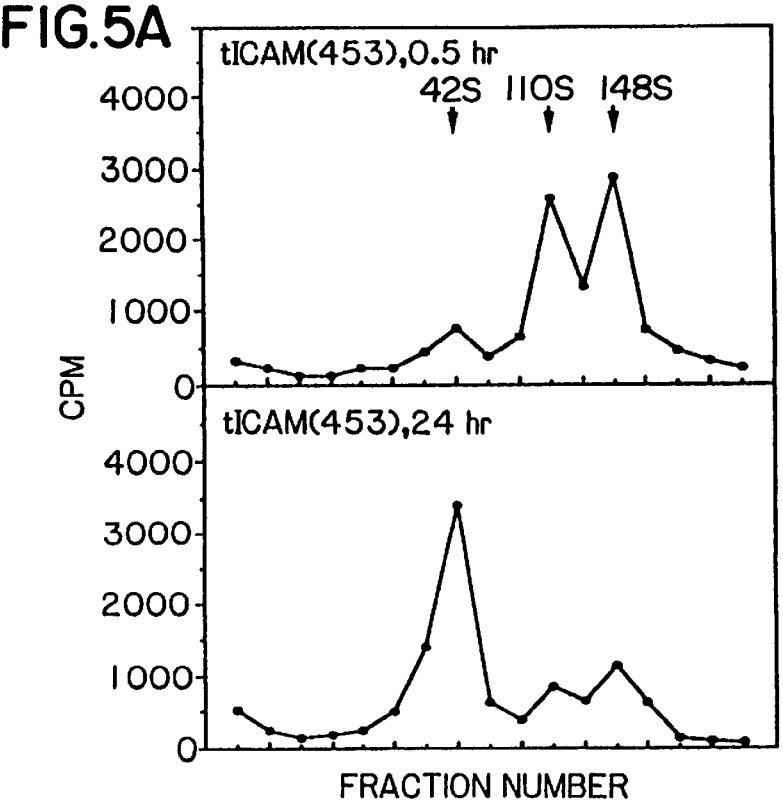
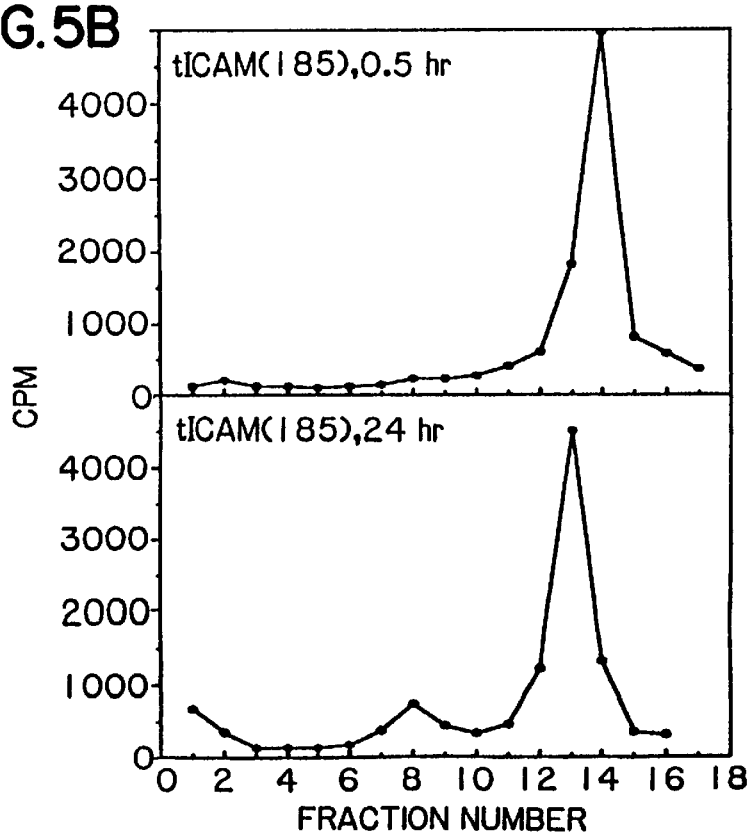

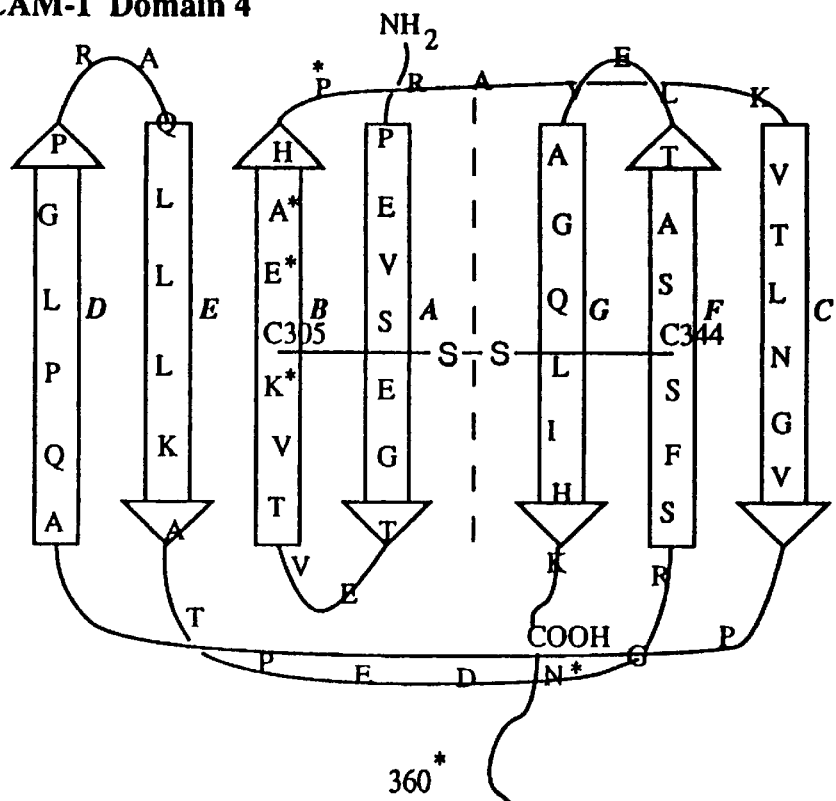
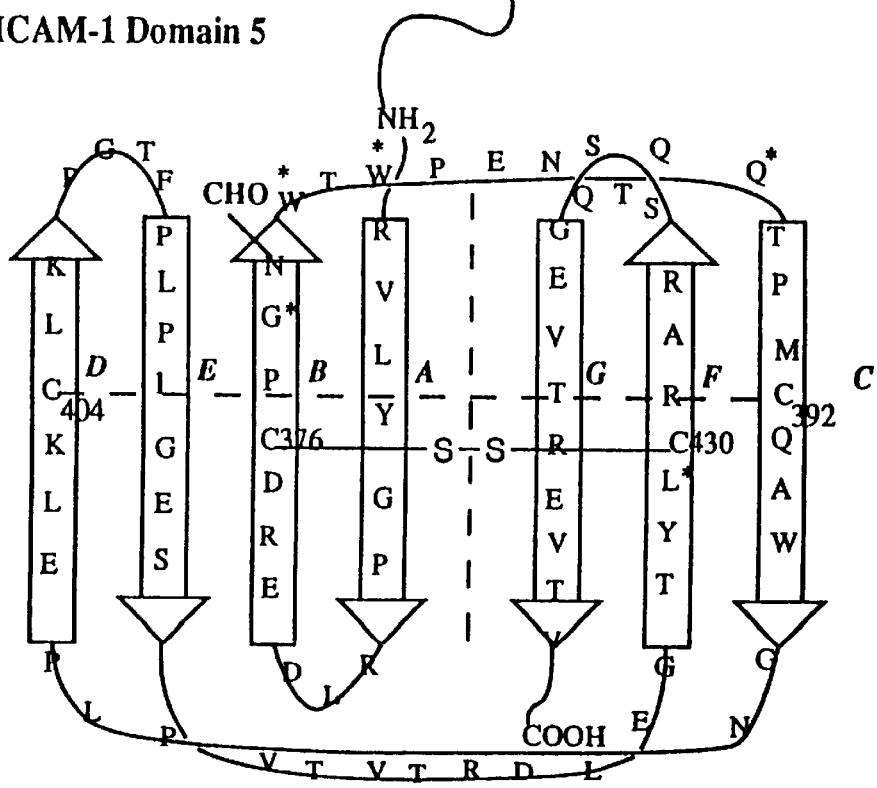
FIG. 6

```
                           SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
         (A) LENGTH: 31
         (B) TYPE: nucleic acid
         (C) STRANDEDNESS: single
         (D) TOPOLOGY: linear (ii) MOLECULE TYPE: other nucleic acid (iii) HYPOTHETICAL: no (iv) ANTI-SENSE: no (ix) FEATURE:
         (A) NAME/KEY: PCR 5.1 (5' PCR primer)
         (B) LOCATION: 5' end of ICAM-1 coding sequence
         (D) OTHER INFORMATION: bp 1 = G; bp 2-7 = EcoRI site;
             bp 8-31 = 24 bases coding for the first eight
             amino acid residues of hICAM-1

(x) PUBLICATION INFORMATION:
         (A) AUTHORS: Greve, J.M., G. Davis, A.M. Meyer, C.P.
             Forte, S.C. Yost, C.W. Marlor, M.E. Kamarck, and
             A. McClelland
         (B) TITLE: The Major Human Rhinovirus Receptor is
             ICAM-1
         (C) JOURNAL: Cell
         (D) VOLUME: 56
         (F) PAGES: 839-847
         (G) DATE: March 10, 1989
         (K) RELEVANT RESIDUES IN SEQ ID NO:1: From 1 to 31

(xi) SEQUENCE DESCRIPTION: SEQ ID NO:1:

GGAATTC ATG GCT CCC AGC AGC CCC CGG CCC                              31
        Met Ala Pro Ser Ser Pro Arg Pro
                        5

(2) INFORMATION FOR SEQ ID NO:2:

(i) SEQUENCE CHARACTERISTICS:
         (A) LENGTH: 31 bp
         (B) TYPE: nucleic acid
         (C) STRANDEDNESS: single
         (D) TOPOLOGY: linear (ii) MOLECULE TYPE: other nucleic acid (iii) HYPOTHETICAL: no (iv) ANTI-SENSE: yes (ix) FEATURE:
         (A) NAME/KEY: PCR 3.1 (3' PCR primer)
         (B) LOCATION: 3' end of ICAM-1 coding sequence
         (D) OTHER INFORMATION: bp 1 = G; bp 2-7 = EcoRI site;
             bp 8-31 = 24 bases complementary to nucleic acid
             sequence coding for last 8 amino acid residues of
             hICAM-1
```

```
    (x) PUBLICATION INFORMATION:
         (A) AUTHORS: Greve, J.M., G. Davis, A.M. Meyer, C.P.
               Forte, S.C. Yost, C.W. Marlor, M.E. Kamarck, and
               A. McClelland
         (B) TITLE: The Major Human Rhinovirus Receptor is
               ICAM-1
         (C) JOURNAL: Cell
         (D) VOLUME: 56
         (F) PAGES: 839-847
         (G) DATE: March 10, 1989
         (K) RELEVANT RESIDUES IN SEQ ID NO:2: From 1 to 31

(xi) SEQUENCE DESCRIPTION: SEQ ID NO:2:

GGAATTCTCA GGGAGGCGTG GCTTGTGTGT T                                       31

(2) INFORMATION FOR SEQ ID NO:3:

(i) SEQUENCE CHARACTERISTICS:
         (A) LENGTH: 47 bp
         (B) TYPE: nucleic acid
         (C) STRANDEDNESS: single
         (D) TOPOLOGY: linear (ii) MOLECULE TYPE: other nucleic acid (iii) HYPOTHETICAL: no (iv) ANTI-SENSE: yes (ix) FEATURE:
         (A) NAME/KEY: ICAM1 probe
         (D) OTHER INFORMATION: complementary to nucleotides
               565 to 611 of ICAM-1

(x) PUBLICATION INFORMATION:
         (A) AUTHORS: Greve, J.M., G. Davis, A.M. Meyer, C.P.
               Forte, S.C. Yost, C.W. Marlor, M.E. Kamarck, and
               A. McClelland
         (B) TITLE: The Major Human Rhinovirus Receptor is
               ICAM-1
         (C) JOURNAL: Cell
         (D) VOLUME: 56
         (F) PAGES: 839-847
         (G) DATE: March 10, 1989
         (K) RELEVANT RESIDUES IN SEQ ID NO:3: From 1 to 47

(xi) SEQUENCE DESCRIPTION: SEQ ID NO:3:

GAGGTGTTCT CAAACAGCTC CAGCCCTTGG GGCCGCAGGT CCAGTTC                       47

(2) INFORMATION FOR SEQ ID NO:4:

(i) SEQUENCE CHARACTERISTICS:
         (A) LENGTH: 47 bp
         (B) TYPE: nucleic acid
         (C) STRANDEDNESS: single
         (D) TOPOLOGY: linear (ii) MOLECULE TYPE: other nucleic acid (iii) HYPOTHETICAL: no (iv) ANTI-SENSE: yes (ix) FEATURE:
         (A) NAME/KEY: ICAM3 probe
         (B) LOCATION: complementary to nucleotides 659 to 705
               of human ICAM-1

(xi) SEQUENCE DESCRIPTION: SEQ ID NO:4:

CGCTGGCAGG ACAAAGGTCT GGAGCTGGTA GGGGGCCGAG GTGTTCT                       47

(2) INFORMATION FOR SEQ ID NO:5:
```

(i) SEQUENCE CHARACTERISTICS:
        (A) LENGTH: 49 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: PCR 5.5
        (D) OTHER INFORMATION: bp 1 = G; bp 2-7 = EcoRI site;
            bp 8-13 = HindIII site; bp 14-25 = hICAM-1 5'
            untranslated region; bp 26-49 = sequence coding
            for first 8 amino acid residues of hICAM-1

(x) PUBLICATION INFORMATION:
        (A) AUTHORS: Greve, J.M., C.P. Forte, C.W. Marlor,
            A.M. Meyer, H. Hoover-Litty, D. Wunderlich, and A.
            McClelland
        (B) TITLE: "Mechanisms of Receptor-mediated Rhinovirus
            Neutralization Defined by Two Soluble Forms of
            ICAM-1"
        (C) JOURNAL: Journal of Virology
        (D) VOLUME: 65
        (E) ISSUE: 11
        (F) PAGES: 6015-6023
        (G) DATE: 1991
        (K) RELEVANT RESIDUES IN SEQ ID NO:5: From 1 to 49

(xi) SEQUENCE DESCRIPTION: SEQ ID NO:5:

GGAATTCAAG CTTCTCAGCC TCGCT ATG GCT CCC AGC AGC CCC CGG CCC                49
                           Met Ala Pro Ser Ser Pro Arg Pro
                                         5

(2) INFORMATION FOR SEQ ID NO:6:

(i) SEQUENCE CHARACTERISTICS:
        (A) LENGTH: 40 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: PCR 3.3
        (D) OTHER INFORMATION: bp 1 = G; bp 2-7 = EcoRI site;
            bp 8-13 = PstI site; bp 14-16 = stop codon; bp 17-
            40 = complementary to nucleotide sequence coding
            for residues 453-446 of hICAM-1

(x) PUBLICATION INFORMATION:
        (A) AUTHORS: Greve, J.M., C.P. Forte, C.W. Marlor,
            A.M. Meyer, H. Hoover-Litty, D. Wunderlich, and A.
            McClelland
        (B) TITLE: Mechanisms of Receptor-mediated Rhinovirus
            Neutralization Defined by Two Soluble Forms of
            ICAM-1
        (C) JOURNAL: Journal of Virology
        (D) VOLUME: 65
        (E) ISSUE: 11
        (F) PAGES: 6015-6023
        (G) DATE: 1991
        (K) RELEVANT RESIDUES IN SEQ ID NO:6: From 1 to 40

(xi) SEQUENCE DESCRIPTION: SEQ ID NO:6:

GGAATTCCTG CAGTCACTCA TACCGGGGGG AGAGCACATT                                 40

(2) INFORMATION FOR SEQ ID NO:7:

(i) SEQUENCE CHARACTERISTICS:
        (A) LENGTH: 39 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: PCR 3.10
        (D) OTHER INFORMATION: bp 1 = T; bp 2-7 = Xba site; bp
            8-13 = Bam site; bp 14-16 = stop codon; bp 17-39 =
            sequence complementary to nucleotides 693-671
            which code for amino acid residues 185-178 of
            hICAM-1

(x) PUBLICATION INFORMATION:
        (A) AUTHORS: Greve, J.M., C.P. Forte, C.W. Marlor,
            A.M. Meyer, H. Hoover-Litty, D. Wunderlich, and A.
            McClelland
        (B) TITLE: Mechanisms of Receptor-mediated Rhinovirus
            Neutralization Defined by Two Soluble Forms of
            ICAM-1
        (C) JOURNAL: Journal of Virology
        (D) VOLUME: 65
        (E) ISSUE: 11
        (F) PAGES: 6015-6023
        (G) DATE: 1991
        (K) RELEVANT RESIDUES IN SEQ ID NO:7: From 1 to 39

(xi) SEQUENCE DESCRIPTION: SEQ ID NO:7:

TTCTAGAGGA TCCTCAAAAG GTCTGGAGCT GGTAGGGGG                                      39

(2) INFORMATION FOR SEQ ID NO:8:

(i) SEQUENCE CHARACTERISTICS:
        (A) LENGTH: 43 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: PCR 3.19
        (D) OTHER INFORMATION: bp 1 = T; bp 2-7 = Xba site; bp
            8-13 = Bam site; bp 14-16 = stop codon; bp 17-19 =
            lysine codon; bp 20 - 43 = sequence complementary
            to nucleotides coding for amino acid residues 453-
            446 of hICAM-1

(xi) SEQUENCE DESCRIPTION: SEQ ID NO:8:

TTCTAGAGGA TCCTCACTTC TCATACCGGG GGGAGAGCAC ATT                              43

(2) INFORMATION FOR SEQ ID NO:9:

(i) SEQUENCE CHARACTERISTICS:
        (A) LENGTH: 43 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: PCR 3.20
        (D) OTHER INFORMATION: bp 1 = T; bp 2-7 = Xba site; bp
            8-13 = Bam site; bp 14-16 = stop codon; bp 17-19 =
            lysine codon; bp 20 - 43 = sequence complementary
            to nucleotides coding for amino acid residues 185-
            178 of hICAM-1

(xi) SEQUENCE DESCRIPTION: SEQ ID NO:9:

TTCTAGAGGA TCCTCACTTA AAGGTCTGGA GCTGGTAGGG GGC                43

(2) INFORMATION FOR SEQ ID NO:10:

(i) SEQUENCE CHARACTERISTICS:
        (A) LENGTH: 48 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: 3' PCR primer for tICAM(185)/IgG chimera
        (D) OTHER INFORMATION: bp 1-24 = complementary to
            nucleotides coding for amino acid residues 216-223
            of human IgG1 heavy chain; bp 25-48 =
            complementary to last 24 bases of nucleotide
            sequence coding for tICAM(185)

(xi) SEQUENCE DESCRIPTION: SEQ ID NO:10:

CGGTGGGCAT GTGTGAGTTT TGTCAAAGGT CTGGAGCTGG TAGGGGGC          48

(2) INFORMATION FOR SEQ ID NO:11:

(i) SEQUENCE CHARACTERISTICS:
        (A) LENGTH: 24 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: 5' PCR primer for IgG fragment
        (D) OTHER INFORMATION: coding for residues 216-223 of
            human IgG1 heavy chain (xi) SEQUENCE DESCRIPTION: SEQ ID NO:11:

GAC AAA ACT CAC ACA TGC CCA CGG                               24
Asp Lys Thr His Thr Ser Pro Arg
                5

(2) INFORMATION FOR SEQ ID NO:12:

(i) SEQUENCE CHARACTERISTICS:
        (A) LENGTH: 40 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
            (A) NAME/KEY: 3' PCR primer for IgG fragment
            (D) OTHER INFORMATION: bp 1 = G; bp 2-7 = Bam site; bp
                8-13 = Xba site; bp 14-16 = stop codon; bp 17-40 =
                sequence complementary to last 8 residues of human
                IgG1 heavy chain (xi) SEQUENCE DESCRIPTION: SEQ ID NO:12:

GGGATTCTCT AGATCATTTA CCCGGAGACA GGGAGAGGCT                                40

(2) INFORMATION FOR SEQ ID NO:13:

(i) SEQUENCE CHARACTERISTICS:
            (A) LENGTH: 48 bp
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (ix) FEATURE:
            (A) NAME/KEY: 3' PCR primer for the construction of
                tICAM(453)/IgG chimera
            (D) OTHER INFORMATION: bp 1-24 = complementary to
                nucleotides coding for amino acid residues 216-223
                of human IgG1 heavy chain; bp 25-48 =
                complementary to nucleotide sequence coding for
                amino acid residues 446-453 of tICAM(453)

(xi) SEQUENCE DESCRIPTION: SEQ ID NO:13:

CGGTGGGCAT GTGTGAGTTT TGTCCTCATA CCGGGGGGAG AGCACATT                       48

(2) INFORMATION FOR SEQ ID NO:14:

(i) SEQUENCE CHARACTERISTICS:
            (A) LENGTH: 2043 bp
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: no (ix) FEATURE:
            (A) NAME/KEY: tICAM(453)/IgG fusion
            (D) OTHER INFORMATION: bp 1-1359 = nucleotides coding
                for amino acid residues 1-453 of ICAM-1; bp 1360-
                2040 = nucleotides coding for amino acid residues
                216-442 of human heavy chain IgG1; bp 2401-2043 =
                stop codon (xi) SEQUENCE DESCRIPTION: SEQ ID NO:14:

CAG ACA TCT GTG TCC CCC TCA AAA GTC ATC CTG CCC CGG GGA GGC                45
Gln Thr Ser Val Ser Pro Ser Lys Val Ile Leu Pro Arg Gly Gly
                5                  10                 15

TCC GTG CTG GTG ACA TGC AGC ACC TCC TGT GAC CAG CCC AAG TTG                90
Ser Val Leu Val Thr Cys Ser Thr Ser Cys Asp Gln Pro Lys Leu
            20                  25                  30

TTG GGC ATA GAG ACC CCG TTG CCT AAA AAG GAG TTG CTC CTG CCT               135
Leu Gly Ile Glu Thr Pro Leu Pro Lys Lys Glu Leu Leu Leu Pro

-continued

|  |  |  | 35 |  |  |  | 40 |  |  |  | 45 |  |  |  |
|---|---|---|---|---|---|---|---|---|---|---|---|---|---|---|
| GGG | AAC | AAC | CGG | AAG | GTG | TAT | GAA | CTG | AGC | AAT | GTG | CAA | GAA | GAT | 180 |
| Gly | Asn | Asn | Arg | Lys | Val | Tyr | Glu | Leu | Ser | Asn | Val | Gln | Glu | Asp |  |
|  |  |  | 50 |  |  |  | 55 |  |  |  | 60 |  |  |  |  |
| AGC | CAA | CCA | ATG | TGC | TAT | TCA | AAC | TGC | CCT | GAT | GGG | CAG | TCA | ACA | 225 |
| Ser | Gln | Pro | Met | Cys | Tyr | Ser | Asn | Cys | Pro | Asp | Gly | Gln | Ser | Thr |  |
|  |  |  | 65 |  |  |  | 70 |  |  |  | 75 |  |  |  |  |
| GCT | AAA | ACC | TTC | CTC | ACC | GTG | TAC | TGG | ACT | CCA | GAA | CGG | GTG | GAA | 270 |
| Ala | Lys | Thr | Phe | Leu | Thr | Val | Tyr | Trp | Thr | Pro | Glu | Arg | Val | Glu |  |
|  |  |  | 80 |  |  |  | 85 |  |  |  | 90 |  |  |  |  |
| CTG | GCA | CCC | CTC | CCC | TCT | TGG | CAG | CCA | GTG | GGC | AAG | AAC | CTT | ACC | 315 |
| Leu | Ala | Pro | Leu | Pro | Ser | Trp | Gln | Pro | Val | Gly | Lys | Asn | Leu | Thr |  |
|  |  |  | 95 |  |  |  | 100 |  |  |  | 105 |  |  |  |  |
| CTA | CGC | TGC | CAG | GTG | GAG | GGT | GGG | GCA | CCC | CGG | GCC | AAC | CTC | ACC | 360 |
| Leu | Arg | Cys | Gln | Val | Glu | Gly | Gly | Ala | Pro | Arg | Ala | Asn | Leu | Thr |  |
|  |  |  | 110 |  |  |  | 115 |  |  |  | 120 |  |  |  |  |
| GTG | GTG | CTG | CTC | CGT | GGG | GAG | AAG | GAG | CTG | AAA | CGG | GAG | CCA | GCT | 405 |
| Val | Val | Leu | Leu | Arg | Gly | Glu | Lys | Glu | Leu | Lys | Arg | Glu | Pro | Ala |  |
|  |  |  | 125 |  |  |  | 130 |  |  |  | 135 |  |  |  |  |
| GTG | GGG | GAG | CCC | GCT | GAG | GTC | ACG | ACC | ACG | GTG | CTG | GTG | AGG | AGA | 450 |
| Val | Gly | Glu | Pro | Ala | Glu | Val | Thr | Thr | Thr | Val | Leu | Val | Arg | Arg |  |
|  |  |  | 140 |  |  |  | 145 |  |  |  | 150 |  |  |  |  |
| GAT | CAC | CAT | GGA | GCC | AAT | TTC | TCG | TGC | CGC | ACT | GAA | CTG | GAC | CTG | 495 |
| Asp | His | His | Gly | Ala | Asn | Phe | Ser | Cys | Arg | Thr | Glu | Leu | Asp | Leu |  |
|  |  |  | 155 |  |  |  | 160 |  |  |  | 165 |  |  |  |  |
| CGG | CCC | CAA | GGG | CTG | GAG | CTG | TTT | GAG | AAC | ACC | TCG | GCC | CCC | TAC | 540 |
| Arg | Pro | Gln | Gly | Leu | Glu | Leu | Phe | Glu | Asn | Thr | Ser | Ala | Pro | Tyr |  |
|  |  |  | 170 |  |  |  | 175 |  |  |  | 180 |  |  |  |  |
| CAG | CTC | CAG | ACC | TTT | GTC | CTG | CCA | GCG | ACT | CCC | CCA | CAA | CTT | GTC | 585 |
| Gln | Leu | Gln | Thr | Phe | Val | Leu | Pro | Ala | Thr | Pro | Pro | Gln | Leu | Val |  |
|  |  |  | 185 |  |  |  | 190 |  |  |  | 195 |  |  |  |  |
| AGC | CCC | CGG | GTC | CTA | GAG | GTG | GAC | ACG | CAG | GGG | ACC | GTG | GTC | TGT | 630 |
| Ser | Pro | Arg | Val | Leu | Glu | Val | Asp | Thr | Gln | Gly | Thr | Val | Val | Cys |  |
|  |  |  | 200 |  |  |  | 205 |  |  |  | 210 |  |  |  |  |
| TCC | CTG | GAC | GGG | CTG | TTC | CCA | GTC | TCG | GAG | GCC | CAG | GTC | CAC | CTG | 675 |
| Ser | Leu | Asp | Gly | Leu | Phe | Pro | Val | Ser | Glu | Ala | Gln | Val | His | Leu |  |
|  |  |  | 215 |  |  |  | 220 |  |  |  | 225 |  |  |  |  |
| GCA | CTG | GGG | GAC | CAG | AGG | TTG | AAC | CCC | ACA | GTC | ACC | TAT | GGC | AAC | 720 |
| Ala | Leu | Gly | Asp | Gln | Arg | Leu | Asn | Pro | Thr | Val | Thr | Tyr | Gly | Asn |  |
|  |  |  | 230 |  |  |  | 235 |  |  |  | 240 |  |  |  |  |
| GAC | TCC | TTC | TCG | GCC | AAG | GCC | TCA | GTC | AGT | GTG | ACC | GCA | GAG | GAC | 765 |
| Asp | Ser | Phe | Ser | Ala | Lys | Ala | Ser | Val | Ser | Val | Thr | Ala | Glu | Asp |  |
|  |  |  | 245 |  |  |  | 250 |  |  |  | 255 |  |  |  |  |
| GAG | GGC | ACC | CAG | CGG | CTG | ACG | TGT | GCA | GTA | ATA | CTG | GGG | AAC | CAG | 810 |
| Glu | Gly | Thr | Gln | Arg | Leu | Thr | Cys | Ala | Val | Ile | Leu | Gly | Asn | Gln |  |
|  |  |  | 260 |  |  |  | 265 |  |  |  | 270 |  |  |  |  |
| AGC | CAG | GAG | ACA | CTG | CAG | ACA | GTG | ACC | ATC | TAC | AGC | TTT | CCG | GCG | 855 |
| Ser | Gln | Glu | Thr | Leu | Gln | Thr | Val | Thr | Ile | Tyr | Ser | Phe | Pro | Ala |  |
|  |  |  | 275 |  |  |  | 280 |  |  |  | 285 |  |  |  |  |
| CCC | AAC | GTG | ATT | CTG | ACG | AAG | CCA | GAG | GTC | TCA | GAA | GGG | ACC | GAG | 900 |
| Pro | Asn | Val | Ile | Leu | Thr | Lys | Pro | Glu | Val | Ser | Glu | Gly | Thr | Glu |  |
|  |  |  | 290 |  |  |  | 295 |  |  |  | 300 |  |  |  |  |
| GTG | ACA | GTG | AAG | TGT | GAG | GCC | CAC | CCT | AGA | GCC | AAG | GTG | ACG | CTG | 945 |
| Val | Thr | Val | Lys | Cys | Glu | Ala | His | Pro | Arg | Ala | Lys | Val | Thr | Leu |  |
|  |  |  | 305 |  |  |  | 310 |  |  |  | 315 |  |  |  |  |
| AAT | GGG | GTT | CCA | GCC | CAG | CCA | CTG | GGC | CCG | AGG | GCC | CAG | CTC | CTG | 990 |
| Asn | Gly | Val | Pro | Ala | Gln | Pro | Leu | Gly | Pro | Arg | Ala | Gln | Leu | Leu |  |
|  |  |  | 320 |  |  |  | 325 |  |  |  | 330 |  |  |  |  |
| CTG | AAG | GCC | ACC | CCA | GAG | GAC | AAC | GGG | CGC | AGC | TTC | TCC | TGC | TCT | 1035 |

-continued

```
Leu Lys Ala Thr Pro Glu Asp Asn Gly Arg Ser Phe Ser Cys Ser
        335                 340                 345

GCA ACC CTG GAG GTG GCC GGC CAG CTT ATA CAC AAG AAC CAG ACC      1080
Ala Thr Leu Glu Val Ala Gly Gln Leu Ile His Lys Asn Gln Thr
        350                 355                 360

CGG GAG CTT CGT GTC CTG TAT GGC CCC CGA CTG GAC GAG AGG GAT      1125
Arg Glu Leu Arg Val Leu Tyr Gly Pro Arg Leu Asp Glu Arg Asp
        365                 370                 375

TGT CCG GGA AAC TGG ACG TGG CCA GAA AAT TCC CAG CAG ACT CCA      1170
Cys Pro Gly Asn Trp Thr Trp Pro Glu Asn Ser Gln Gln Thr Pro
        380                 385                 390

ATG TGC CAG GCT TGG GGG AAC CCA TTG CCC GAG CTC AAG TGT CTA      1215
Met Cys Gln Ala Trp Gly Asn Pro Leu Pro Glu Leu Lys Cys Leu
        395                 400                 405

AAG GAT GGC ACT TTC CCA CTG CCC ATC GGG GAA TCA GTG ACT GTC      1260
Lys Asp Gly Thr Phe Pro Leu Pro Ile Gly Glu Ser Val Thr Val
        410                 415                 420

ACT CGA GAT CTT GAG GGC ACC TAC CTC TGT CGG GCC AGG AGC ACT      1305
Thr Arg Asp Leu Glu Gly Thr Tyr Leu Cys Arg Ala Arg Ser Thr
        425                 430                 435

CAA GGG GAG GTC ACC CGC AAG GTG ACC GTG AAT GTG CTC TCC CCC      1350
Gln Gly Glu Val Thr Arg Lys Val Thr Val Asn Val Leu Ser Pro
        440                 445                 450

CGG TAT GAG GAC AAA ACT CAC ACA TGC CCA CCG TGC CCA GCA CCT      1395
Arg Tyr Glu Asp Lys Thr His Thr Cys Pro Pro Cys Pro Ala Pro
        455                 460                 465

GAA CTC CTG GGG GGA CCG TCA GTC TTC CTC TTC CCC CCA AAA CCC      1440
Glu Leu Leu Gly Gly Pro Ser Val Phe Leu Phe Pro Pro Lys Pro
        470                 475                 480

AAG GAC ACC CTC ATG ATC TCC CGG ACC CCT GAG GTC ACA TGC GTG      1485
Lys Asp Thr Leu Met Ile Ser Arg Thr Pro Glu Val Thr Cys Val
        485                 490                 495

GTG GTG GAC GTG AGC CAC GAA GAC CCT GAG GTC AAG TTC AAC TGG      1530
Val Val Asp Val Ser His Glu Asp Pro Glu Val Lys Phe Asn Trp
        500                 505                 510

TAC GTG GAC GGC GTG GAG GTG CAT AAT GCC AAG ACA AAG CCG CGG      1575
Tyr Val Asp Gly Val Glu Val His Asn Ala Lys Thr Lys Pro Arg
        515                 520                 525

GAG GAG CAG TAC AAC AGC ACG TAC CGG GTG GTC AGC GTC CTC ACC      1620
Glu Glu Gln Tyr Asn Ser Thr Tyr Arg Val Val Ser Val Leu Thr
        530                 535                 540

GTC CTG CAC CAG GAC TGG CTG AAT GGC AAG GAG TAC AAG TGC AAG      1665
Val Leu His Gln Asp Trp Leu Asn Gly Lys Glu Tyr Lys Cys Lys
        545                 550                 555

GTC TCC AAC AAA GCC CTC CCA GCC CCC ATC GAG AAA ACC ATC TCC      1710
Val Ser Asn Lys Ala Leu Pro Ala Pro Ile Glu Lys Thr Ile Ser
        560                 565                 570

AAA GCC AAA GGG CAG CCC CGA GAA CCA CAG GTG TAC ACC CTG CCC      1755
Lys Ala Lys Gly Gln Pro Arg Glu Pro Gln Val Tyr Thr Leu Pro
        575                 580                 585

CCA TCC CGG GAT GAG CTG ACC AAG AAC CAG GTC AGC CTG ACC TGC      1800
Pro Ser Arg Asp Glu Leu Thr Lys Asn Gln Val Ser Leu Thr Cys
        590                 595                 600

CTG GTC AAA GGC TTC TAT CCC AGC GAC ATC GCC GTG GAG TGG GAG      1845
Leu Val Lys Gly Phe Tyr Pro Ser Asp Ile Ala Val Glu Trp Glu
        605                 610                 615

AGC AAT GGG CAG CCG GAG AAC AAC TAC AAG ACC ACG CCT CCC GTG      1890
Ser Asn Gly Gln Pro Glu Asn Asn Tyr Lys Thr Thr Pro Pro Val
        620                 625                 630
```

```
CTG GAC TCC GAC GGC TCC TTC TTC CTC TAC AGC AAG CTC ACC GTG              1935
Leu Asp Ser Asp Gly Ser Phe Phe Leu Tyr Ser Lys Leu Thr Val
            635                 640                 645

GAC AAG AGC AGG TGG CAG CAG GGG AAC GTC TTC TCA TGC TCC GTG              1980
Asp Lys Ser Arg Trp Gln Gln Gly Asn Val Phe Ser Cys Ser Val
            650                 655                 660

ATG CAT GAG GCT CTG CAC AAC CAC TAC ACG CAG AAG AGC CTC TCC              2025
Met His Glu Ala Leu His Asn His Tyr Thr Gln Lys Ser Leu Ser
            665                 670                 675

CTG TCT CCG GGT AAA TGA                                                  2043
Leu Ser Pro Gly Lys
            680
```

(2) INFORMATION FOR SEQ ID NO:15:

(i) SEQUENCE CHARACTERISTICS:
        (A) LENGTH: 680 amino acid residues
        (B) TYPE: amino acids
        (C) TOPOLOGY: linear (ii) MOLECULE TYPE:
        (A) DESCRIPTION: protein (iii) HYPOTHETICAL: no (v) FRAGMENT TYPE: complete sequence (ix) FEATURE:
        (A) NAME/KEY: tICAM(185)/IgG fusion protein
        (D) OTHER INFORMATION: amino acid residues 1-453 =
            tICAM(453); amino acid residues 454-680 = amino
            acid residues 216-442 of human IgG1 heavy chain (xi) SEQUENCE DESCRIPTION: SEQ ID NO:15:

```
Gln Thr Ser Val Ser Pro Ser Lys Val Ile Leu Pro Arg Gly Gly
                5                  10                  15

Ser Val Leu Val Thr Cys Ser Thr Ser Cys Asp Gln Pro Lys Leu
                20                 25                  30

Leu Gly Ile Glu Thr Pro Leu Pro Lys Lys Glu Leu Leu Leu Pro
                35                 40                  45

Gly Asn Asn Arg Lys Val Tyr Glu Leu Ser Asn Val Gln Glu Asp
                50                 55                  60

Ser Gln Pro Met Cys Tyr Ser Asn Cys Pro Asp Gly Gln Ser Thr
                65                 70                  75

Ala Lys Thr Phe Leu Thr Val Tyr Trp Thr Pro Glu Arg Val Glu
                80                 85                  90

Leu Ala Pro Leu Pro Ser Trp Gln Pro Val Gly Lys Asn Leu Thr
                95                 100                 105

Leu Arg Cys Gln Val Glu Gly Gly Ala Pro Arg Ala Asn Leu Thr
                110                115                 120

Val Val Leu Leu Arg Gly Glu Lys Glu Leu Lys Arg Glu Pro Ala
                125                130                 135

Val Gly Glu Pro Ala Glu Val Thr Thr Thr Val Leu Val Arg Arg
                140                145                 150

Asp His His Gly Ala Asn Phe Ser Cys Arg Thr Glu Leu Asp Leu
                155                160                 165

Arg Pro Gln Gly Leu Glu Leu Phe Glu Asn Thr Ser Ala Pro Tyr
                170                175                 180

Gln Leu Gln Thr Phe Val Leu Pro Ala Thr Pro Pro Gln Leu Val
                185                190                 195

Ser Pro Arg Val Leu Glu Val Asp Thr Gln Gly Thr Val Val Cys
```

```
                    200                 205                 210
Ser Leu Asp Gly Leu Phe Pro Val Ser Glu Ala Gln Val His Leu
                215                 220                 225

Ala Leu Gly Asp Gln Arg Leu Asn Pro Thr Val Thr Tyr Gly Asn
                230                 235                 240

Asp Ser Phe Ser Ala Lys Ala Ser Val Ser Val Thr Ala Glu Asp
                245                 250                 255

Glu Gly Thr Gln Arg Leu Thr Cys Ala Val Ile Leu Gly Asn Gln
                260                 265                 270

Ser Gln Glu Thr Leu Gln Thr Val Thr Ile Tyr Ser Phe Pro Ala
                275                 280                 285

Pro Asn Val Ile Leu Thr Lys Pro Glu Val Ser Glu Gly Thr Glu
                290                 295                 300

Val Thr Val Lys Cys Glu Ala His Pro Arg Ala Lys Val Thr Leu
                305                 310                 315

Asn Gly Val Pro Ala Gln Pro Leu Gly Pro Arg Ala Gln Leu Leu
                320                 325                 330

Leu Lys Ala Thr Pro Glu Asp Asn Gly Arg Ser Phe Ser Cys Ser
                335                 340                 345

Ala Thr Leu Glu Val Ala Gly Gln Leu Ile His Lys Asn Gln Thr
                350                 355                 360

Arg Glu Leu Arg Val Leu Tyr Gly Pro Arg Leu Asp Glu Arg Asp
                365                 370                 375

Cys Pro Gly Asn Trp Thr Trp Pro Glu Asn Ser Gln Gln Thr Pro
                380                 385                 390

Met Cys Gln Ala Trp Gly Asn Pro Leu Pro Glu Leu Lys Cys Leu
                395                 400                 405

Lys Asp Gly Thr Phe Pro Leu Pro Ile Gly Glu Ser Val Thr Val
                410                 415                 420

Thr Arg Asp Leu Glu Gly Thr Tyr Leu Cys Arg Ala Arg Ser Thr
                425                 430                 435

Gln Gly Glu Val Thr Arg Lys Val Thr Val Asn Val Leu Ser Pro
                440                 445                 450

Arg Tyr Glu Asp Lys Thr His Thr Cys Pro Pro Cys Pro Ala Pro
                455                 460                 465

Glu Leu Leu Gly Gly Pro Ser Val Phe Leu Phe Pro Pro Lys Pro
                470                 475                 480

Lys Asp Thr Leu Met Ile Ser Arg Thr Pro Glu Val Thr Cys Val
                485                 490                 495

Val Val Asp Val Ser His Glu Asp Pro Glu Val Lys Phe Asn Trp
                500                 505                 510

Tyr Val Asp Gly Val Glu Val His Asn Ala Lys Thr Lys Pro Arg
                515                 520                 525

Glu Glu Gln Tyr Asn Ser Thr Tyr Arg Val Val Ser Val Leu Thr
                530                 535                 540

Val Leu His Gln Asp Trp Leu Asn Gly Lys Glu Tyr Lys Cys Lys
                545                 550                 555

Val Ser Asn Lys Ala Leu Pro Ala Pro Ile Glu Lys Thr Ile Ser
                560                 565                 570

Lys Ala Lys Gly Gln Pro Arg Glu Pro Gln Val Tyr Thr Leu Pro
                575                 580                 585

Pro Ser Arg Asp Glu Leu Thr Lys Asn Gln Val Ser Leu Thr Cys
                590                 595                 600
```

```
Leu Val Lys Gly Phe Tyr Pro Ser Asp Ile Ala Val Glu Trp Glu
                605                 610                 615

Ser Asn Gly Gln Pro Glu Asn Asn Tyr Lys Thr Thr Pro Pro Val
                620                 625                 630

Leu Asp Ser Asp Gly Ser Phe Phe Leu Tyr Ser Lys Leu Thr Val
                635                 640                 645

Asp Lys Ser Arg Trp Gln Gln Gly Asn Val Phe Ser Cys Ser Val
                650                 655                 660

Met His Glu Ala Leu His Asn His Tyr Thr Gln Lys Ser Leu Ser
                665                 670                 675

Leu Ser Pro Gly Lys
                680

(2) INFORMATION FOR SEQ ID NO:16:

(i) SEQUENCE CHARACTERISTICS:
        (A) LENGTH: 17 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: probe for HRV
        (D) OTHER INFORMATION: complementary to nucleotides
            455-471 of HRV-14 genome (xi) SEQUENCE DESCRIPTION: SEQ ID NO:16:

GCATTCAGGG GCCGGAG                                                      17

(2) INFORMATION FOR SEQ ID NO:17:

(i) SEQUENCE CHARACTERISTICS:
        (A) LENGTH: 1359 bp
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: tICAM(452) cys 307 mutant
        (D) OTHER INFORMATION: bp 1-1356 = sequence coding for
            amino acid residues 1-452 of human ICAM-1 with Cys
            substituted for Ala at position 307, and codons
            for Pro and Arg at positions 309 and 310
            respectively switched to equivalent redundant
            codons which provide a restriction site; bp 1357-
            1359 = stop codon (xi) SEQUENCE DESCRIPTION: SEQ ID NO:17:

CAG ACA TCT GTG TCC CCC TCA AAA GTC ATC CTG CCC CGG GGA GGC             45
Gln Thr Ser Val Ser Pro Ser Lys Val Ile Leu Pro Arg Gly Gly
                5                  10                  15

TCC GTG CTG GTG ACA TGC AGC ACC TCC TGT GAC CAG CCC AAG TTG             90
Ser Val Leu Val Thr Cys Ser Thr Ser Cys Asp Gln Pro Lys Leu
                20                 25                  30

TTG GGC ATA GAG ACC CCG TTG CCT AAA AAG GAG TTG CTC CTG CCT            135
```

```
Leu Gly Ile Glu Thr Pro Leu Pro Lys Lys Glu Leu Leu Pro
                35                  40                  45

GGG AAC AAC CGG AAG GTG TAT GAA CTG AGC AAT GTG CAA GAA GAT        180
Gly Asn Asn Arg Lys Val Tyr Glu Leu Ser Asn Val Gln Glu Asp
             50                  55                  60

AGC CAA CCA ATG TGC TAT TCA AAC TGC CCT GAT GGG CAG TCA ACA        225
Ser Gln Pro Met Cys Tyr Ser Asn Cys Pro Asp Gly Gln Ser Thr
             65                  70                  75

GCT AAA ACC TTC CTC ACC GTG TAC TGG ACT CCA GAA CGG GTG GAA        270
Ala Lys Thr Phe Leu Thr Val Tyr Trp Thr Pro Glu Arg Val Glu
             80                  85                  90

CTG GCA CCC CTC CCC TCT TGG CAG CCA GTG GGC AAG AAC CTT ACC        315
Leu Ala Pro Leu Pro Ser Trp Gln Pro Val Gly Lys Asn Leu Thr
             95                 100                 105

CTA CGC TGC CAG GTG GAG GGT GGG GCA CCC CGG GCC AAC CTC ACC        360
Leu Arg Cys Gln Val Glu Gly Gly Ala Pro Arg Ala Asn Leu Thr
            110                 115                 120

GTG GTG CTG CTC CGT GGG GAG AAG GAG CTG AAA CGG GAG CCA GCT        405
Val Val Leu Leu Arg Gly Glu Lys Glu Leu Lys Arg Glu Pro Ala
            125                 130                 135

GTG GGG GAG CCC GCT GAG GTC ACG ACC ACG GTG CTG GTG AGG AGA        450
Val Gly Glu Pro Ala Glu Val Thr Thr Thr Val Leu Val Arg Arg
            140                 145                 150

GAT CAC CAT GGA GCC AAT TTC TCG TGC CGC ACT GAA CTG GAC CTG        495
Asp His His Gly Ala Asn Phe Ser Cys Arg Thr Glu Leu Asp Leu
            155                 160                 165

CGG CCC CAA GGG CTG GAG CTG TTT GAG AAC ACC TCG GCC CCC TAC        540
Arg Pro Gln Gly Leu Glu Leu Phe Glu Asn Thr Ser Ala Pro Tyr
            170                 175                 180

CAG CTC CAG ACC TTT GTC CTG CCA GCG ACT CCC CCA CAA CTT GTC        585
Gln Leu Gln Thr Phe Val Leu Pro Ala Thr Pro Pro Gln Leu Val
            185                 190                 195

AGC CCC CGG GTC CTA GAG GTG GAC ACG CAG GGG ACC GTG GTC TGT        630
Ser Pro Arg Val Leu Glu Val Asp Thr Gln Gly Thr Val Val Cys
            200                 205                 210

TCC CTG GAC GGG CTG TTC CCA GTC TCG GAG GCC CAG GTC CAC CTG        675
Ser Leu Asp Gly Leu Phe Pro Val Ser Glu Ala Gln Val His Leu
            215                 220                 225

GCA CTG GGG GAC CAG AGG TTG AAC CCC ACA GTC ACC TAT GGC AAC        720
Ala Leu Gly Asp Gln Arg Leu Asn Pro Thr Val Thr Tyr Gly Asn
            230                 235                 240

GAC TCC TTC TCG GCC AAG GCC TCA GTC AGT GTG ACC GCA GAG GAC        765
Asp Ser Phe Ser Ala Lys Ala Ser Val Ser Val Thr Ala Glu Asp
            245                 250                 255

GAG GGC ACC CAG CGG CTG ACG TGT GCA GTA ATA CTG GGG AAC CAG        810
Glu Gly Thr Gln Arg Leu Thr Cys Ala Val Ile Leu Gly Asn Gln
            260                 265                 270

AGC CAG GAG ACA CTG CAG ACA GTG ACC ATC TAC AGC TTT CCG GCG        855
Ser Gln Glu Thr Leu Gln Thr Val Thr Ile Tyr Ser Phe Pro Ala
            275                 280                 285

CCC AAC GTG ATT CTG ACG AAG CCA GAG GTC TCA GAA GGG ACC GAG        900
Pro Asn Val Ile Leu Thr Lys Pro Glu Val Ser Glu Gly Thr Glu
            290                 295                 300

GTG ACA GTG AAG TGT GAG TGC CAC CCG CGG GCC AAG GTG ACG CTG        945
Val Thr Val Lys Cys Glu Cys His Pro Arg Ala Lys Val Thr Leu
            305                 310                 315

AAT GGG GTT CCA GCC CAG CCA CTG GGC CCG AGG GCC CAG CTC CTG        990
Asn Gly Val Pro Ala Gln Pro Leu Gly Pro Arg Ala Gln Leu Leu
            320                 325                 330
```

-continued

```
CTG AAG GCC ACC CCA GAG GAC AAC GGG CGC AGC TTC TCC TGC TCT            1035
Leu Lys Ala Thr Pro Glu Asp Asn Gly Arg Ser Phe Ser Cys Ser
            335                 340                 345

GCA ACC CTG GAG GTG GCC GGC CAG CTT ATA CAC AAG AAC CAG ACC            1080
Ala Thr Leu Glu Val Ala Gly Gln Leu Ile His Lys Asn Gln Thr
            350                 355                 360

CGG GAG CTT CGT GTC CTG TAT GGC CCC CGA CTG GAC GAG AGG GAT            1125
Arg Glu Leu Arg Val Leu Tyr Gly Pro Arg Leu Asp Glu Arg Asp
            365                 370                 375

TGT CCG GGA AAC TGG ACG TGG CCA GAA AAT TCC CAG CAG ACT CCA            1170
Cys Pro Gly Asn Trp Thr Trp Pro Glu Asn Ser Gln Gln Thr Pro
            380                 385                 390

ATG TGC CAG GCT TGG GGG AAC CCA TTG CCC GAG CTC AAG TGT CTA            1215
Met Cys Gln Ala Trp Gly Asn Pro Leu Pro Glu Leu Lys Cys Leu
            395                 400                 405

AAG GAT GGC ACT TTC CCA CTG CCC ATC GGG GAA TCA GTG ACT GTC            1260
Lys Asp Gly Thr Phe Pro Leu Pro Ile Gly Glu Ser Val Thr Val
            410                 415                 420

ACT CGA GAT CTT GAG GGC ACC TAC CTC TGT CGG GCC AGG AGC ACT            1305
Thr Arg Asp Leu Glu Gly Thr Tyr Leu Cys Arg Ala Arg Ser Thr
            425                 430                 435

CAA GGG GAG GTC ACC CGC AAG GTG ACC GTG AAT GTG CTC TCC CCC            1350
Gln Gly Glu Val Thr Arg Lys Val Thr Val Asn Val Leu Ser Pro
            440                 445                 450

CGG TAT TAG                                                            1359
Arg Tyr
```

(2) INFORMATION FOR SEQ ID NO:18:

(i) SEQUENCE CHARACTERISTICS:
        (A) LENGTH: 147 amino acid residues
        (B) TYPE: amino acid
        (C) TOPOLOGY: linear (ii) MOLECULE TYPE:
        (A) DESCRIPTION: peptide (iii) HYPOTHETICAL: no (v) FRAGMENT TYPE: N-terminal fragment (ix) FEATURE:
        (A) NAME/KEY: domains 4 and 5 of tmICAM-1
        (D) OTHER INFORMATION: amino acid sequence for domains
            4 and 5 of tmICAM-1

(xi) SEQUENCE DESCRIPTION: SEQ ID NO:18:

```
Pro Glu Val Ser Glu Gly Thr Glu Val Thr Val Lys Cys Glu Ala
              5                  10                  15

His Pro Arg Ala Lys Val Thr Leu Asn Gly Val Pro Ala Gln Pro
             20                  25                  30

Leu Gly Pro Arg Ala Gln Leu Leu Leu Lys Ala Thr Pro Glu Asp
             35                  40                  45

Asn Gly Arg Ser Phe Ser Cys Ser Ala Thr Leu Glu Val Ala Gly
             50                  55                  60

Gln Leu Ile His Lys Arg Val Leu Tyr Gly Pro Arg Leu Asp Glu
             65                  70                  75

Arg Asp Cys Pro Gly Asn Trp Thr Trp Pro Glu Asn Ser Gln Gln
             80                  85                  90

Thr Pro Met Cys Gln Ala Trp Gly Asn Pro Leu Pro Glu Leu Lys
             95                 100                 105

Cys Leu Lys Pro Gly Thr Phe Pro Leu Pro Ile Gly Glu Ser Val
```

```
                    110                 115                 120
Thr Val Thr Arg Asp Leu Glu Gly Thr Tyr Leu Cys Arg Ala Arg
                    125                 130                 135
Ser Thr Gln Gly Glu Val Thr Arg Glu Val Thr Val
                    140                 145
```

(2) INFORMATION FOR SEQ ID NO:19:

(i) SEQUENCE CHARACTERISTICS:
        (A) LENGTH: 505
        (B) TYPE: amino acids
        (D) TOPOLOGY: linear (ii) MOLECULE TYPE: protein (iii) HYPOTHETICAL: no (ix) FEATURE:
        (A) NAME/KEY: ICAM-1 protein (x) PUBLICATION INFORMATION:
        (A) AUTHORS: Staunton, D.E., Marlin, S.D., Stratowa, C., Dustin, M.L.,
        (B) TITLE: Primary Structure of ICAM-1 Demonstrates Interaction betwee
        (C) JOURNAL: Cell
        (D) VOLUME: 52
        (F) PAGES: 925-933
        (G) DATE: March 25, 1988

(xi) SEQUENCE DESCRIPTION: SEQ ID NO:19:

```
Gln Thr Ser Val Ser Pro Ser Lys Val Ile Leu Pro Arg Gly Gly
                    5                  10                  15
Ser Val Leu Val Thr Cys Ser Thr Ser Cys Asp Gln Pro Lys Leu
                    20                 25                  30
Leu Gly Ile Glu Thr Pro Leu Pro Lys Lys Glu Leu Leu Leu Pro
                    35                 40                  45
Gly Asn Asn Arg Lys Val Tyr Glu Leu Ser Asn Val Gln Glu Asp
                    50                 55                  60
Ser Gln Pro Met Cys Tyr Ser Asn Cys Pro Asp Gly Gln Ser Thr
                    65                 70                  75
Ala Lys Thr Phe Leu Thr Val Tyr Trp Thr Pro Glu Arg Val Glu
                    80                 85                  90
Leu Ala Pro Leu Pro Ser Trp Gln Pro Val Gly Lys Asn Leu Thr
                    95                 100                 105
Leu Arg Cys Gln Val Glu Gly Gly Ala Pro Arg Ala Asn Leu Thr
                    110                115                 120
Val Val Leu Leu Arg Gly Glu Lys Glu Leu Lys Arg Glu Pro Ala
                    125                130                 135
Val Gly Glu Pro Ala Glu Val Thr Thr Thr Val Leu Val Arg Arg
                    140                145                 150
Asp His His Gly Ala Asn Phe Ser Cys Arg Thr Glu Leu Asp Leu
                    155                160                 165
Arg Pro Gln Gly Leu Glu Leu Phe Glu Asn Thr Ser Ala Pro Tyr
                    170                175                 180
Gln Leu Gln Thr Phe Val Leu Pro Ala Thr Pro Pro Gln Leu Val
                    185                190                 195
Ser Pro Arg Val Leu Glu Val Asp Thr Gln Gly Thr Val Val Cys
                    200                205                 210
Ser Leu Asp Gly Leu Phe Pro Val Ser Glu Ala Gln Val His Leu
                    215                220                 225
Ala Leu Gly Asp Gln Arg Leu Asn Pro Thr Val Thr Tyr Gly Asn
```

```
                      230                 235                 240
Asp Ser Phe Ser Ala Lys Ala Ser Val Ser Val Thr Ala Glu Asp
                  245                 250                 255
Glu Gly Thr Gln Arg Leu Thr Cys Ala Val Ile Leu Gly Asn Gln
                  260                 265                 270
Ser Gln Glu Thr Leu Gln Thr Val Thr Ile Tyr Ser Phe Pro Ala
                  275                 280                 285
Pro Asn Val Ile Leu Thr Lys Pro Glu Val Ser Glu Gly Thr Glu
                  290                 295                 300
Val Thr Val Lys Cys Glu Ala His Pro Arg Ala Lys Val Thr Leu
                  305                 310                 315
Asn Gly Val Pro Ala Gln Pro Leu Gly Pro Arg Ala Gln Leu Leu
                  320                 325                 330
Leu Lys Ala Thr Pro Glu Asp Asn Gly Arg Ser Phe Ser Cys Ser
                  335                 340                 345
Ala Thr Leu Glu Val Ala Gly Gln Leu Ile His Lys Asn Gln Thr
                  350                 355                 360
Arg Glu Leu Arg Val Leu Tyr Gly Pro Arg Leu Asp Glu Arg Asp
                  365                 370                 375
Cys Pro Gly Asn Trp Thr Trp Pro Glu Asn Ser Gln Gln Thr Pro
                  380                 385                 390
Met Cys Gln Ala Trp Gly Asn Pro Leu Pro Glu Leu Lys Cys Leu
                  395                 400                 405
Lys Asp Gly Thr Phe Pro Leu Pro Ile Gly Glu Ser Val Thr Val
                  410                 415                 420
Thr Arg Asp Leu Glu Gly Thr Tyr Leu Cys Arg Ala Arg Ser Thr
                  425                 430                 435
Gln Gly Glu Val Thr Arg Glu Val Thr Val Asn Val Leu Ser Pro
                  440                 445                 450
Arg Tyr Glu Ile Val Ile Ile Thr Val Val Ala Ala Ala Val Ile
                  455                 460                 465
Met Gly Thr Ala Gly Leu Ser Thr Tyr Leu Tyr Asn Arg Gln Arg
                  470                 475                 480
Lys Ile Lys Lys Tyr Arg Leu Gln Gln Ala Gln Lys Gly Thr Pro
                  485                 490                 495
Met Lys Pro Asn Thr Gln Ala Thr Pro Pro
                  500                 505

(2) INFORMATION FOR SEQ ID NO:20:

(i) SEQUENCE CHARACTERISTICS:
        (A) LENGTH: 1656
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: ICAM-1 coding sequence (x) PUBLICATION INFORMATION:
        (A) AUTHORS: Staunton, D.E., Marlin, S.D., Stratowa, C., Dustin, M.L.,
        (B) TITLE: Primary Structure of ICAM-1 Demonstrates Interaction betwee
        (C) JOURNAL: Cell
        (D) VOLUME: 52
```

-continued

```
        (F) PAGES: 925-933
        (G) DATE: March 25, 1988
        (K) RELEVANT RESIDUES IN SEQ ID NO:2: From 58 to
            1653

(xi) SEQUENCE DESCRIPTION: SEQ ID NO:20:

GCGCCCCAGT CGACGCTGAG CTCCTCTGCT ACTCAGAGTT GCAACCTCAG CCTCGCTATG      60

GCTCCCAGCA GCCCCCGGCC CGCGCTGCCC GCACTCCTGG TCCTGCTGGG GGCTCTGTTA     120

CCAGGACCTG GCAATGCCCA GACATCTGTG TCCCCCTCAA AAGTCATCCT GCCCCGGGGA     180

GGCTCCGTGC TGGTGACATG CAGCACCTCC TGTGACCAGC CCAAGTTGTT GGGCATAGAG     240

ACCCCGTTGC CTAAAAAGGA GTTGCTCCTG CCTGGGAACA ACCGGAAGGT GTATGAACTG     300

AGCAATGTGC AAGAAGATAG CCAACCAATG TGCTATTCAA ACTGCCCTGA TGGGCAGTCA     360

ACAGCTAAAA CCTTCCTCAC CGTGTACTGG ACTCCAGAAC GGGTGGAACT GGCACCCCTC     420

CCCTCTTGGC AGCCAGTGGG CAAGAACCTT ACCCTACGCT GCCAGGTGGA GGGTGGGGCA     480

CCCCGGGCCA ACCTCACCGT GGTGCTGCTC CGTGGGGAGA AGGAGCTGAA ACGGGAGCCA     540

GCTGTGGGGG AGCCCGCTGA GGTCACGACC ACGGTGCTGG TGAGGAGAGA TCACCATGGA     600

GCCAATTTCT CGTGCCGCAC TGAACTGGAC CTGCGGCCCC AAGGGCTGGA GCTGTTTGAG     660

AACACCTCGG CGCCCTACCA GCTCCAGACC TTTGTCCTGC CAGCGACTCC CCCACAACTT     720

GTCAGCCCCC GGGTCCTAGA GGTGGACACG CAGGGGACCG TGGTCTGTTC CCTGGACGGG     780

CTGTTCCCAG TCTCGGAGGC CCAGGTCCAC CTGGCACTGG GGGACCAGAG GTTGAACCCC     840

ACAGTCACCT ATGGCAACGA CTCCTTCTCG GCCAAGGCCT CAGTCAGTGT GACCGCAGAG     900

GACGAGGGCA CCCAGCGGCT GACGTGTGCA GTAATACTGG GAACCAGAG CCAGGAGACA      960

CTGCAGACAG TGACCATCTA CAGCTTTCCG GCGCCCAACG TGATTCTGAC GAAGCCAGAG    1020

GTCTCAGAAG GGACCGAGGT GACAGTGAAG TGTGAGGCCC ACCCTAGAGC CAAGGTGACG    1080

CTGAATGGGG TTCCAGCCCA GCCACTGGGC CCGAGGGCCC AGCTCCTGCT GAAGGCCACC    1140

CCAGAGGACA ACGGGCGCAG CTTCTCCTGC TCTGCAACCC TGGAGGTGGC CGGCCAGCTT    1200

ATACACAAGA ACCAGACCCG GGAGCTTCGT GTCCTGTATG GCCCCCGACT GGACGAGAGG    1260

GATTGTCCGG GAAACTGGAC GTGGCCAGAA AATTCCCAGC AGACTCCAAT GTGCCAGGCT    1320

TGGGGGAACC CATTGCCCGA GCTCAAGTGT CTAAAGGATG GCACTTTCCC ACTGCCCATC    1380

GGGGAATCAG TGACTGTCAC TCGAGATCTT GAGGGCACCT ACCTCTGTCG GGCCAGGAGC    1440

ACTCAAGGGG AGGTCACCCG CGAGGTGACC GTGAATGTGC TCTCCCCCCG GTATGAGATT    1500

GTCATCATCA CTGTGGTAGC AGCCGCAGTC ATAATGGGCA CTGCAGGCCT CAGCACGTAC    1560

CTCTATAACC GCCAGCGGAA GATCAAGAAA TACAGACTAC AACAGGCCCA AAAAGGGACC    1620

CCCATGAAAC CGAACACACA AGCCACGCCT CCCTGA                              1656
```

ANTIVIRAL METHODS

This application is a continuation of copending application U.S. Ser. No. 07/903,069, filed Jun. 22, 1992 now abandoned, which is a continuation-in-part of U.S. Ser. No. 07/704,984, filed May 24, 1991 abandoned, which is a continuation-in-part of U.S. Ser. No. 07/556,238, filed Jul. 20, 1990 abandoned.

BACKGROUND OF THE INVENTION

The present invention relates to novel forms and multimeric configurations of intercellular adhesion molecule (ICAM), including both full-length and truncated forms of these proteins, that effectively bind to human rhinovirus and can effectively reduce HRV infectivity, and to methods of making and using same.

Full-length ICAM, also known as human rhinovirus receptor (HRR), is termed transmembrane ICAM (tmICAM-1); non-transmembrane ICAM forms, also known as truncated ICAM (tICAM), are less than full length. When in a multimeric configuration, preferably as dimers, these proteins display enhanced binding of human rhinovirus (HRV) and are able to reduce HRV infectivity. In addition, these multimerized proteins may also be used to reduce infectivity of other viruses that are known to bind to the 'major' group human rhinovirus receptor (HRR), such as Coxsackie A virus, and may also be used to block transmembrane intercellular adhesion molecule (tmICAM) interaction with lymphocyte function-associated antigen-1 (LFA-1), which is critical to many cell adhesion processes involved in the immunological response. Lastly, these multimerized proteins may be used to study the ICAM-1/HRV interaction especially with respect to designing other drugs directed at affecting this interaction.

Human rhinoviruses are the major causative agent of the common cold. They belong to the picornavirus family and can be classified based on the host cell receptor to which they bind. Tomassini, et al., J. Virol., 58: 290 (1986) reported the isolation of a receptor protein involved in the cell attachment of human rhinovirus. Approximately 90% of the more than 115 serotypes of rhinoviruses, as well as several types of Coxsackie A virus, bind to a single common receptor termed the "major" human rhinovirus receptor (HRR); the remaining 10% bind to one or more other cell receptors.

Recently, Greve, J. et al., Cell, 56:839 (1989), co-authored by the co-inventors herein, identified the major HRR as a glycoprotein with an apparent molecular mass of 95,000 daltons and having an amino acid sequence essentially identical to that deduced from the nucleotide sequence of a previously described cell surface protein named intercellular adhesion molecule (ICAM-1) [Simmons, D. et al., Nature, 331:624 (1988); Staunton, et al., Cell, 52:925–933 (1988)]. Subsequently, Staunton, D. E., et al., Cell, 56:849 (1989), confirmed that ICAM-1 is the major surface receptor for HRV. See also, Staunton, et al., Cell, 61:243–254 (1990).

ICAM-1 is an integral membrane (numbered acording to Staunton et al., 1988) protein 505 amino acids long [SEQ ID NO:19] and has: i) five immunoglobulin-like extracellular domains at the amino-terminal end (amino acid residues 1–453), ii) a hydrophobic transmembrane domain (454–477), and iii) a short cytoplasmic domain at the carboxy-terminal end (478–505). See FIG. 1. ICAM-1 is a member of the immunoglobulin supergene family and functions as a ligand for the leukocyte molecule, lymphocyte function associated molecule-1 (LFA-1), a member of the integrin family. Heterotypic binding of LFA-1 to ICAM-1 mediates cellular adhesion of diverse cell types and is important in a broad range of immune interactions; induction of ICAM-1 expression by cytokines during the inflammatory response may regulate leukocyte localization to inflammatory sites. The primary structure of ICAM-1 has been found to be homologous to two cellular adhesion molecules, i.e., neural cell adhesion molecule (NCAM) and myelin-associated glycoprotein (MAG).

Several approaches to decreasing infectivity of viruses in general, and of rhinovirus in particular, have been pursued including: i) developing antibody to the cell surface receptor for use in blocking viral binding to the cell, ii) using interferon to promote an anti-viral state in host cells; iii) developing various agents to inhibit viral replication; iv) developing antibodies to viral capsid proteins/peptides; and v) blocking viral infection with isolated cell surface receptor protein that specifically blocks the viral binding domain of the cell surface receptor.

Using this last approach, Greve, et al., Cell, 56:879 (1989), supra, reported that purified tmICAM-1 could bind to rhinovirus HRV3 in vitro. Unpublished results with HRV2, HRV3, and HRV14 demonstrate a positive correlation between the ability to bind to rhinovirus and the ability to neutralize rhinovirus particularly if the binding studies are carried out under conditions where ICAM-1 is presented in a particular form and configuration as discussed further, infra. Results (unpublished) using HRV14 and HRV2 demonstrate a positive correlation between the receptor class of the virus and the ability to bind to tmICAM-1 in vitro. That is, ICAM-1, being the major receptor, can bind to HRV3, HRV14, and other "major" receptor serotypes and neutralize them, while it does not bind or neutralize HRV2, a "minor" receptor serotype. Further studies (unpublished), using purified tmICAM-1, demonstrate that it effectively inhibits rhinovirus infectivity in a plaque-reduction assay when the rhinovirus is pretreated with tmICAM-1 (50% reduction of titer at 10 nM receptor and one log reduction of titer at 100 nM receptor protein). These data were consistent with the affinity of rhinovirus for ICAM-1 of Hela cells, which had an apparent dissociation constant of 10 nM, and indicated a direct relationship between the ability of the receptor to bind to the virus and to neutralize the virus.

Because large-scale production of tmICAM-1 is not presently economically feasible, and because maintenance of tmICAM-1 in an active form requires the use of detergents, alternate means of producing a receptor protein for use as a rhinovirus inhibitor are desirable. Forms of the tmICAM-1 cDNA gene have been developed (as well as cell lines that produce the expression products; U.S. Ser. No. 07/390,662, now abandoned) that have been genetically altered to produce truncated ICAM-1 molecules. See FIG. 1. These truncated forms of ICAM-1 (tICAM(453) and tICAM(185)) lack the transmembrane region and are secreted into the cell culture medium. They bind to rhinovirus in the assay described in Greve, et al., Cell, 56:879 (1989), supra, although at substantially reduced levels relative to tmICAM-1. Thus, their effectiveness as inhibitors of rhinoviral infectivity appeared to be less than that of tmICAM-1. See generally co-pending applications U.S. Ser. No. 07/239,571, now abandoned; U.S. Ser. No. 07/262,428, now abandoned; U.S. Ser. No. 07/678,909, now abandoned; U.S. Ser. No. 07/631,313, now abandoned; U.S. Ser. No. 07/301,192, now U.S. Pat. No. 5,235,049; U.S. Ser. No. 07/449,356, now abandoned; U.S. Ser. No. 07/798,267, now abandoned; U.S. Ser. No. 07/556,238, now abandoned; U.S. Ser. No. 07/704,996, now abandoned; and U.S. Ser. No. 07/704,984, now abandoned.

U.S. Ser. No. 07/239,571, now abandoned, filed Sep. 1, 1988, and its CIP applications U.S. Ser. No. 07/262,428, now abandoned, U.S. Ser. No. 07/390,662 (abandoned in favor of continuation U.S. Ser. No. 07/678,909), U.S. Ser. No. 07/631,313, now abandoned, and U.S. Ser. No. 07/704, 996, now abandoned, are directed to the use of transmembrane rhinovirus receptor as an inhibitor of rhinovirus infectivity using non-ionic detergent to maintain the transmembrane protein in solution, and directed to truncated intercellular adhesion molecules (tICAM) comprising one or more of the extracellular domains I, II, III, IV, and V of tmICAM, which truncated forms do not require the presence of non-ionic detergent for solubilization (see FIG. 1).

U.S. Ser. No. 07/130,378 filed Dec. 8, 1987 (abandoned in favor of continuation application U.S. Ser. No. 07/798, 267), and CIP application U.S. Ser. No. 07/262,570 (now abandoned) are directed to transfected non-human mammalian cell lines which express the major rhinovirus receptor (HRR) and to the identification of HRR as intercellular adhesion molecule.

U.S. Ser. No. 07/301,192, now U.S. Pat. No. 5,235,049, filed Jan. 24, 1989, and its CIP application U.S. Ser. No. 07/449,356, now abandoned, are directed to a naturally-occurring soluble ICAM (sICAM) related to but distinct from tmICAM in that this sICAM lacks the amino acids spanning the transmembrane region and the cytoplasmic region; in addition this sICAM has a novel sequence of 11 amino acids at the C-terminus.

Subsequently, Marlin, S. D., et al., Nature, 344:70 (1990), reported the construction and purification of a truncated soluble form of the normally membrane-bound ICAM-1 molecule which they termed sICAM-1. It has both the transmembrane domain and the cytoplasmic domain of the protein deleted and differs from the wild-type amino acid sequence by a single conservative substitution at its carboxyl end. It is composed of residues 1–452 of ICAM-1 plus a novel phenylalanine residue at the C-terminus. These workers demonstrated that sICAM-1 was required at levels >50 $\mu$g/ml to prevent the binding of HRV14 virus to cells. However, they also found that sICAM-1 at 1 $\mu$g/ml (18 nM), when continually present in the culture medium, was able to inhibit by 50% the progression of an infection by HRV54. The inhibitory activity was correlated with the receptor class of the virus, in that Coxsackie A13 but not poliovirus or HRV2 was inhibited; infectivity data for HRV14 was not reported, however. Thus, they did not demonstrate a direct correlation between binding and inhibition of infectivity. Further, as discussed in greater detail, infra, attempts to reproduce the results obtained by Marlin, et al. have not been successful.

To date, no one has been able to demonstrate an agent that binds to and effectively reduces infectivity of human rhinovirus (by blocking viral infection with isolated cell surface receptor protein) as effectively as tmICAM-1; accordingly there continues to exist a need in the art for a form of ICAM-1 that can effectively bind to human rhinovirus and can effectively reduce HRV infectivity.

BRIEF SUMMARY OF THE INVENTION

Provided by the invention are multimeric configurations of transmembrane ICAM (tmICAM-1) and multimeric configurations of non-transmembrane ICAMs (tICAMs), having improved rhinovirus binding and inhibition activity.

As noted, supra, tmICAM-1 isolated from mammalian cells has the capacity to neutralize human rhinoviruses belonging to the major receptor group, but only if maintained in solution with detergent. Certain soluble fragments of ICAM-1 have been found to have a reduced capacity for binding virus and do not reduce infectivity as effectively as tmICAM-1. To date, no one has been able to ascertain the reason for this reduced capacity.

It has been proposed by others that the rhinovirus receptor exists on cells in a pentameric form [Tomassini, J., and Colonno, R., J. Virol., 58:290–295 (1986)]. However, quantitation (unpublished results of the co-inventors herein) of the rhinovirus and anti-ICAM-1 monoclonal antibody (Mab) binding to HeLa cells has revealed a maximum of 30,000 virions bound per cell (determined by the binding of [$^{35}$S] methionine-labeled HRV) and 50,000–60,000 ICAM-1 molecules per cell (determined by the binding of radio-labeled Mab to ICAM-1). These results prompted further studies to examine the possibility that rather than five, only between one and two ICAM-1 molecules on the surface of cells are bound per HRV particle bound to the cell.

Genetically engineered forms of truncated ICAM-1 that lack the C-terminal transmembrane domain are secreted into the culture medium of mammalian cells transfected with the recombinant gene. The purification of such secreted ICAM molecules from spent culture medium of cells stably transfected with the genes therefor is described herein. In a solution-HRV binding assay and in an HRV neutralization assay, it was found that the monomeric forms tend to have substantially reduced avidity for HRV relative to tmICAM-1. However, it has now been discovered that when such tICAMs are presented in multimeric form and then incubated with HRV, the virus-binding activity of the multimeric tICAMs becomes comparable to that of tmICAM-1. This binding of multimeric tICAMs to HRV has the same properties as the binding of HRV to ICAM-1 on HeLa cells: it is inhibited by anti-ICAM-1 Mabs, it is specific for rhinoviruses of the major receptor group, and has the same temperature dependence as the binding of rhinovirus to cells (i.e., binds well at 37° C. and undetectably at 4° C.). It is postulated that tmICAM exists in nature in a multimeric, possibly dimeric form, and that such constructs more closely resemble the native configuration, with its attendant high avidity for the human rhinovirus. Such dimerization may conveniently be achieved in vitro by, e.g., crosslinking two ICAM monomers by chemical means or by crosslinking with appropriate antibodies, or by binding monomers to appropriate inert substrates. Multimerization can also be achieved in vivo by modification of the gene sequence coding for the select ICAM to provide appropriate binding sites in the corresponding peptide sequence. For example, muteins can be engineered which contain appropriate cysteine residues to allow in vivo multimerization via interchain disulfide bonding. Alternatively, a DNA sequence coding for an ICAM may be fused with a DNA sequence coding for an appropriate immunoglobulin or fragment thereof, such that the fusion gene product possesses at least one site suitable for interchain bonding. The resulting fusion peptide monomer can then be expressed by the cell in multimeric form. Under certain circumstances, the benefits of multimerization may also be achieved by construction of ICAM muteins containing multiple rhinovirus binding sites.

Also provided by the invention are methods for enhancing binding of ICAM and functional derivatives thereof to a ligand, i.e., human rhinovirus, and "major" group receptor viruses, lymphocyte function-associated antigen-1 (LFA-1), *Plasmodium falciparum* (malaria) and the like, wherein the ICAM is presented in a multimeric configuration to the ligand to facilitate binding of the ICAM to the ligand.

The invention further comprises a method for inducing irreversible uncoating of human rhinovirus, said method comprising contacting said human rhinovirus with ICAM-1 or a fragment thereof.

This invention also provides a novel method of irreversibly inhibiting infectivity of a mammalian cell by a human rhinovirus, said method comprising contacting said human rhinovirus with ICAM-1 or a fragment thereof under conditions which allow the ICAM-1 or fragment thereof to bind to said rhinovirus; thereby stimulating irreversible uncoating of said rhinovirus.

Also provided by the invention are novel pharmaceutical compositions comprising a pharmaceutically acceptable solvent, diluent, adjuvant or carrier, and as the active ingredient, an effective amount of a polypeptide characterized by having human rhinovirus binding activity and reduction of virus infectivity. Dimeric configurations of ICAM and fragments thereof are presently preferred.

Other aspects and advantages of the present invention will be apparent upon consideration of the following detailed description thereof which includes numerous illustrative examples of the practice of the invention.

DESCRIPTION OF THE FIGURES

FIG. 1 is a schematic rendition of a) tmICAM-1, b) tICAM(453), c) tICAM(283), d) tICAM(185), and e) tICAM(88).

FIG. 2 is a schematic diagram of the constructs of Example 12: a) the heavy chain of human IgG; b) the fragment of the heavy chain used in making the immunoadhesin; c) the fragment of ICAM; d) the completed IgG/ICAM immunoadhesin.

FIG. 3 shows crosslinking of tICAM(453) into dimers by water-soluble carbodiimide/N-hydroxysuccinimide. tICAM (453) at the indicated concentrations was crosslinked with 100 mM EDC/5 mM NHS at pH 7.5 for 18 hr at 20 C. The samples were analyzed by SDS-PAGE followed by western blotting with anti-ICAM-1 antisera. a) Western blot of crosslinked ICAM(453) showing monomer and dimer species; b) dependence of crosslinking upon tICAM(453) concentration; c) the crosslinking of tICAM(453) is not inhibited by an excess of third-party proteins.

FIG. 4 is a schematic showing construction of tICAM (1–451)/LFA-3(210–237) chimera: a) tmICAM-1; b) tICAM(1–451); c) LFA-3; d) LFA-3(210–237); e) tICAM (1–451)/LFA-3(210–237) chimera; structure of tmICAM-1 shown for comparison.

FIG. 5 shows uncoating of HRV by tICAM(453) over 24 hours. a) shift from native 148S form to uncoated 42S form by tICAM(453); b) shift from native 148S to uncoated 42S form by tICAM(185); c)SDS-PAGE of [$^{35}$S]-methionine-labelled HRV-3 showing loss of VP4; d) dot-blot hybridization of RNA recovered from HRV3 species with an oligonucleotide probe for HRV. 50 ng of purified HRV3 RNA and RNA extracted from 8 ng of HRV3 species were applied to the blot.

FIG. 6 (SEQ ID NO:19) shows the predicted alignment of ICAM-1 amino acid sequence in domains IV and V onto the [SEQ ID NO:18] immunoglobulin fold motif. Arrows indicate beta strands, pointing from the N- to the C-terminus; italicized letters in bold indicate the beta strands, and numbered residues indicate cysteine residues with disulfide bonds indicated by lines. The dotted line divides the "B" and "F" faces of the domains. Residues indicated with an * are among those replaced with cysteine residues.

DETAILED DESCRIPTION OF THE INVENTION

As used herein, the following abbreviations and terms include, but are not necessarily limited to, the following definitions.

| Abbreviation | Definition |
|---|---|
| ICAM | Intercellular adhesion molecule may be used to denote both full length (trans-membrane) and truncated (non-trans-membrane) forms of the protein. |
| ICAM-1 | Intercellular adhesion molecule-1, also known as tmICAM-1 and HRR; denoting the full-length transmembrane protein |
| tmICAM-1 | Transmembrane intercellular adhesion molecule-1, also known as ICAM-1 and HRR; requires, e.g., detergent conditions to be solubilized |
| HRR | Human rhinovirus receptor, also known as ICAM-1 and tmICAM-1 |
| sICAM-1 | A naturally-occurring soluble truncated form of ICAM-1 having both the hydrophobic transmembrane domain and the carboxy-terminal cytoplasmic domain of ICAM-1 deleted; consists of amino acids 1-442 of ICAM-1 plus 11 novel amino acids; distinguishable from Staunton, et al. tICAM453 which consists of amino acids 1-453 with the terminal tyrosine replaced with phenylalanine. |
| tICAMs | Truncated intercellular adhesion molecules; soluble non-transmembrane ICAMs lacking the hydrophobic trans-membrane domain and the carboxyl-terminal cytoplasmic domain of ICAM-1. |
| tICAM(1–453)<br>tICAM-453<br>tICAM(453) | Truncated form of ICAM comprising the entire extracellular amino-terminal domain of tmICAM (domains I–V, amino acid residues 1–453) |
| tICAM(1–283)<br>tICAM-283<br>tICAM(283) | Truncated form of ICAM comprising domains I, II, and III (amino acid residues 1–283 |
| tICAM(1–185)<br>tICAM-185<br>tICAM(185) | Truncated form of ICAM comprising domains I and II (amino acid residues 1–185) |
| tICAM(1–88)<br>tICAM-88<br>tICAM(88) | Truncated form of ICAM comprising domain I (amino acid residues 1–88) |
| tICAM(89–185) | Truncated form of ICAM comprising domain II (amino acid residues 89–185) |
| tICAM(186–283) | Truncated form of ICAM comprising domain III (amino acid residues 186–283) |
| tICAM(284–385) | Truncated form of ICAM comprising domain IV (amino acid residues 284–385) |
| tICAM(386–453) | Truncated form of ICAM comprising domain V (amino acid residues 386–453) |
| tICAM(75–77) | Truncated form of ICAM comprising amino acid residues 75–77) |
| tICAM(70–72) | Truncated form of ICAM comprising amino acid residues 70–72 |
| tICAM(64–66) | Truncated form of ICAM comprising amino acid residues 64–66 |
| tICAM(40–43) | Truncated form of ICAM comprising amino acid residues 40–43 |
| tICAM(36–38) | Truncated form of ICAM comprising amino acid residues 36–38) |
| tICAM(30–33) | Truncated form of ICAM comprising amino acid residues 30–33) |
| tICAM(26–29) | Truncated form of ICAM comprising amino acid residues 26–29 |

The foregoing terms defining specific fragments are intended to include functional derivatives and analogs thereof. Persons skilled in the art will understand that the given boundaries may vary by a few amino acid residues without affecting the function of the given fragment.

"Multimerization" and "multimeric" include, but are not limited to dimerization and dimeric, and include any multimeric configuration of the ICAM-1 molecule, or fragment thereof, that is effective in reducing viral binding and infectivity.

"Transmembrane" generally means forms of the ICAM-1 protein molecule which possess a hydrophobic membrane-spanning sequence and which are membrane-bound.

"Non-transmembrane" generally means soluble forms of the ICAM-1 protein including truncated forms of the protein that, rather than being membrane-bound, are secreted into the cell culture medium as soluble proteins, as well as transmembrane forms that have been solubilized from cell membranes by lysing cells in non-ionic detergent.

"Truncated" generally includes any protein form that is less than the full length transmembrane form of ICAM.

"Immunoadhesin" means a construct comprising all or a part of a protein or peptide fused to an immunoglobulin fragment, preferably a fragment comprising at least one constant region of an immunoglobulin heavy chain.

"Form" is generally used herein to distinguish among full length and partial length ICAM forms; whereas "configuration" is generally used to distinguish among monomeric, dimeric, and multimeric configurations of possible ICAM forms.

All forms and configurations of the ICAM-1 molecule, whether full length or a fragment thereof, including muteins and immunoadhesins, whether monomeric or multimeric, may be fully or partially glycosylated, or completely unglycosylated, as long as the molecule remains effective in reducing viral binding and infectivity.

"Ligand" is generally used herein to include anything capable of binding to at least one of any of the forms and configurations of ICAM and includes, but is not limited to, human rhinovirus, other viruses that bind to the "major" group human rhinovirus receptor, lymphocyte function-associated antigen-1, and *Plasmodium falciparum* (malaria).

"Human rhinovirus" generally includes all human serotypes of human rhinovirus as catalogued in Hamparian, V., et al., Virol., 159:191–192 (1987).

The sequence of amino acid residues in a peptide is designated in accordance with standard nomenclature such as that given in Lehninger's *Biochemistry* (Worth Publishers, New York, 1970).

Full-length ICAM-1, also known as human rhinovirus receptor (HRR), is termed transmembrane ICAM(tmICAM-1). Non-transmembrane ICAMs are also known as truncated ICAMS, i.e, ICAMs substantially without the carboxyl intracellular domain and without the hydrophobic membrane domain of tmICAM, which are soluble without the addition of detergent. tICAMs may conveniently comprise one or more domains selected substantially from domains I, II, III, IV, and V of the extracellular region of tmICAM. tICAMs may also comprise functional analogs of tmICAM or fragments thereof, and may also comprise one or more fragments of tmICAM spliced together, with or without intervening non-tmICAM linking sequences, and not necessarily in the same order found in native tmICAM. Presently preferred tICAMs include but are not limited to forms tICAM(453), tICAM(185), tICAM(88), tICAM(283), and tICAMs comprising one or more sequences selected from tICAM(89–185), tICAM(186–283), tICAM(284–385), tICAM(386–453), tICAM(75–77), tICAM(70–72), tICAM (64–66), tICAM(40–43), tICAM(36–38), tICAM(30–33), and tICAM(26–29). See U.S. Ser. No. 07/631,313, U.S. Ser. No. 07/678,909, and U.S. Ser. No. 07/704,996. Non-transmembrane forms of ICAM can include functional derivatives of ICAM, mutein forms of tICAM to facilitate coupling, and tICAM immunoadhesins. When the tICAMs are in a multimeric configuration, preferably as dimers, they display enhanced binding of human rhinovirus and are able to reduce viral infectivity.

Multimerization can be achieved by crosslinking a first ICAM to a second ICAM, using suitable crosslinking agents, e.g. heterobifunctional and homobifunctional crosslinking reagents such as bifunctional N-hydroxysuccinimide esters, imidoesters, or bis-maleimidohexanes.

The different forms of ICAM, transmembrane and non-transmembrane, can be multimerized by adsorption to a support. This support can be made of materials such as nitrocellulose, PVDF, DEAE, lipid polymers, as well as amino dextran, or a variety of inert polymers that can adsorb or can be coupled to ICAM, either with or without a spacer or linker.

Multimeric ICAM can also be multimerized by coupling the ICAM to a member, e.g., an antibody that does not interfere with HRV binding, or fragments thereof; or to a protein carrier. An example of an antibody includes anti-ICAM antibody CL 203 or a fragment thereof; suitable protein carriers include albumin and proteoglycans.

To facilitate coupling, the ICAM can be modified with at least one reactive amino acid residue such as lysine, cysteine, or other amino acid residue(s) to provide a site(s) to facilitate coupling. These types of modified ICAM are referred to as muteins. The nucleotide sequence for the ICAM of the method can be contained in a vector, such as a plasmid, and the vector can be introduced into a host cell, for example eukaryotic or prokaryotic cells. The preferred eukaryotic cell is a mammalian cell, e.g. Chinese hamster ovary cells or HEK293S cells; the preferred prokaryotic cell is *E. coli*. In addition, the ICAM can be modified at either terminus to comprise a lipid capable of promoting formation of oligomer micelles. The ICAM comprising the multimeric ICAM can be either fully glycosylated, partially glycosylated, or non- glycosylated.

A preferred manner of making multimeric forms of ICAM-1 is by engineering of cysteine residues into the tICAM sequence (tICAM(453) is particularly preferred) in a position at or close to the natural site of self-association on ICAM-1 monomers. Muteins with cysteine residues placed at appropriate positions form covalent bonds (disulfide bonds) that stabilize an interaction which is noncovalent in vivo. Such muteins are assembled intracellularly and are expressed as a disulfide-linked dimer; alternatively, monomeric muteins may be crosslinked in vitro by incubation at high protein concentration in mildly reducing conditions to encourage disulfide exchange, or by crosslinking with bifunctional chemical crosslinking reagents which react with free sulfhydryl groups. Another advantage of such proteins is that any novel amino acids engineered into ICAM-1 are hidden on the dimer interface and would be less likely to be immunogenic.

In another preferred embodiment, ICAM can also be multimerized by fusion with fragments of immunoglobulins to form ICAM immunoadhesins. For example, an ICAM or fragment thereof can be fused with a heavy or light chain immunoglobulin or fragment thereof, in particular with the constant region of the heavy chain of IgG, IgA, or IgM. Preferably, the constant region contains the hinge region and one or more of CH2 and CH3, but does not contain CH1. The variable region (Fab) of the immunoglobulin is thus replaced by the ICAM or fragment thereof. Such constructs are conveniently produced by construction and expression of a suitable fusion gene in a suitable expression system [see, e.g., Bebbington, C. R. and C. C. G. Hentschel, "The use of vectors based on gene amplification for the expression of cloned genes in mammalian cells," in *DNA Cloning. Vol. III*, D. Glover, ed.(1987)] and are secreted in a dimerized configuration.

Also provided by the invention are methods for enhancing binding of ICAM and functional derivatives thereof to a ligand, i.e., human rhinovirus, and "major" group receptor viruses, lymphocyte function-associated antigen-1 (LFA-1), *Plasmodium falciparum* (malaria) and the like, wherein the ICAM is presented in a multimeric configuration to the ligand to facilitate binding of the ICAM to the ligand.

The invention further comprises a method for inducing irreversible uncoating of human rhinovirus, said method comprising contacting said human rhinovirus with ICAM-1 or a fragment thereof, e.g. a tICAM as defined above.

This invention also provides a novel method of irreversibly inhibiting infectivity of a mammalian cell by a human rhinovirus, said method comprising contacting said human rhinovirus with ICAM-1 or a fragment thereof under conditions which allow the ICAM-1 or fragment thereof (e.g. a tICAM as defined above) to bind to said rhinovirus; thereby stimulating irreversible uncoating of said rhinovirus.

Also provided by the invention are novel pharmaceutical compositions comprising a pharmaceutically acceptable solvent, diluent, adjuvant or carrier, and as the active ingredient, an effective amount of a polypeptide characterized by having human rhinovirus binding activity and reduction of virus infectivity. Dimeric configurations of ICAM and fragments thereof are presently preferred.

The following examples illustrate practice of the invention.

Example 1 relates to growth, purification and assay of rhinoviruses;

Example 2 relates to production and isolation of monoclonal antibodies to ICAM-1;

Example 3 relates to construction of non-transmembrane truncated forms of ICAM cDNA from full length ICAM-1 cDNA;

Example 4 relates to transfection of mammalian-cells and expression of non-transmembrane truncated forms of ICAM cDNA;

Example 5 relates to isolation and purification of non-transmembrane truncated forms of ICAM-1;

Example 6 relates to radioactive labeling of tmICAM-1, tICAM(185), and tICAM(453) and demonstration of retained capacity for binding to monoclonal antibodies;

Example 7 relates to human rhinovirus binding assays of transmembrane and of non-transmembrane truncated forms of ICAM-1;

Example 8 relates to CL203 IgG antibody-mediated cross-linking of tICAM(453);

Example 9 relates to multimerization of trans-membrane and of non-transmembrane truncated forms of ICAM-1;

Example 10 relates to infectivity-neutralization assay of multimeric transmembrane and of multimeric non-transmembrane truncated forms of ICAM-1; and Example 11 relates to use of multimeric forms of trans-membrane and truncated forms of ICAM-1, as effective inhibitors of ICAM/LFA-1 interaction.

Example 12 relates to construction of tICAM(185)/IgG and tICAM(453)/IgG immunoadhesins.

Example 13 relates to rhinovirus binding and neutralization by a tICAM/IgG immunoadhesins.

Example 14 relates to in vitro dimerization of ICAM-1.

Example 15 relates to a tICAM(1–451)/LFA-3(210–237) chimera.

Example 16 relates to irreversible inactivation of HRV by ICAM.

Example 17 relates to cysteine muteins.

EXAMPLE 1

GROWTH, PURIFICATION AND ASSAY OF RHINOVIRUSES

Rhinoviruses were grown, purified, and assayed essentially as described in Abraham, G., et al., J. Virol., 51:340 (1984) and Greve, et al., Cell, 56:839 (1989). The serotypes chosen for these studies include HRV14, the standard in the field, and HRV3, which has an approximately 10-fold higher affinity for ICAM than does HRV14. HRV2, which binds to the "minor" receptor rather than the "major" receptor, was used as a negative control.

Rhinoviruses HRV2, HRV3, and HRV14 were obtained from the American Type Culture Collection, plaque purified, and isolated from lysates of infected HeLa-S3 cells. Purified rhinovirus was prepared by polyethylene glycol precipitation and sucrose gradient sedimentation. Viral purity was assessed by SDS-PAGE analysis of capsid proteins and by electron microscopy. Infectivity was quantitated by a limiting dilution infectivity assay scoring for cytopathic effect, essentially as described by Minor, P. D., Growth, assay and purification of picornaviruses, in *Virology:A Practical Approach*, B. W. J. Mahy, ed (Oxford:IRL Press), pp. 25–41.

EXAMPLE 2

PRODUCTION AND ISOLATION OF MONOCLONAL ANTIBODIES TO ICAM-1

BALB/cByJ female mice were immunized by intraperitoneal injection of 107 intact HeLa cells in 0.5 ml of phosphate-buffered saline (PBS) three times at 3-week intervals. Two weeks later the mice were bled and aliquots of serum were tested for protective effects against HRV14 infection of HeLa cells. Positive mice were boosted by a final injection of $10^7$ HeLa cells, and 3 days later spleen cells were fused to P3X63-Ag8.653 myeloma cells (Galfre, et al., Nature, 266:550–552 (1977)) to produce a total of approximately 700 hybridoma-containing wells. Each well was tested by incubating $3\times10^4$ HeLa cells in 96-well plates with 100 $\mu$l of supernatant for 1 hr at 37 C; the cells were then washed with PBS, and a sufficient amount of HRV14 was added to give complete cytopathic effect in 24–36 hr. Wells that were positive (protected from infection) were scored at 36 hr.

Cells were removed from wells which scored positive in the first screen and cloned by limiting dilution in 96-well microtiter plates. Supernatants from these wells were tested in the cell protection assay and positive wells were again identified. Further clonings were performed until all of the hybridoma containing wells were positive indicating a clonal population had been obtained. Four cloned cell lines, and their corresponding antibodies, were obtained and were designated c78.1A, c78.2A, c78.4A, c78.5A, c92.1A and c92.5A, respectively.

C92.1A was deposited on Nov. 19, 1987 with the American Type Culture Collection, 12301 Parklawn Drive, Rockville, Md. 20852 and was designated HB 9594.

EXAMPLE 3

CONSTRUCTION OF tICAM cDNAs FROM FULL LENGTH ICAM-1 cDNA

A. Preparation of ICAM-1 cDNA

Randomly-primed cDNA was synthesized from poly A+ RNA from HE1 cells using an Amersham(TM) cDNA synthesis kit under conditions recommended by the supplier. PCR amplification was performed using 100 ng of cDNA for 25 cycles using primers PCR 5.1: (ggaattcATGGCTCCCAGCAGCCCCCGGCCC) (SEQ ID NO:1) and PCR 3.1: (ggaattcTCAGGGAGGCGTGGCTTGTGTGTT) (SEQ ID NO:2). Amplification cycles consisted of 94 C 1 min, 55 C 2 min, and 72 C 4 min. The product of the PCR reaction was digested with EcoR1 and cloned with EcoR1 digested phage vector lambdaGT10 (Stratagene (TM)). Recombinant phage clones were screened by plaque hybridization using ICAM-1 specific oligonucleotides GAGGTGTTCTCAAA-CAGCTCCAGCCCTTGGGGCCGCAGGTCCAGTTC (SEQ ID NO:3) (ICAM1) and CGCTGGCAGGACAAAG-GTCTGGAGCTGGTAGGGGGCCGAGGTGTTCT (SEQ ID NO:4) (ICAM3).

A positive clone designated lambdaHRR4 was selected and purified. The insert was removed by EcoR1 digestion and subcloned into the EcoR1 site of Bluescript KS+. This clone was designated pHRR2. The entire insert was sequenced and found to contain the entire ICAM-1 coding sequence beginning with the initiator ATG codon and ending with the TGA stop codon as specified by the PCR ICAM-1 sequence (Simmons, et al., Nature, 331:624 (1988); Staunton, et al., Cell, 52:925–933 (1988)[SEQ ID NO:20]) except for a single substitution of A-1462 for G. This same change was identified in several independent clones and thus represents a polymorphism of the ICAM-1 gene.

B. Construction of tICAM(453) and tICAM(185)

Modified forms of the ICAM-1 cDNA were created by PCR amplification reactions (Saiki, et al., Science, 230:1350–1354 (1985)) using the full length ICAM-1 cDNA clone pHRR-2 as template. The plasmid DNA was digested with EcoR1 to excise the ICAM-1 insert and treated with alkaline phosphatase to prevent re-circularization of the vector in subsequent ligation steps. Ten ng of template DNA was subjected to 10 cycles of PCR amplification using oligonucleotide primers PCR5.5 and PCR3.3 for tICAM-453 and PCR5.5 and 3.10 for tICAM-185 under the following conditions:

| Temperature (° C.) | Time (mins) |
|---|---|
| 94 | 1 |
| 55 | 2 |
| 72 | 1.5 |
| 71 | 4 (final extension) |

PCR5.5 has the sequence: GGAATTCAAGCTTCT-CAGCCTCGCTATGGCTCCCAGCAGCCCCCGGCCC (SEQ ID NO:5) which consists of EcoR1 and HindIII sites, 12bp ICAM-1 5' untranslated sequence, and the first 24 bp encoding the signal peptide.

PCR3.3 has the sequence: GGAATTCCTGCAGTCACT-CATACCGGGGGAGAGCACATT (SEQ ID NO:6) which consists of EcoR1 and Pst1 sites, a stop codon, and 24 bp complementary to the bases encoding the last 8 extracellular amino acids of ICAM-1 (residues 446–453).

PCR3.10 has the sequence: TTCTAGAGGATCCT-CAAAAGGTCTGGAGCTGGTAGGGGG (SEQ ID NO:7) which consists of Xba1 and BamH1 sites, a stop codon, and 23 bp complementary to the bases encoding residues 178–185 of ICAM-1.

The PCR reaction products were digested with EcoR1 (tICAM(453)) or EcoR1 and BamH1 (tICAM(185)) and cloned into the polylinker site of Bluescript SK+ (Stratagene). Clones containing the desired inserts were verified by restriction analysis and DNA sequencing. The inserts were excised from Bluescript by digestion with HindIII and XbaI and inserted into the expression vector CDM8 (Seed, Nature, 239:840 (1987) at the HindIII and XbaI sites. A clone containing the tICAM(453) insert designated pHRR-8.2 and a clone containing the tICAM(185) insert designated pHRR23–13 were selected and subjected to extensive sequence analysis. This verified the existence of the desired stop codons, and the integrity of the selected regions of ICAM-1 coding sequence.

These plasmids were transfected into COS cells using the DEAE-dextran techniques and the cells were cultured 72 hr. before assay. Surface expression was monitored by FACS using indirect immunofluorescence and a monoclonal antibody specific for ICAM-1. Transient expression in COS cells and immunoprecipitation of metabolically labelled ([$^{35}$S]cysteine) cell supernatants with c78.4A Mab (monoclonal antibody) demonstrated the production of soluble ICAM-1 fragments of 45 kd and 80 kd from pHRR23–13 and pHRR8.2, respectively. The preparation of stable Chinese hamster ovary cell transfectants is described below in Example 4.

C. Modified Non-glycosylated tICAM-1

A modified full length ICAM-1 was made by simultaneous mutagenesis of Asn at positions 103, 118, 156 and 175 each to Gln. This removes all four Asn-linked glycosylation sites from extracellular domain II of the ICAM-1 molecule. The resultant molecule, referred to as non-glycosylated transmembrane ICAM, was expressed on the surface of COS cells and was able to bind radio-labeled HRV3 at levels comparable to unmodified ICAM-1. This result demonstrated that glycosylation of domain II (the first 185 amino acids) is not required for virus binding to ICAM-1.

It is expected that non-transmembrane ICAM can be similarly modified to yield modified non-glycosylated non-transmembrane ICAM-1 molecules.

D. Construction of Genetically Engineered Forms of tICAM Containing Reactive Residues Suitable for Cross-Linking to Form Multimers.

A molecule consisting of the 453 amino acid extracellular domain of ICAM-1 with the addition of a novel lysine residue at the C-terminus was constructed by PCR modification of the pHRR-2 cDNA described in Example 3B. The primers used were PCR5.5 (Example 3B) and PCR 3.19 which has the sequence: TTCTAGAGGATCCTCACTTCT-CATACCGGGGGGAGAGCACATT (SEQ ID NO:8) and consists of XbaI and BamHI sites, a stop codon, a Lys codon, and 24 bases complementary to the sequence encoding amino acid residues 446 to 453. Following cloning into the CDM8 vector, production of tICAM having a Lys at position 453 was confirmed by transient expression in COS cells. Stable CHO cell lines were generated by co-transfection with pSV2-DHFR as described in Example 4. The same strategy was used to add a Lys residue to the C-terminus of tICAM(185) using PCR5.5 and PCR3.20 which has the sequence: TTCTAGAGGATCCTCACTTAAAGGTCTG-GAGCTGGTAGGGGGC (SEQ ID NO:9) and consists of XbaI and BamHI sites, a stop codon, a Lys codon, and 24 bases complementary to the sequence encoding residues 178 to 185. Transient COS cell expression confirmed the production of tICAM-185 and stable CHO cell lines were derived as described in Example 4.

Three modified forms of tICAM(452) that each contain an additional Cys residue were constructed by site-directed mutagenesis of the full-length ICAM-1 cDNA. In each construct a stop codon was introduced by changing the Glu residue at position 453 from GAG to TAG. The C-terminus is thus Tyr-452. Residues Asn-338, Thr-360, and Gln-387 were each separately mutated to Cys using a second site directed mutagenesis. The presence of the desired mutations were confirmed by DNA sequencing.

The residues selected for mutation to Cys were selected based on a computer generated plot of surface probability which predicts surface exposure of these regions. Also, Thr-360 is in close proximity to Asn-358 which is a site of potential Asn-linked glycosylation. Each of the three Cys mutants was expressed and secreted into the medium of transfected COS cells. Examination of the proteins under reducing and non-reducing conditions showed no indication of the presence of dimers. It is anticipated that cross-linking reagents reactive with sulfhydryl groups can be used to cross-link the Cys-modified tICAM forms to obtain multimeric forms.

EXAMPLE 4

TRANSFECTION OF CELLS AND EXPRESSION OF tICAM cDNA

A. Transfection of Eukaryotic Cells

Chinese hamster ovary (CHO) cells deficient in dihydrofolate reductase (DHFR) were obtained from Cutter Labs (Berkeley, Calif.). DHFR- cells cannot synthesize nucleosides and therefore require a nucleoside-supplemented medium. The cells were co-transfected with the plasmid pSV2-DHFR which contains the mouse dihydrofolate reductase (DHFR) gene under control of the SV40 promoter, and with tICAM(453), or tICAM(184) constructs in the CDM8 vector (Seed and Aruffo, PNAS, 84:3365–3369 (1987)).

Transfections were done using both electroporation and calcium phosphate methods. Bebbington, supra. Transfected DHFR-positive cells were selected by growth on nucleoside-free media, and pools of transfectants were cloned by limiting dilution.

Cell lines that secrete tICAM were identified by testing culture supernatants with a two-site radioimmune assay (RIA) for ICAM using Mabs c78.4A and c78.5A as follows. A monoclonal antibody against one epitope on ICAM (for example, Mab c78.4A) was adsorbed to plastic 96-well plates (Immunlon plates, Dynatech Inc.), excess binding sites on the plates were blocked with bovine serum albumin (BSA), and then culture supernatants were incubated with the plates. The plates were washed and incubated with [$^{125}$I]-Mab (directed against a second epitope on ICAM, e.g. c78.5A), and, after washing, the amount of bound [$^{125}$]I-IgG determined. The concentration of tICAM was determined by comparing RIA data from unknowns against a standard curve of tmICAM at known concentrations. Positive clones were expanded and expression of tICAM forms was confirmed by immunoprecipitation of metabolically labeled cell supernatants with Mab c78.4A.

Cell lines CT0.2A (tICAM(453)) and CD12.1A (tICAM (185)) were selected for further study and were subjected to gene amplification in methotrexate containing media as described by Bebbington, et al., supra. A clone derived from CT0.2A resistant to 100 nM methotrexate and a CD12.1A clone resistant to 1 $\mu$M methotrexate were used for purification of soluble truncated ICAM-1 proteins.

B. Transfection of Prokaryotic Cells

Because glycosylation of the viral binding domain of ICAM is not required to retain viral binding (as demonstrated in Example 3C), it is anticipated that prokaryotic cells, such as *E. coli*, can be successfully transfected to produce functional proteins.

EXAMPLE 5

ISOLATION AND PURIFICATION OF tICAM-1

Monoclonal antibody affinity chromatography with c78.4A-Sepharose(TM) has been previously described in co-pending U.S. Ser. No. 07/130,378 and Greve, et al., Cell, 56:839–847 (1989). tICAM secreted into serum-containing media required additional purification steps due to the high level of contaminating protein in the serum. Before elution from the Mab-affinity column, the column was washed with 1 M NaCl to remove loosely-bound proteins. For tICAM (453), the partially purified tICAM(453) eluted from the c78.4-Sepharose(TM) column was dialyzed into 10 mM Tris (pH 6.0), absorbed onto a mono-Q(TM) column (Pharmacia), and eluted with a 0–0.3 M NaCl gradient. tICAM184 was further purified by gel filtration on a Superose-12(TM) column.

It is also recognized that non-transmembrane truncated forms of ICAM-1 may be purified using standard ion exchange methodology without using monoclonal antibody affinity chromatography.

EXAMPLE 6

RADIOACTIVE LABELING OF tmICAM-1, tICAM(185), AND tICAM(453) AND DEMONSTRATION OF RETAINED CAPACITY FOR BINDING TO

MONOCLONAL ANTIBODIES

The epitopes reactive with monoclonal antibodies c78.4A and c78.5A are conformationally-dependent epitopes and thus can be used as analytical probes for confirming retention of the native ICAM structure. Known amounts of purified ICAM were incubated with c78.4A or c78.5A IgG-Sepharose(TM) and the fraction of the radioactivity bound determined. These experiments showed that the purified tmICAM-1, tICAM(185), and tICAM(453) completely retained the ability to bind to these monoclonal antibodies.

Transfectants were metabolically labeled with [$^{35}$S] cysteine, and cell lysates (for transmembrane ICAM) or culture supernatants (for truncated ICAM) were prepared and incubated with c78.4A IgG-Sepharose(TM) beads. The beads were washed and adsorbed proteins were eluted with sodium dodecyl sulfate (SDS) and analysed by SDS-PAGE; see Greve, et al., Cell, 56:839–847 (1989)). It was found that the isolated proteins were quantitatively bound to the c78.4A and c78.5A Mabs.

Accordingly, the tICAM(185) and tICAM(453) both have retained native ICAM structure.

EXAMPLE 7

HUMAN RHINOVIRUS BINDING ASSAYS OF tmICAM AND tICAMs

Described below are three binding assays used to assess binding activity of the various forms of ICAM.

A. Pelleting Assay

[$^{35}$S]cysteine-labeled tmICAM-1 or tICAM was mixed with HRV3 in 100 $\mu$l of 10 mM HEPES (pH 7.5), 150 mM NaCl, 1 mM $MgCl_2$, 1 mM $CaCl_2$, 0.1% Triton X-100. The mixture was incubated for 30 min. at 37 C, cooled on ice, layered on top of a cushion of 200 $\mu$l of 10% glycerol, 0.2 M triethanolamine (pH 7.5), and centrifuged in a Beckman air-driven centrifuge at 134,000×g for 30 min. at 4 C. The top 275 $\mu$l was removed, and the pellet was analyzed by SDS-PAGE and scintillation counting. Silver-staining of SDS gels of control experiments indicated that essentially all of the HRV3 is pelleted under these conditions and essentially all of the ICAM remains in the supernatant. The results are shown in Table 1.

TABLE 1

| ICAM | % ICAM Pelleted* |
|---|---|
| tmICAM-1 | 11.6% |
| tICAM(453) | 1.0% |
| tICAM(185) | 4.3% |

*average of 4 experiments; these numbers cannot be directly converted into relative affinities These data show that both truncated forms of ICAM bind to rhinovirus, but at substantially reduced levels relative to tmICAM.

B. Solution Binding Assay

To obtain quantitative information on the relative affinity of tmICAM and tICAM fragments in solution, a solution competition assay was developed in which soluble tmICAM or soluble tICAM fragments were used to inhibit the binding of [$^{35}$S]HRV3 to previously immobilized ICAM-1; nonionic detergent (Triton X-100) was included in the buffers so that the different proteins could be compared under identical conditions. First, tmICAM-1 (isolated in the presence of 0.1% octylglucoside instead of Triton X-100) was diluted 10-fold into a Tris/NaCl buffer and allowed to adsorb to the walls of a microtiter plate (Immunlon-4, Dynatech) overnight. Nonspecific binding sites on the plate were then blocked with 10 mg/ml BSA and binding experiments performed in 0.1% Triton X-100/1 mg/ml BSA/10 mM Tris/200 mM NaCl. Approximately 20,000 cpm of [$^{35}$S] HRV3 were mixed with varying amounts of ICAM [tmICAM, tICAM(453) or tICAM(185)], incubated for 1 hour at 37 C, and then added to wells of the microtiter plates and incubated for 3 hr at 37 C. The plates were washed and the bound radioactivity determined.

As shown in Table 2, tmICAM-1 inhibits virus binding half-maximally at low concentrations (0.008 μM) while tICAM(453) and tICAM(185) inhibit at much higher concentrations (2.8 μM and 7.9 μM, respectively; or 350 to almost 1000-fold higher than tmICAM.

TABLE 2

| ICAM | IC50* |
|---|---|
| tmICAM | 8.0 ± 3.3 nM (N = 3) |
| tICAM(453) | 2.8 ± 0.6 μM (N = 3) |
| tICAM(185) | 7.9 ± 2.8 μM (N = 3) |

*IC50 is the concentration of soluble ICAM needed to inhibit HRV3 binding by 50%.

These data confirm and extend the earlier observations that tICAM(453) and tICAM(185) do bind to rhinovirus but with lower affinities than does tmICAM-1 and provide evidence that the virus binding site is encompassed within the two N-terminal domains (185 residues) of ICAM-1.

Subsequent experiments performed at 34 C (the temperature at which rhinovirus normally replicates) have yielded similar results.

C. Dot-Blot Assay

An alternative method of measuring binding activity was utilized in which tmICAM-1, tICAM(453), or tICAM(185) was adsorbed to nitrocellulose filters, the non-specific binding sites on the filters blocked with 10 mg/ml bovine serum albumin (BSA), and radioactive virus or [$^{125}$I]Mab to ICAM-1 incubated with the filter for 60 min at 37 C. The filters were washed with buffer and the filters exposed to X-ray film.

The amount of radioactivity bound to the filters was determined by densitometry of the autoradiograms, and the data is expressed as HRV3 binding (in arbitrary units) normalized to the amount of ICAM bound to the blot by a parallel determination of the amount of [$^{125}$I]Mab c78.4A or c78.5A bound to the ICAM (bound to the blot). The results are shown in Table 3.

TABLE 3

| Binding of [$^{35}$S]HRV3 to Immobilized ICAM* | | |
|---|---|---|
| ICAM | tICAM(453) | ratio ICAM/tICAM453 |
| 1.2 ± 1.1 | 0.52 ± 0.45 | 2.3 |

*Average of 5 experiments. Data is expressed in arbitrary densitometric units of [$^{35}$S]HRV3 binding/[$^{125}$I]anti-ICAM Mab binding.

Additional studies with tICAM 185 have been performed. Binding experiments have demonstrated equivocal results. It is anticipated that steric hindrance may play a role. The size of the virus is approximately 30 nanometers. The length of tICAM(185) is less than 10 nanometers. The use of a spacer or linker would provide better accessibility for binding.

The results from this experiment indicate that under these assay conditions tICAM(453) is capable of binding rhinovirus at levels comparable to those of tmICAM-1 when the amount of virus bound was normalized to the amount of [$^{125}$I]MAb bound. Further, these results indicate that the tICAM forms are capable of binding to rhinovirus, but that the binding avidity is dependent upon the configuration of the tICAM. tmICAM-1 is believed to be a small multimer (probably a dimer) and presentation of tICAM in a multimeric form mimics this multimeric configuration.

Evidence supporting this hypothesis comes from quantitative binding studies (unpublished), in which the ratio of the maximum number of rhinovirus particles and the maximum number of antibody molecules that can be bound to cells is approximately 1.5, as discussed supra. This is in contrast to the earlier work of Tomassini, J., et al., J. Virol., 58:290 (1986), which suggested a complex of five molecules needed for binding. Their conclusion was based on an erroneous interpretation of gel filtration data that failed to take into account bound detergent molecules.

EXAMPLE 8

CL203 IgG ANTIBODY-MEDIATED CROSS-LINKING OF tICAM(453)

To provide additional evidence that the higher relative binding activity of tmICAM-1 is due to a multimeric form of the protein, the tICAM(453) protein was pre-incubated with CL203, a monoclonal antibody to ICAM-1 that does not inhibit virus binding to ICAM-1 and binds to a site C-terminal to residue 184 (Staunton, et al., Cell, 56:849 (1989) and Cell, 61:243 (1990)). Thus, the antibody can effectively "cross-link" two molecules of tICAM(453), to create "dimers" of tICAM(453), yet without blocking the virus-binding site on each of the two molecules of tICAM (453). When a mixture of CL203 IgG and tICAM(453) at a 4:1 weight ratio was tested in the competition assay, it was found that the antibody cross-linked tICAM(453) inhibited HRV3 binding at a concentration 7.4-fold lower than tICAM (453) alone consistent with the idea that tmICAM-1 binds with higher affinity to rhinovirus because it is a dimer or a small multimer.

To create alternative multimeric forms of tICAM, several further modified truncated forms of ICAM were constructed as described, supra, in Example 3.

These forms can then be multimerized as described in Example 9, below.

EXAMPLE 9

MULTIMERIZATION OF tmICAM AND tICAMs

There are several ways that tICAM can be converted to a multimeric form having enhanced viral binding and neutralization activity over the monomeric form. For example, a first tICAM can be coupled to a second tICAM(which may be the same or different), or to an inert polymer, such as amino-dextran (MW 40,000), using homobifunctional (such as N-hydroxysuccinimide (NHS) esters) or heterobifunctional (such as those containing NHS-ester and photoactivatable or sulfhydryl-reactive groups) cross-linking reagents utilizing the amino group on the amino-dextran and an amino or other group on the tICAM. A number of examples of appropriate cross-linking reagents can be found in the Pierce Chemical Company catalog (Rockford, Ill.). Similarly, the tICAMs can also be bound to other suitable inert polymers, such as nitrocellulose, PVDF, DEAE, lipid polymer, and other inert polymers that can adsorb or be coupled to tICAM with or without a spacer or linker.

As tICAM is poorly reactive with NHS-ester-based compounds, a tICAM with a genetically-engineered C-terminal lysine residue (see Example 3) would have improved coupling efficiency to supports with homobifunctional reagents whereas genetically-engineered C-terminal cysteine residues would facilitate coupling by heterobifunctional reagents, such as sulfo-maleimidobenzoyl-N-hydroxysuccinimide ester (MBS).

ICAMs can also be multimerized by coupling with an antibody (e.g. CL203) or fragment thereof, or with a suitable protein carrier, e.g. albumin or proteoglycan.

ICAMs may also be multimerized by fusion with fragments of immunoglobulins to form ICAM immunoadhesins.

Alternatively, soluble tICAM multimers can be created by genetically engineering reactive residues into tICAM. For example, free cysteine residues can be created in relatively hydrophilic sequences in the C-terminal region of tICAM (which would have a greater tendency to be solvent-exposed). This will allow the creation of dimers in situ; alternatively, monomers can be purified and dimers created in vitro by disulfide bonding, either directly or via suitable linkers.

Another approach requires the placement of lysine residues at similar positions and cross-linking purified protein in vitro with homobifunctional NHS-esters. Examples of such lysine residues are residues 338, 360, 387.

Crosslinking cysteine residues to each other can be accomplished by reaction of tICAM with free cysteine groups with bis-maleimidohexane (Pierce Chemical Co.) or other bis-maleimido-analogs. Cross-linking free cysteine residues on tICAM to amino groups on carrier molecules can be accomplished by reaction with m-maleimidobenzoyl-N-hydroxy-succinimide ester.

Crosslinking amino groups on tICAM molecules can be accomplished with homobifunctional N-hydroxysuccinimide esters (for examples, see Pierce Chemical Co. catalog). Alternatively, the carbohydrate groups on tICAM can be oxidized to aldehydes and coupled to hydrazine-activated amino groups on a carrier molecule.

EXAMPLE 10

INFECTIVITY-NEUTRALIZATION ASSAY OF tmICAM AND tICAMs

Three different assays for virus infectivity have been used. These different assays take into account the differences in transmembrane ICAM and non-transmembrane solubilities.

A. Plaque-Reduction Assay in the Presence of Detergent

The results of this assay indicate the highest dilution of virus that will still be effective in killing cells. Virus is pre-incubated with transmembrane ICAM protein in the presence of 0.1% Triton X100, serially diluted into culture medium, incubated for 30 min with HeLa cells at $10^6$ cells/ml, diluted 10-fold, and plated out into multiple wells of a 96-well microtiter plate having varying dilutions of virus.

0.1% Triton X100 was used as positive control. After 5 days, the wells are scored as either being infected or not by the presence of cytopathic effect (CPE) and the titer expressed as plaque-forming units/ml (PFU/ml) of the original virus. This assay was described in U.S. Ser. No. 07/239,571 and was used to demonstrate the antiviral activity of tmICAM-1 (which required the presence of detergent to remain in solution). The concentration of ICAM protein used is the initial concentration in the pre-incubation mixture; however, the ICAM protein is not present continually during the infection in that the protein is serially diluted. While the presence of detergent is required to solubilize the tmICAM, detergent kills the cells; thus, the need for the serial dilutions of the tmICAM-1/detergent to permit infection of cells.

B. Plaque-Reduction Assay in the Absence of Detergent

In this plaque-reduction assay, a more traditional assay, HeLa cells are infected with serial dilution of rhinovirus as above, but detergent is not present; thus, this assay cannot be used to assay tmICAM. In this assay the tICAM is present continually in the culture medium at the indicated concentration. tmICAM-1 (which requires the presence of detergent) cannot be assayed in this system because the addition of the required detergent would kill the HeLa cells.

C. Plaque-Reduction Assay in Continual Presence of Virus and ICAM

This assay is similar to that utilized by Marlin, et al. (Nature 1990) in which a culture of HeLa cells is infected with 100 PFU of virus in the presence or absence of ICAM protein and cultured approximately 4 days until cytopathic effect (CPE) is apparent. The cultures are then scored for CPE visually. The assay conditions were the same as Marlin, supra. Scoring was done visually rather than by a staining procedure using crystal violet.

In this assay, there is no detergent present, the ICAM is present continually, and this assay measures a reduction in virus replication/propagation at an arbitrary point in time.

The data from these three different assays for virus infectivity is summarized in Table 4.

TABLE 4

| ICAM | Assay: | A | B | C |
|---|---|---|---|---|
| | | \multicolumn{3}{c}{IC50% (μM)*} | |
| tmICAM-1 | | 0.03 | ND | |
| tICAM(453) | | >20 | 0.2 | 0.2 |
| tICAM(185) | | >20 | 8 | ND |

*IC50% is defined as the concentration of ICAM protein needed to inhibit HRV3 infectivity by 50%.

These data indicate that tmICAM-1 is significantly more active in reducing viral infectivity than the truncated ICAM proteins, even when compared in different assay systems. The differences in neutralization activity of tICAM(453) in assay (A) and assay (B) indicate that the neutralization mediated by tICAM(453) requires the continual presence of tICAM(453) in the culture medium and is reversible. That the neutralization is reversible is indicated by the lack of significant neutralization observed in assay (A). In contrast, the neutralization activity of tmICAM-1 is >667-fold higher than tICAM(453) and than tICAM(185) in assay (A) and could be even greater in assay (B) if it were possible to have the tmICAM-1 present continually in the culture medium in the absence of detergent. The conditions in assays B-D more closely reflect the in vivo situation in which soluble ICAM could be used as an antiviral agent.

To compare these results with those of Marlin et al., an attempt was made to reproduce their assay conditions. As shown in Table 4, there is a good correlation between the results in assay (B) and assay (C), although the IC50% for tICAM(453) is 10-fold greater than that seen by Marlin et al. To determine if this is due to a difference in the serotype of rhinovirus used, the assay was repeated with HRV14 and HRV54 (the serotype used by Marlin, et al.). The IC50% for both of these serotypes was 0.2 μM tICAM(453), indicating that there is no difference in serotype sensitivity between HRV14, HRV54, and HRV3.

To attempt to resolve this discrepancy, the same buffers that Marlin, et al. used were used to see if they affected the infectivity of rhinovirus in assay (C). Marlin, et al. prepared their sICAM-1 protein in a buffer containing 50 mM triethanolamine (TEA)/20 mM Tris. When this buffer alone was added to control infections (1/10th volume, final concentration 5 mM TEA/2 mM Tris) of HRV3 and HRV14, virtually complete inhibition of CPE was observed. Thus, it is possible that there could be buffer effects on virus replication unrelated to the presence of any form of ICAM.

However, subsequent assays using a broad panel of HRV serotypes indicates that the IC50% for HRV54 may in fact be significantly lower than for other HRV serotypes, e.g. HRV3.

EXAMPLE 11

USE OF MULTIMERIC FORMS OF tmICAM AND tICAMs AS EFFECTIVE INHIBITORS OF ICAM/LFA-1 INTERACTION

The normal function of ICAM-1 is to serve as a ligand of the leukocyte integrin LFA-1; interaction between these two molecules leads to adhesion between leukocytes and a variety of other cells. The ability of tICAMs to inhibit adhesion between ICAM-1 and LFA-1 on cells was examined as follows. ICAM-1 was adsorbed to microtiter plates as described in Example 7C. JY cells, which express LFA-1, adhere to ICAM-expressing cells or to ICAM-1-coated culture dishes (Staunton, et al., JCB). JY cells ($10^7$ cell/ml in 10 mM HEPES pH 7.5/150 mM NaCl/1 mM $CaCl_2$/1 mM $MgCl_2$ containing 1 mg/ml BSA) labeled with 10 μCi/ml [$^{36}$S]-cysteine for 18 hours) were pre-incubated in the presence or absence of tICAM(453) or tICAM(185) for 30 min at 37 C, and then added to the ICAM-1-coated plates and incubated for 60 min at 37 C. The microtiter plates were then washed three times with media, and the number of cells bound to the plates were quantified by scintillation counting.

As shown in Table 5, tICAM(185) and tICAM(453) both inhibited JY cell binding at identical concentrations of between 5 and 20 μM.

TABLE 5

| | % JY Cell Binding | |
|---|---|---|
| μM ICAM-1 | tICAM(453) | tICAM(185) |
| 20 | 100 | |
| 6 | 5 | |
| 2 | 47 | 50 |
| 0.6 | 83 | 72 |
| 0.02 | 86 | 80 |
| 0.006 | 89 | 97 |

*Binding to ICAM-1-coated microtiter plates; 10 μg/ml anti-LFA-1 or anti-ICAM-1 MAb inhibited binding to <1%.

EXAMPLE 12

CONSTRUCTION OF tICAM/IgG IMMUNOADHESINS

A soluble derivative of ICAM-1 was constructed by a cDNA fusion which linked the first two domains of ICAM-1 (residues 1–185) to a segment of human immunoglobulin heavy chain cDNA. This approach has been described previously for the CD4 molecule [Zettlmeissl, G., J-P Gregersen, J. M. Duport, S. Mehdi, G. Reiner, and B. Seed, "Expression and Characterization of Human CD4: Immunoglobulin Fusion Proteins", DNA and Cell Biology (1990) 9(5):347–353; Capon, D. J., S. M. Chamow, J. Mordenti, S. A. Marsters, T. Gregory, H. Mitsuya, R. A. Bryn, C. Lucas, F. M. Wurm, J. E. Groopman, S. Broder, and D. H. Smith, "Designing CD4 immunoadhesins for AIDS therapy", Nature (1989) 337:525–531; Traunecker, A. J. Schneider, H. Kiefer and K. Karjalainen, "Highly efficient neutralization of HIV with recombinant CD4-immunoglobulin molecules", Nature (1989) 339:68–70] and resulted in the expression of disulfide-linked dimers.

The cDNA fusion was accomplished by a two-stage polymerase chain reaction (PCR) strategy. [ee, e.g., Horton, R. M., Z. Cai, S. N. Ho, and L. R. Pease, "Gene Splicing by Overlap Extension: Tailor-Made Genes Using the Polymerase Chain Reaction", BioTechniques (1990) 8(5):528–535]. The first step involved the separate amplification of a fragment coding for residues 1–185 of ICAM-1 and an IgG heavy chain fragment beginning at residue 216 in the hinge region and ending at the C-terminus of the molecule (see FIG. 2). The PCR primer used at the 3' end of the ICAM-1 fragment contained an additional 24 bases complementary to the first 24 bases of the IgG fragment: CGG TGG GCA TGT GTG AGT TTT GTC AAA GGT CTG GAG CTG GTA GGG GGC (SEQ ID NO:10). The 5' ICAM-1 primer (5' noncoding and signal sequence) had the sequence:

```
         HindIII
GGA ATT CAA GCT TCT CAG CCT CGC TAT GGC TCC CAG CAG CCC CCG (SEQ ID NO: 5)

GCC C
```

The 5' IgG primer had the following sequence: GAC AAA ACT CAC ACA TGC CCA CGG (SEQ ID NO:11); the 3' primer from the end of the IgG coding sequence was:

```
       XbaI
G GGA TTC TCT AGA TCA TTT ACC CGG AGA CAG GGA GAG GCT    (SEQ ID NO: 12)
```

Amplifications were performed using 10 ng of cloned ICAM-1 or IgG1 heavy chain cDNA for 10 cycles with 1 min at 94 C, 2 min at 55 C and 1.5 min extensions at 72 C. The resulting amplified fragments were mixed in approximately equimolar amounts and used as template for the second step PCR reaction. This reaction used the 5' ICAM primer and the 3' IgG primer above. Amplification for 25 cycles under the same conditions as in the first step produced a predominant band of approximately 1200 bp consistent with the desired product (see FIG. 2). The fragment was digested with HindIII and XbaI (restriction sites incorporated into the 5' and 3' primers respectively), purified and ligated into HindIII/XbaI-cleaved CDM8 vector.

Clones containing the desired insert were identified by restriction analysis and two clones designated pHRR72 and pHRR73 were selected for sequence analysis. Sequencing of the junction region between ICAM-1 and the IgG hinge confirmed that both clones had the correct structure. The plasmids were transfected into COS cells which were labelled with [$^{35}$S]cysteine overnight at 48 hours post-transfection as in Example 6. The supernatants were immunoprecipitated with anti-ICAM-1 monoclonal antibody c78.4A and analyzed by SDS gel electrophoresis as in Example 6. Under reducing conditions a band with an apparent molecular weight of 68 kD was specifically immunoprecipitated, corresponding to the ICAM-1/IgG fusion. Expression of clone pHRR72 was consistently higher than pHRR73 so this clone was selected for further study.

COS cells were transfected with pHRR72 according to the method of Example 3 and at 48 hours after transfection the media was replaced with serum-free media containing [$^{35}$S] cysteine and the cells were labelled overnight as above. The supernatants were incubated with protein A-Sepharose beads, and bound protein was eluted with 0.1 M acetic acid, neutralized and analyzed by gel electrophoresis under reducing and non-reducing conditions. A control was performed in which plasmids expressing heavy and light chains of a functional antibody were co-transfected. This experiment showed that the protein produced by pHRR72 is capable of binding protein A, showing that the pHRR72 protein contains the IgG constant region, and that the 68 kD band seen under reducing conditions shifts to a high molecular weight dimeric form under non-reducing conditions. Thus since only dimeric IgG binds protein A, and since the mobility under non-reducing conditions is at least twice that of the monomer, we conclude that the tICAM(185)/IgG immunoadhesin is a dimer. Correct folding of the ICAM-1 region is indicated by the specific immunoprecipitation with c78.4A as in Example 6, and by the quantitative detection of the fusion protein using two ICAM-1-specific antibodies in a radioimmune assay (RIA) as in Example 4.

pHRR72 was co-transfected with pSV2-DHFR into CHO cells by the calcium phosphate method of Example 4 and DHFR+cells were selected in nucleoside-free medium. Individual colonies were picked, expanded and tested by RIA for expression. The three highest-expressing colonies were selected for further study and were recloned by limiting dilution. Analysis of labelled cell supernatants by protein A binding and gel electrophoresis confirmed the expression of tICAM(185)/IgG dimers.

In a similar manner, domains I–V of ICAM-1 (residues 1–453) were linked to a segment of human immunoglobulin heavy chain cDNA. A fragment coding for residues 1–453 of ICAM-1 and a fragment coding for IgG heavy chain beginning at residue 216 in the hinge region and ending at the C-terminus of the molecule were each separately amplified. The PCR primer used at the 3' end of the ICAM-1 fragment contained an additional 24 bases complementary to the first 24 bases of the IgG fragment: CGG TGG GCA TGT GTG AGT TTT GTC CTC ATA CCG GGG GGA GAG CAC ATT (SEQ ID NO:13). The 5' ICAM-1 primer, 5' IgG primer, and 3' primer from the end of the IgG coding sequence were the same as for the tICAM(185)IgG fusion above. After PCR amplification, a band of approximately 2000 bp consistent with a tICAM(453)/IgG fusion was produced.

Clones containing the desired insert were identified by restriction analysis and the clone designated pHRR 95-9 was selected for sequence analysis. The cDNA sequence is as follows:

```
      CAGACATCTG TGTCCCCCTC AAAAGTCATC CTGCCCCGGG GAGGCTCCGT (SEQ ID NO: 14)
  51  GCTGGTGACA TGCAGCACCT CCTGTGACCA GCCCAAGTTG TTGGGCATAG
 101  AGACCCCGTT GCCTAAAAAG GAGTTGCTCC TGCCTGGGAA CAACCGGAAG
 151  GTGTATGAAC TGAGCAATGT GCAAGAAGAT AGCCAACCAA TGTGCTATTC
 201  AAACTGCCCT GATGGGCAGT CAACAGCTAA AACCTTCCTC ACCGTGTACT
 251  GGACTCCAGA ACGGGTGGAA CTGGCACCCC TCCCCTCTTG GCAGCCAGTG
 301  GGCAAGAACC TTACCCTACG CTGCCAGGTG GAGGGTGGGG CACCCCGGGC
 351  CAACCTCACC GTGGTGCTGC TCCGTGGGGA GAAGGAGCTG AAACGGGAGC
 401  CAGCTGTGGG GGAGCCCGCT GAGGTCACGA CCACGGTGCT GGTGAGGAGA
 451  GATCACCATG GAGCCAATTT CTCGTGCCGC ACTGAACTGG ACCTGCGGCC
 501  CCAAGGGCTG GAGCTGTTTG AGAACACCTC GGCCCCCTAC CAGCTCCAGA
 551  CCTTTGTCCT GCCAGCGACT CCCCCACAAC TTGTCAGCCC CCGGGTCCTA
 601  GAGGTGGACA CGCAGGGGAC CGTGGTCTGT TCCCTGGACG GGCTGTTCCC
 651  AGTCTCGGAG GCCCAGGTCC ACCTGGCACT GGGGGACCAG AGGTTGAACC
 701  CCACAGTCAC CTATGGCAAC GACTCCTTCT CGGCCAAGGC CTCAGTCAGT
 751  GTGACCGCAG AGGACGAGGG CACCCAGCGG CTGACGTGTG CAGTAATACT
 801  GGGGAACCAG AGCCAGGAGA CACTGCAGAC AGTGACCATC TACAGCTTTC
 851  CGGCGCCCAA CGTGATTCTG ACGAAGCCAG AGGTCTCAGA AGGGACCGAG
 901  GTGACAGTGA AGTGTGAGGC CCACCCTAGA GCCAAGGTGA CGCTGAATGG
 951  GGTTCCAGCC CAGCCACTGG GCCCGAGGGC CCAGCTCCTG CTGAAGGCCA
1001  CCCCAGAGGA CAACGGCGCG AGCTTCTCCT GCTCTGCAAC CCTGGAGGTG
1051  GCCGGCCAGC TTATACACAA GAACCAGACC CGGGAGCTTC GTGTCCTGTA
1101  TGGCCCCCGA CTGGACGAGA GGGATTGTCC GGGAAACTGG ACGTGGCCAG
1151  AAAATTCCCA GCAGACTCCA ATGTGCCAGG CTTGGGGGAA CCCATTGCCC
1201  GAGCTCAAGT GTCTAAAGGA TGGCACTTTC CCACTGCCCA TCGGGGAATC
1251  AGTGACTGTC ACTCGAGATC TTGAGGGCAC CTACCTCTGT CGGGCCAGGA
1301  GCACTCAAGG GGAGGTCACC CGCAAGGTGA CCGTGAATGT GCTCTCCCCC
1351  CGGTATGAG
                g acaaaactca cacatgccca ccgtgcccag cacctgaact
1401  cctgggggga ccgtcagtct tcctcttccc cccaaaaccc aaggacaccc
1451  tcatgatctc ccggacccct gaggtcacat gcgtggtggt ggacgtgagc
1501  cacgaagacc ctgaggtcaa gttcaactgg tacgtggacg gcgtggaggt
1551  gcataatgcc aagacaaagc cgcgggagga gcagtacaac agcacgtacc
1601  gggtggtcag cgtcctcacc gtcctgcacc aggactggct gaatggcaag
1651  gagtacaagt gcaaggtctc caacaaagcc ctcccagccc ccatcgagaa
1701  aaccatctcc aaagccaaag ggcagccccg agaaccacag gtgtacaccc
1751  tgcccccatc ccgggatgag ctgaccaaga accaggtcag cctgacctgc
1801  ctggtcaaag gcttctatcc cagcgacatc gccgtggagt gggagagcaa
1851  tgggcagccg gagaacaact acaagaccac gcctcccgtg ctggactccg
```

```
-continued
1901 'acggctcctt cttcctctac agcaagctca ccgtggacaa gagcaggtgg 1951  cagcagggga acgtcttctc atgctccgtg atgcatgagg ctctgcacaa 2001  ccactacacg cagaagagcc tctccctgtc tccgggtaaa tga
(wherein UPPERCASE indicates nucleotides coding for amino acid residues 1-453
of ICAM-1, and lowercase indicates nucleotides coding from amino acid residues
216-442 of human heavy chain IgG1)
```

The corresponding amino acid sequence of the mature fusion polypeptide is as follows:

```
  1 QTSVSPSKVI LPRGGSVLVT CSTSCDQPKL LGIETPLPKK ELLLPGNNRK(SEQ ID NO: 15)

51 VYELSNVQED SQPMCYSNCP DGQSTAKTFL TVYWTPERVE LAPLPSWQPV

101 GKNLTLRCQV EGGAPRANLT VVLLRGEKEL KREPAVGEPA EVTTTVLVRR

151 DHHGANFSCR TELDLRPQGL ELFENTSAPY QLQTFVLPAT PPQLVSPRVL

201 EVDTQGTVVC SLDGLFPVSE AQVHLALGDQ RLNPTVTYGN DSFSAKASVS

251 VTAEDEGTQR LTCAVILGNQ SQETLQTVTI YSFPAPNVLL TKPEVSEGTE

301 VTVKCEAHPR AKVTLNGVPA QPLGPRAQLL LKATPEDNGR SFSCSATLEV

351 AGQLIHKNQT RELRVLYGPR LDERDCPGNW TWPENSQQTP MCQAWGNPLP

401 ELKCLKDGTF PLPIGESVTV TRDLEGTYLC RARSTQGEVT RKVTVNVLSP

451 RYEDKTHTCP PCPAPELLGG PSVFLFPPKP KDTLMISRTP EVTCVVVDVS

501 HEDPEVKFNW YVDGVEVHNA KTKPREEQYN STYRVVSVLT VLHQDWLNGK

551 EYKCKVSNKA LPAPIEKTIS KAKGQPREPQ VYTLPPSRDE LTKNQVSLTC

601 LVKGFYPSDI AVEWESNGQP ENNYKTTPPV LDSDGSFFLY SKLTVDKSRW

651 QQGNVFSCSV MHEALHNHYT QKSLSLSPGK *
```

The plasmids were transfected into COS cells which were labelled with [$^{35}$S]cysteine overnight at 48 hours post-transfection as in Example 6. The fusion polypeptide is expressed as a soluble secreted disulfide-linked dimer which binds protein A. The supernatants were immunoprecipitated with anti-ICAM-1 monoclonal antibody c78.4A and analyzed by SDS gel electrophoresis as in Example 6. Under reducing conditions a band with an apparent molecular weight of 100 kD was specifically immunoprecipitated, corresponding to the ICAM-1/IgG fusion, while under non-reducing conditions it migrates as a 200 kD dimer.

EXAMPLE 13

RHINOVIRUS BINDING AND NEUTRALIZATION BY tICAM/IgG IMMUNOADHESINS

The tICAM(185)/IgG immunoadhesin of Example 12 consists of residues 1–185 of ICAM-1 fused to residue 216 in the hinge region of an IgG1 heavy chain. The molecule is a disulfide-linked dimer containing two rhinovirus binding sites. A CHO cell line CHO72.2 secreting the immunoadhesin was grown overnight in serum-free media containing [$^{35}$S]cysteine and the fusion protein was purified on protein A beads. The labelled protein was tested for rhinovirus binding in the pelleting assay as described in Example 7(A). The samples consisted of tICAM(185)/IgG (no virus), tICAM(185)/IgG+HRV3, tICAM(185)/IgG+HRV3+ c78.4A, and tICAM(185)/IgG+HRV3+irrelevant antibody.

Pelleting of labelled protein indicative of virus binding was seen with virus and virus+irrelevant antibody by analysis on SDS gels. No pelleting was seen in the absence of virus and significantly reduced pelleting was seen in the sample containing c78.4A. This result indicates that the tICAM(185)/ IgG binds rhinovirus with a significantly higher affinity than the soluble monomers tICAM(185) and tICAM(453), which do not show levels of binding readily detectable under these conditions. See Example 7(A). While approximately 10% of tmICAM-1 pellets under these conditions, only 1% of tICAM(453) pellets, presumably because tmICAM-1 is in a dimeric state. The result with tICAM(185)/IgG is similar to that seen in this assay with tmICAM-1, suggesting that the two forms of ICAM may have similar affinities for the virus, and providing further evidence that tmICAM-1 is a dimer.

Cell supernatant from CHO72.2 cells containing unpurified tICAM(185)/IgG was tested for rhinovirus neutralization in a virus infectivity assay according to the method of Example 10(B). Serial dilutions of HRV3 were made in media containing 50% IgG supernatant or control supernatant from untransfected CHO cells. The virus dilutions were mixed with HeLa cells and plated in wells of a 96-well microtiter plate (10 wells per dilution). Virus titers were determined by scoring the number of infected wells at each dilution after 6 days. In addition a quantitative assessment of cytopathic effect at high virus input was made 2 days after infection. In experiment A the concentration of tICAM(185)/ IgG estimated by RIA was 150 ng/ml and in experiment (B) the concentration was 325 ng/ml.

TABLE 6

|                          | Experiment A              | Experiment B              |
|--------------------------|---------------------------|---------------------------|
| HRV3                     | 1 × 10⁷ PFU/ml            | 4 × 10⁶ PFU/ml            |
| HRV3 + tICAM(185)/IgG    | 6 × 10⁵ PFU/ml            | 5 × 10⁵ PFU/ml            |

Both experiments resulted in a ten-fold reduction in viral titer at a concentration of approximately 1 nM in experiment A and 2 nM in experiment B. For comparison, monomeric tICAM(453) in the same assay results in a 50% reduction in titer at 0.38 $\mu$M or 30 $\mu$g/ml. Thus the increase in activity resulting from dimerization of the rhinovirus binding site is at least 200-fold and probably greater.

Cell supernatant from CHO72.2 at a concentration of 650 ng/ml (4 nM) was also tested in a competitive binding assay measuring the binding of [$^{35}$S]HRV3 to ICAM-1-coated plastic microtiter wells. Specific binding is determined by comparing counts bound with or without pre-incubation of the ICAM-1 in the well with Mab c78.4A.

TABLE 7

|                          | cpm bound*    | % binding |
|--------------------------|---------------|-----------|
| HRV3                     | 4945 +/− 58   | 100       |
| HRV3 + CHO supernatant   | 5358 +/− 51   | 108       |
| HRV3 + CHO72.2 supernatant | 3187 +/− 206 | 64        |

*Mean values determined from triplicate wells. Standard errors were less than 10% of the mean.

The level of binding in the presence of tICAM(185)/IgG was 65% of the normal control binding and 54% of control binding in the presence of CHO cell supernatant, indicating close to a 50% inhibition of binding. For comparison, soluble monomeric tICAM(453) inhibits HRV3 binding by 50% in the same assay at 240 $\mu$g/ml or 3.1 $\mu$M. On a molar basis the ICAM-1 IgG immunoadhesin was thus almost a 1000-fold better competitor than the monomer. The above experiments were done with supernatants. Subsequent attempts to reproduce these results with highly purified tICAM(185)/IgG were unsuccessful.

The tICAM(453)/IgG immunoadhesin of Example 12 consists of residues 1–453 of ICAM-1 fused to residue 216 in the hinge region of an IgG1 heavy chain. The molecule is a disulfide-linked dimer containing two rhinovirus binding sites. The fusion polypeptide was expressed in HeLa cells using the vaccinia/T7 system and purified from the supernatant by affinity chromatography using an anti-ICAM-1 monoclonal antibody. The activity of the protein was examined in a competitive binding assay which measures the binding of [$^{35}$S]-labelled HRV to plates coated with purified tmICAM-1. For comparison, soluble monomeric tICAM-453 was included in a parallel assay as a positive control. The binding values are documented in Table 8 below:

TABLE 8

|                   | IC₅₀*  |
|-------------------|--------|
| tICAM(453)        | 44 nM  |
| t(453)/IgG        |        |
| Experiment 1      | 11 nM  |
| Experiment 2      | 10 nM  |

*IC$_{50}$ is the concentration required to inhibit binding by 50%

These values are per mol of tICAM(453) determined by RIA. Since each fusion polypeptide contains two tICAM (453) polypeptides, the values for the fusion polypeptide expressed per mol of dimer are 5.5 nM and 5 nM for Experiments 1 and 2, respectively. Therefore on a molar basis the activity of the fusion polypeptide in the competitive binding assay is ten-fold greater than the tICAM(453) monomer. In subsequent experiments the relative activity was 2- to 4-fold greater.

EXAMPLE 14

IN VITRO DIMERIZATION OF ICAM-1

Figure 3B:
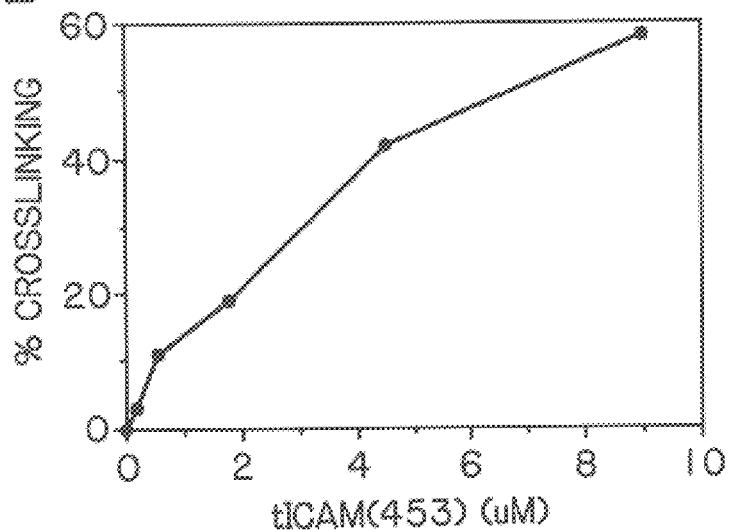
Figure 3C:
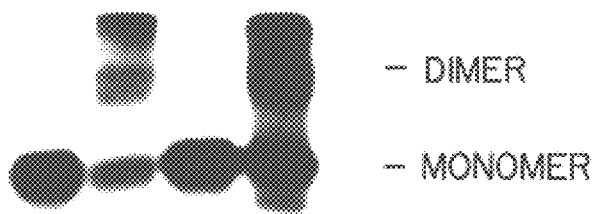
Figure 4A:
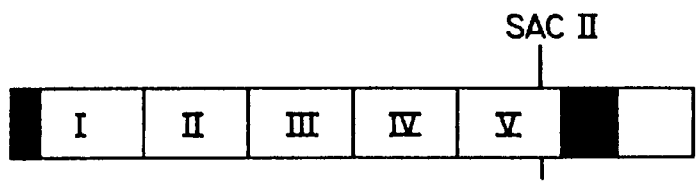
Figure 4B:
Figure 4C:
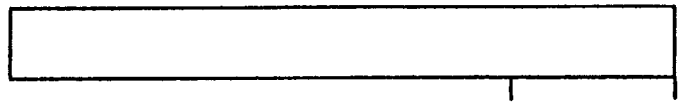
Figure 4D:
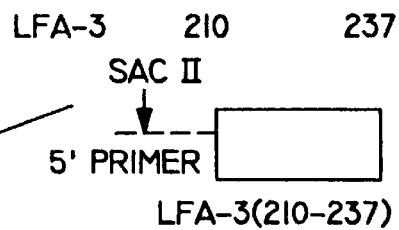
Figure 4E:
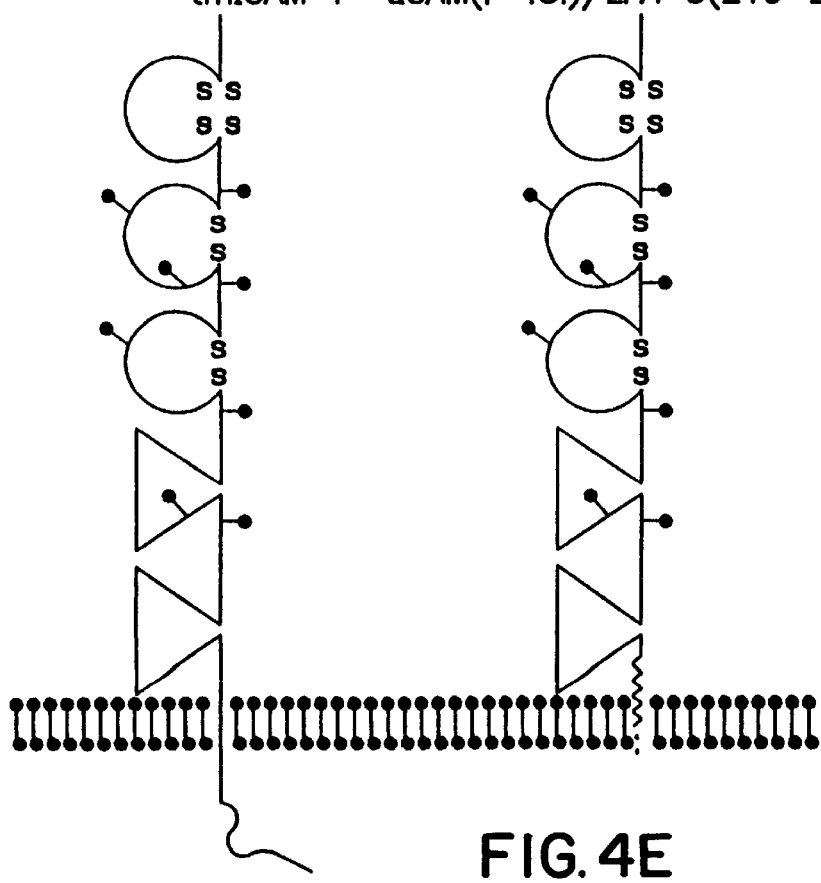

Several lines of evidence indicate that tmICAM-1 exists as a noncovalent dimer at the cell surface: (i) the stoichiometry of HRV/ICAM-1 binding sites at the cell surface is approximately 2; (ii) tICAM(453), despite being properly folded, has a approximately 100-fold lower affinity for HRV than purified tmICAM-1; and (iii) tICAM(453) and tmICAM-1 absorbed to nitrocellulose filters at a high density bind rhinovirus at equivalent levels. See Example 7. In addition, Staunton et al. (Cell 61:243–254 (1990)) have reported that some mutants of ICAM-1 form covalent dimers at the cell surface, indicating that this protein has the capability to self-associate in vivo. Attempts to directly demonstrate the existence of dimers by chemical cross-linking with water-soluble carbodiimide/NHS, which is a heterobifunctional crosslinker which forms a covalent bond between a primary amine and a carboxyl group, did result in crosslinking of tICAM(453) into a 180 kD species, whose size is consistent with a dimer (FIG. 3A). This crosslinking is directly dependent upon the concentration of tICAM (453), with 50% crosslinking at 7 $\mu$M protein (FIG. 3B). This concentration is consistent with the relatively high concentration of tmICAM-1 at the surface of a HeLa cell, which is approximately 2.5 $\mu$M or 135 $\mu$g/ml. The self-association detected by this crosslinking is specific, since it is not affected by high concentrations of third-party proteins (FIG. 3C). tICAM(185) appears to be poorly crosslinked under the same conditions, indicating that domains 3–5 are involved in self-association. Because of the extensive modification of the protein by this crosslinking procedure, the protein had no virus-binding activity. However, this data shows that soluble ICAM can self-associate in solution, and that this self-association is concentration-dependent and -specific.

EXAMPLE 15

A tICAM(1–451)/LFA-3(210–237) CHIMERA

In order to examine the role of the transmembrane and cytoplasmic domains of tmICAM-1 in high-affinity rhinovirus binding, we constructed a chimeric ICAM-1 which is anchored on the cell surface by a phospholipid tail and lacks these domains (see FIG. 4). This experiment was designed to test whether the cytoplasmic and transmembrane domains are necessary for the formation of dimeric ICAM-1 on the cell surface, which results in the high affinity binding of rhinovirus. In order to modify the ICAM-1 cDNA to express a phospholipid-anchored form, we first used site-directed mutagenesis to create a unique SacII site at residues 450/451 close to the end of the extracellular region. This allowed the isolation of a cDNA fragment coding for residues 1–451 of ICAM-1, by digestion of the modified plasmid with HindIII and SacII. We used PCR to generate a fragment coding for the C-terminal 28 amino acids of the phospholipid-anchored form of LFA-3 (Seed, B., Nature (1987) 329:840–842). By including a SacII site in the 5' primer this fragment was ligated to the ICAM-1 extracellular domain and cloned into the expression vector CDM8, resulting in the plasmid pHRR 70-19. This plasmid contains a cDNA coding for residues 1–451 of ICAM-1 fused to residues 210–237 of LFA-1, which should result in the expression of a phosphoplipid-anchored molecule containing the ICAM-1 extracellular region. See FIG. 4.

Transfection of COS cells with pHRR 70-19 according to the method of Example 4 and FACS analysis with anti-ICAM-1 antibodies confirmed the cell surface expression of the fusion protein. The binding of [$^{35}$S]-labelled cells to COS cells transfected with the fusion protein was determined.

TABLE 9

| ICAM-1 | cpm bound | % virus input | % control |
|---|---|---|---|
| tmICAM-1 | 2130 +/− 278 | 9.4 | 100 |
| tICAM(1-185)/ LFA-3 (210–237) chimera | 2382 +/− 293 | 11.2 | 119 |

This result shows that there is no significant difference between the ability of tmICAM-1 and the tICAM(1–451)/LFA-3(210–237) chimera to bind HRV. It can therefore be concluded that the transmembrane and cytoplasmic domains are not required for HRV binding, and that dimerization must depend on interactions between extracellular regions of the molecule.

Additional evidence that a form of ICAM-1 lacking the cytoplasmic and transmembrane domains functions efficiently as a receptor for rhinoviruses was obtained by transfection of the tICAM(1–451)/LFA-3(210–237) chimeric gene into HeLa 229 cells. We have determined that these cells do not express ICAM-1 on the surface and are resistant to HRV infection. Transfection of either tmICAM-1 or the tICAM(1–451)/LFA-3(210–237) chimera results in cells which are readily infectable with rhinovirus and produce virus at levels comparable to normal HeLa cells.

EXAMPLE 16

IRREVERSIBLE INACTIVATION OF HRV BY ICAM

Figure 5C:
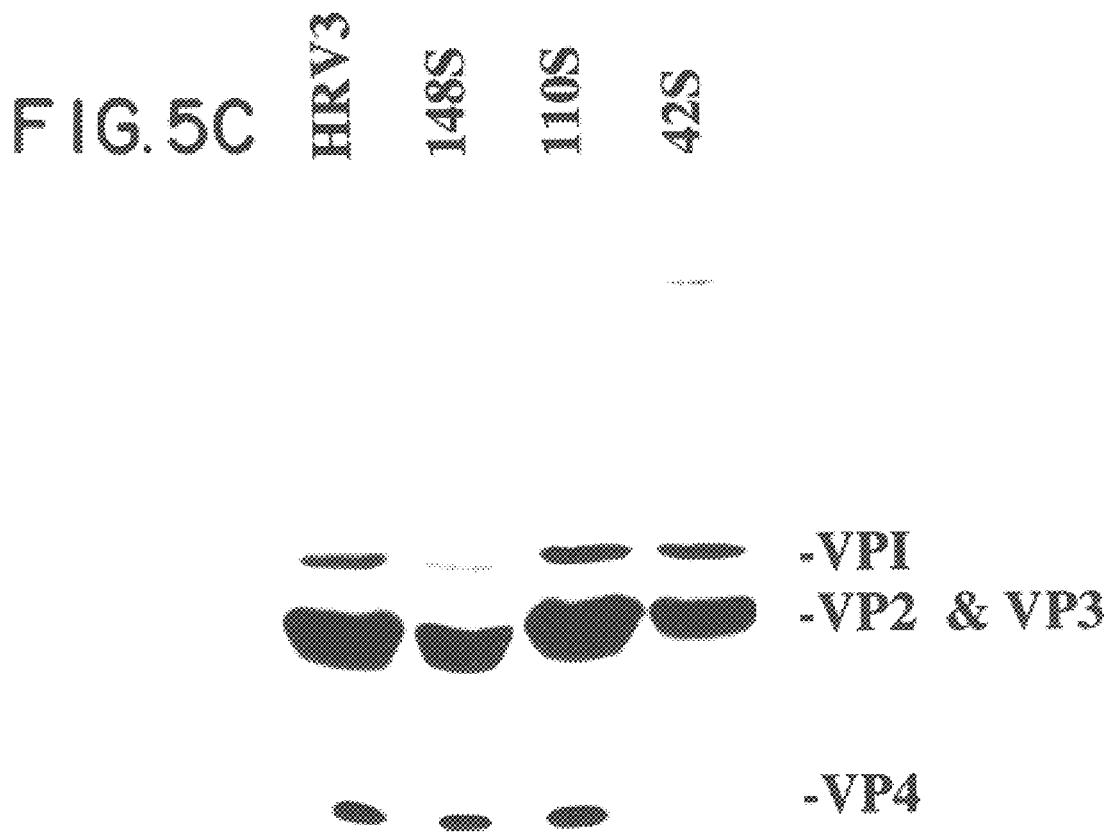
Figure 5D:

We have demonstrated that tICAM(453) can, in addition to blocking the binding of HRV to cells, irreversibly inactivate HRV. Incubation of HRV with tICAM(453) at 34 C results in conversion of a fraction of the virus from the native 148S form to a 42S form (FIG. 5). The 42S form is non-infectious, lacks the viral subunit VP4, and lacks the RNA genome (empty capsid). This can be shown by SDS-PAGE analysis of [$^{35}$S]methionine-labelled viral particles and by quantitation of viral RNA content by hybridization with a [$^{32}$P]oligonucleotide probe for rhinovirus (5'-GCATTCAGGGGCCGGAG-3') (SEQ ID NO:16). Thus, tICAM(453) can uncoat rhinovirus, an event that normally occurs intracellularly during the course of infection. The uncoating is a slow process, occurring with a t1/2 of 6 hours at 34 C, in contrast with the inhibition of binding, which occurs with a t1/2 of <30 minutes. The uncoating is highly temperature-dependent, occurring 10 times faster at 37 C than at 34 C, the optimal temperature of rhinovirus growth. Enhancement of this uncoating activity by soluble forms of ICAM-1 including multimeric configurations of ICAM-1 will lead to improvement of antiviral activity by making neutralization irreversible.

Example 17

CYSTEINE MUTEINS

To identify the correct site to place cysteine residues for multimerization of ICAM-1, the region of the protein surface involved in self-association must be identified. Domains IV and V have been chosen because they are distal to the viral binding sites (domain I) and because domains II–V are implicated in self-association (see Example 14). Since the structure of ICAM-1 is not certain, we have attempted to align the sequence of domains IV and V at the C-terminus of the extracellular domain of ICAM-1 onto the immunoglobulin fold, as ICAM-1 has homology to numbers of the immunoglobulin supergene family. This alignment is shown diagrammatically in FIG. 6. Then, to identify probable sites involved in self-association, we have examined the three-dimensional structures of several members of the immunoglobulin supergene family, IgG and MHC1/beta-2 microglobulin. Immunoglobulin domains have two broad faces of beta sheet structure, here designated the "B" face and the "F" face. Inspection of the above structures revealed that different immunoglobulin-like domains interacted via one or the other of these faces of the domain. IgG variable regions associated via their F face, while IgG constant regions (CH1, CH2, and CH3) and MHC1/beta-2 microglobulin all interact via their B faces.

ICAM-1 domains have highest homology to constant region-like domains. Thus, the most likely sites of interaction are on the B face of the domains; the most likely sites on the B face to place cysteine residues are close to the center of the B face (adjacent to the cysteine on the B strand that forms the intrachain disulfide bond), where IgG CH3 domains self-associate, or on the N-terminal end of the B face, where IgG CH2 domains and MHC1/beta-2 microglobulin self-associate.

A number of mutants were prepared to identify appropriate sites of interaction. These mutants were prepared by standard site-directed mutagenesis methodology to mutate selected residues to cysteine on tICAM(453) and tmICAM. These cDNAs in the vector CDM8 were then transfected into COS cells and dimer formation accessed by biosynthetic labelling of ICAM-1 with [$^{35}$S]cysteine followed by immunoprecipitation and non-reducing SDS-PAGE analysis. As shown in Table 10, of 13 mutants tested, two have been found to form dimers at a small (about 5%) but significant level:

TABLE 10

| Position of Cysteine | Dimer Formation |
|---|---|
| (tmICAM-1) | |
| 304 | − |
| 306 | − |
| 307 | + |
| 309 | + |
| 375 | − |
| 377 | − |
| 378 | − |
| 380 | − |
| 382 | − |
| 429 | − |
| (tICAM(453)) | |
| 338 | − |
| 360 | − |
| 378 | − |

These two muteins, Cys-307 and Cys-309, are both located on the N-terminal end of the B face of domain IV. The relatively low level of dimerization may reflect the low concentration of ICAM-1 on the cell surface (low expression), or imperfect orientation of the cysteine residues relative to the site of interaction. These data indicate that this region of the domain is a likely site of interaction. Other residues adjacent to residues 307 and 309, e.g. His-308, Arg-310, Glu-294, Arg-326, Gln-328, are likely to increase the efficiency of the dimer formation. Mutations that lead to dimer formation of tmICAM-1 are then be placed on tICAM (453) for the secretion of soluble ICAM-1 dimers.

A tICAM(452) cysteine mutant was prepared by substituting a cysteine for an alanine at position 307 in the ICAM-1 amino acid sequence and inserting a stop codon after amino acid residue 452. The mutein was constructed by site-directed mutagenesis using a full-length ICAM-1 cDNA and has the following DNA sequence:

For example, it is anticipated that smaller protein fragments and peptides derived from ICAM-1 that still contain the virus-binding site would also be effective in a multimeric configuration. It is also anticipated that multimeric ICAM may be effective inhibitors of the ICAM-1/LFA-1 interaction, as the affinity between these two molecules is quite low and the cell-cell binding mediated by these two molecules is highly cooperative.

Although the preferred form and configuration is a non-transmembrane (truncated) ICAM in dimeric configuration, it is not intended to preclude other forms and configurations

```
        CAGACATCTG TGTCCCCCTC AAAAGTCATC CTGCCCCGGG GAGGCTCCGT(SEQ ID NO: 17)

51 GCTGGTGACA TGCAGCACCT CCTGTGACCA GCCCAAGTTG TTGGGCATAG

101 AGACCCCGTT GCCTAAAAAG GAGTTGCTCC TGCCTGGGAA CAACCGGAAG

151 GTGTATGAAC TGAGCAATGT GCAAGAAGAT AGCCAACCAA TGTGCTATTC

201 AAACTGCCCT GATGGGCAGT CAACAGCTAA AACCTTCCTC ACCGTGTACT

251 GGACTCCAGA ACGGGTGGAA CTGGCACCCC TCCCCTCTTG GCAGCCAGTG

301 GGCAAGAACC TTACCCTACG CTGCCAGGTG GAGGGTGGGG CACCCCGGGC

351 CAACCTCACC GTGGTGCTGC TCCGTGGGGA GAAGGAGCTG AAACGGGAGC

401 CAGCTGTGGG GGAGCCCGCT GAGGTCACGA CCACGGTGCT GGTGAGGAGA

451 GATCACCATG GAGCCAATTT CTCGTGCCGC ACTGAACTGG ACCTGCGGCC

501 CCAAGGGCTG GAGCTGTTTG AGAACACCTC GGCCCCCTAC CAGCTCCAGA

551 CCTTTGTCCT GCCAGCGACT CCCCCACAAC TTGTCAGCCC CCGGGTCCTA

601 GAGGTGGACA CGCAGGGGAC CGTGGTCTGT TCCCTGGACG GGCTGTTCCC

651 AGTCTCGGAG GCCCAGGTCC ACCTGGCACT GGGGGACCAG AGGTTGAACC

701 CCACAGTCAC CTATGGCAAC GACTCCTTCT CGGCCAAGGC CTCAGTCAGT

751 GTGACCGCAG AGGACGAGGG CACCCAGCGG CTGACGTGTG CAGTAATACT

801 GGGGAACCAG AGCCAGGAGA CACTGCAGAC AGTGACCATC TACAGCTTTC

851 CGGCGCCCAA CGTGATTCTG ACGAAGCCAG AGGTCTCAGA AGGGACCGAG

901 GTGACAGTGA AGTGTGAGtg CCACccgcgg GCCAAGGTGA CGCTGAATGG

951 GGTTCCAGCC CAGCCACTGG GCCCGAGGGC CCAGCTCCTG CTGAAGGCCA

1001 CCCCAGAGGA CAACGGGCGC AGCTTCTCCT GCTCTGCAAC CCTGGAGGTG

1051 GCCGGCCAGC TTATACACAA GAACCAGACC CGGGAGCTTC GTGTCCTGTA

1101 TGGCCCCCGA CTGGACGAGA GGGATTGTCC GGGAAACTGG ACGTGGCCAG

1151 AAAATTCCCA GCAGACTCCA ATGTGCCAGG CTTGGGGGAA CCCATTGCCC

1201 GAGCTCAAGT GTCTAAAGGA TGGCACTTTC CCACTGCCCA TCGGGGAATC

1251 AGTGACTGTC ACTCGAGATC TTGAGGGCAC CTACCTCTGT CGGGCCAGGA

1301 GCACTCAAGG GGAGGTCACC CGCAAGGTGA CCGTGAATGT GCTCTCCCCC

1351 CGGTATTAG
```

The foregoing examples describe the creation of soluble, multimeric forms of tICAM that substantially increase tICAM binding and neutralizing activity.

While the present invention has been described in terms of specific methods and compositions, it is understood that variations and modifications will occur to those skilled in the art upon consideration of the present invention.

effective in binding virus and effective in neutralizing viral activity from being included in the scope of the present invention.

Further, it is anticipated that the general method of the invention of preparing soluble protein forms from insoluble, normally membrane bound receptor proteins can be used to prepare soluble multimeric forms of other receptor proteins useful for binding to and decreasing infectivity of viruses other than those that bind to the "major group" receptor. Such other viruses include polio, Herpes simplex, and Epstein-Barr virus.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A method for reducing the infection by human rhinovirus (HRV) of host cells susceptible to infection by HRV, comprising contacting the virus under conditions favorable for binding with a multimeric antiviral agent comprising two or more units wherein said units may be the same or different and are each independently selected from the group consisting of transmembrane intercellular adhesion molecule-1 (tmICAM-1) and truncated forms of intercellular adhesion molecule-1 (tICAMs), each of said units containing at least one unpaired cysteine residue at a position selected from the group consisting of 307 and 309, wherein each of said units is linked to at least one other of said units via a disulfide bridge, and wherein said multimeric antiviral agent binds to HRV and reduces infectivity thereof.

2. A method for reducing infectivity of human rhinovirus of the major receptor class, said method comprising contacting said virus under conditions favorable for binding with a multimeric antiviral agent comprising two or more units wherein said units may be the same or different and are each independently selected from the group consisting of transmembrane intercellular adhesion molecule-1 (tmICAM-1) and truncated forms of intercellular adhesion molecule-1 (tICAMs), each of said units containing at least one unpaired cysteine residue at a position selected from the group consisting of 307 and 309, wherein each of said units is linked to at least one other of said units via a disulfide bridge, and wherein said multimeric antiviral agent binds to HRV and reduces infectivity thereof.

3. A method for reducing the initiation or spread of the common cold due to human rhinovirus (HRV), said method comprising contacting said virus with a multimeric antiviral agent comprising two or more units wherein said units may be the same or different and are each independently selected from the group consisting of transmembrane intercellular adhesion molecule-1 (tmICAM-1) and truncated forms of intercellular adhesion molecule-1 (tICAMs), each of said units containing at least one unpaired cysteine residue at a position selected from the group consisting of 307 and 309, wherein each of said units is linked to at least one other of said units via a disulfide bridge, and wherein said multimeric antiviral agent binds to HRV and reduces infectivity thereof.

4. The method of claim 1, 2, or 3 wherein at least one of said units is tmICAM-1.

5. The method of claim 1, 2, or 3 wherein all of said units are tmICAM-1.

6. The method of claim 1, 2, or 3 wherein at least one of said units is tICAM(453).

7. The method of claim 1, 2, or 3 wherein all of said units are tICAM(453).

* * * * *